US006492511B2

(12) United States Patent
Callen et al.

(10) Patent No.: US 6,492,511 B2
(45) Date of Patent: **\*Dec. 10, 2002**

(54) ISOLATION AND IDENTIFICATION OF NOVEL POLYMERASES

(75) Inventors: Walter Callen, San Diego; Eric J. Mathur, Carlsbad, both of CA (US)

(73) Assignee: Diversa Corporation, San Diego, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 09/391,340

(22) Filed: Sep. 7, 1999

(65) Prior Publication Data

US 2002/0013455 A1 Jan. 31, 2002

Related U.S. Application Data

(62) Division of application No. 08/907,166, filed on Aug. 6, 1997, now Pat. No. 5,948,666.

(51) Int. Cl.$^7$ .................. C07H 21/04; C07H 21/00; C12N 9/12
(52) U.S. Cl. .................. 536/24.3; 435/194; 536/23.1; 536/24.32; 536/24.33
(58) Field of Search .............. 536/23.1, 24.3, 536/24.32, 24.33; 435/194

(56) References Cited

U.S. PATENT DOCUMENTS

H1531 H * 5/1996 Blumentals et al. ........ 435/194
5,948,666 A * 9/1999 Callen et al. ............... 435/194

* cited by examiner

*Primary Examiner*—Rebecca E. Prouty
*Assistant Examiner*—Richard Hutson
(74) *Attorney, Agent, or Firm*—Fish & Richardson P.C.

(57) ABSTRACT

The invention provides purified thermostable enzymes derived from various extremophilic prokaryotic organisms. The enzymes have polymerase activity and can be used to catalyze DNA synthesis by addition of deoxynucleotides to the 3' end of a polynucleotide chain, using a complementary polynucleotide strands as a template.

9 Claims, 42 Drawing Sheets

```
(SEQ ID NO:1) GTG AAG GGA AAA ACC TTG CTC CTT TTG GAC GGC TCG AGC ATA GCC TAC CGG
(SEQ ID NO:2) Val Lys Gly Lys Thr Leu Leu Leu Leu Asp Gly Ser Ser Ile Ala Tyr Arg

GCC TTT TTC GCC CTT CCC CTC TCC ATG CTC TTC AAA GTG GCC CTG GAA GAA AGG CGT
Ala Phe Phe Ala Leu Pro Ser Leu Arg Thr Arg Thr Gly Leu Pro Thr Gly

GCC GTG TAC GGC TTT ACC TCC ATG CTC TTC AAA GTG CTG GAA GAA AGG CGT
Ala Val Tyr Gly Phe Thr Ser Met Leu Phe Lys Val Leu Glu Glu Arg Arg

CCC ACG GCC ATA GTG GCG GCT TTC GAT AAA AGC AAG ACC TTC CGG CAC
Pro Thr Ala Ile Val Ala Ala Phe Asp Lys Ser Lys Thr Thr Phe Arg His

GCC CTG GCG GAG ACC TAC AAG GCC CAC CGC CCC GCC ACT CCG GAT GAA CTG
Ala Leu Ala Glu Thr Tyr Lys Ala His Arg Pro Ala Thr Pro Asp Glu Leu

CGC CAG CAG TTC AAC CTC ATC AAG GAA GTG CTG ACT GCC CTC AAC GTT CCG
Arg Gln Gln Phe Asn Leu Ile Lys Glu Val Leu Thr Ala Leu Asn Val Pro

GTA GTG GAA AGG GAG GGT TTT GAG GCC GAC GAC CTC ATC GGC ACT CTG GTA
Val Val Glu Lys Glu Gly Phe Glu Ala Asp Asp Leu Ile Gly Thr Leu Val
```

*FIGURE 1A*

```
GAC CGG GCG GAA AAA GAG GGT TGG CAG TGC CTT ATC GTC ACC GGC GAC CTC
Asp Arg Ala Glu Lys Glu Gly Trp Gln Cys Leu Ile Val Thr Gly Asp Leu

GAC GCC CTG CAG CTG GTT TCC CCC CTC ACC GTC GTC ATG CGC AAG
Asp Ala Leu Gln Leu Val Ser Pro Leu Thr Val Val Met Arg Lys

GGG ATA AGC GAA ATA GCG GTC TTT AAC GAG GCG GAG GTG AAA CGC TTC
Gly Ile Ser Glu Ile Ala Val Phe Asn Glu Ala Glu Val Lys Arg Phe

GGC GTC ACA CCC CGC CAA CTC CCC GAC TTC AAA GCC TTG GCC GGA GAT GCC
Gly Val Thr Pro Arg Gln Leu Pro Asp Phe Lys Ala Leu Ala Gly Asp Ala

TCG GAC AAC ATC CCC GGG CTT CCG GGC ATA GGG CCC AAA ACT GCC TCC CGT
Ser Asp Asn Ile Pro Gly Leu Pro Gly Ile Gly Pro Lys Thr Ala Ser Arg

CTG CTA CAG TCC CAC CAG AGC CTG GAG AAA TTG CTG GAG AGC AAG GAA TTT
Leu Leu Gln Ser His Gln Ser Leu Glu Lys Leu Leu Glu Ser Lys Glu Phe
```

```
TTT CCG GCC AAG CTG CGC GAA ACC TTA GAA AGG CAC AAG GAA GCG GTT
Phe Pro Ala Lys Leu Arg Glu Thr Leu Glu Arg His Lys Glu Ala Val

TTG GCC AAA CTG AAA CTC ATC CGC CGC GAT GTG CCG CTG GAA GAG GAG
Leu Ala Lys Leu Lys Leu Ile Arg Arg Asp Val Pro Leu Glu Glu Glu

ATC ATC CGG CCC TGG CCG GGA CCC AAC ATT TTA GCC ACG CTG GTC TTC
Ile Ile Arg Pro Trp Pro Gly Pro Asn Ile Leu Ala Thr Leu Val Phe

TCG CGC CTG GAA TTC CGC ACC TTG GCC AAG AGA TTC CTC GAG CTT CCC
Ser Arg Leu Glu Phe Arg Thr Leu Ala Lys Arg Phe Leu Glu Leu Pro

GAG GCA CGC CTC CTG TCC GCT AGT GGC CTT ACC CCC TCC GCT GTC CGC
Glu Ala Arg Leu Leu Ser Ala Ser Gly Leu Thr Pro Ser Ala Val Arg

AAG GTA GAA AGA CCC GAA GAA CTA GAA AGA CTG GGG GAA GAG CTC GGA
Lys Val Glu Arg Pro Glu Glu Leu Glu Arg Leu Gly Glu Glu Leu Gly

CAA GAA TTT GCG GCC CTG GLT TAC CCC CCC GTT CTT CGG CGC AAA GCC ACT
Gln Glu Phe Ala Ala Leu Ala Tyr Pro Pro Val Leu Arg Arg Lys Ala Thr
```

```
TCT TTC TTG GCT CTC TGT CTG GGA GAA AAG GTC TTC CTG GAA
Ser Phe Leu Ala Leu Cys Leu Gly Glu Lys Val Phe Leu Glu

GGG CCG GAG GTG CTC AAG AGC TTC TTC CGG CTG CTC GAA GAA AAG GGA GGT
Gly Pro Glu Val Leu Lys Ser Phe Phe Arg Leu Leu Glu Glu Lys Gly Gly

CTT GTC AGT ACC TAC GAC GCT AAA TCC TGC CTT CAC GCC CTG GAA CCT TAC
Leu Val Ser Thr Tyr Asp Ala Lys Ser Cys Leu His Ala Leu Glu Pro Tyr

GGC TTC AAG CCC GAA ATG ATC GGG TTT GAC GTC CTG CTG GCA GCC TAC CTG
Gly Phe Lys Pro Glu Met Ile Gly Phe Asp Val Leu Leu Ala Ala Tyr Leu

GTG AAC CCC GCC GCC AAC GAA CTG GGG GCG ATC GCC TTC GAG CAC GCG
Val Asn Pro Ala Ala Asn Glu Leu Gly Ala Ile Ala Phe Glu His Ala

GGC TTT ATG CTC TCC CCG GGA GCA GAG CTC CCG GAA AAA GCC CAG GCG ATC
Gly Phe Met Leu Ser Pro Gly Ala Glu Leu Pro Glu Lys Ala Gln Ala Ile

TAC CAG CTC ACC CCC ATC CTA AAA AGT AAG ATT AAG CTT CAG GAA CAG GAG
Tyr Gln Leu Thr Pro Ile Leu Lys Ser Lys Ile Lys Leu Gln Glu Gln Glu
```

```
CCA GAG CTC ATC GAC CCG GCC ACC GGG CGC CTG CAC ACC TTC TTG CAG
Pro Glu Leu Ile Asp Pro Ala Thr Gly Arg Leu His Thr Phe Leu Gln

GCA GGG ACG GCA ACG GGA AGA CTG GCC TCC GCC GAG CCC AAC CTG CAG AAC
Ala Gly Thr Ala Thr Gly Arg Leu Ala Ser Ala Glu Pro Asn Leu Gln Asn

ATT CCC GTA CGC GAT TCT CTG GGA AGG CGC ATC CGG CAG GCC TTC GTG GCT
Ile Pro Val Arg Asp Ser Leu Gly Arg Arg Ile Arg Gln Ala Phe Val Ala

GAG GGC CCC GAC TAC GTG CTA CTA AGC GCC GAC TAC TCC CAG CTG TGT GAG ATA GAG CTT
Glu Gly Pro Asp Tyr Val Leu Leu Ser Ala Asp Tyr Ser Gln Leu Cys Glu Ile Glu Leu

CGG GTC TTG GCC CAC CTT TCC GAA GAT CCG GGG CTG TGT GAG ATA GAG CTT
Arg Val Leu Ala His Leu Ser Glu Asp Pro Gly Leu Cys Glu Ile Glu Leu

AAA GGA GAA GAC ATT CAC GCC CGC ACG GCG GCC GAG ATC TTC GGC GTT TCT
Lys Gly Glu Asp Ile His Ala Arg Thr Ala Ala Glu Ile Phe Gly Val Ser

CCT CAG GAA GTG ACG CCG GAG ATG CGG GCC AAG GCC AAG GTG GTA AAC TTC
Pro Gln Glu Val Thr Pro Glu Met Arg Ala Lys Ala Lys Val Val Asn Phe
```

*FIGURE 1F*

```
GGG ATC GTT TAC GGC ATG AGC GAT TAC GGC CTT TCC CAG GAG CTC AAG ATC
Gly Ile Val Tyr Gly Met Ser Asp Tyr Gly Leu Ser Gln Glu Leu Lys Ile

GAG CCC GCC GAG GCG CAC GAG TAT ATA GAA CGG TAC TTC CGG CGC TAT CCG
Glu Pro Gly Glu Ala His Glu Tyr Ile Glu Arg Tyr Phe Arg Arg Tyr Pro

CGC GTG AAG CAG TTC ATC GAG CGG GTG ATC GCC CAG GCC CGA GAG AAG GGC
Arg Val Lys Gln Phe Ile Glu Arg Val Ile Ala Gln Ala Arg Glu Lys Gly

TAC GTG ACC ACT ATT CTC AAC CGC CGC TAC ATC CCT GAA ATA CTG AGC
Tyr Val Thr Thr Ile Leu Asn Arg Arg Tyr Ile Pro Glu Ile Leu Ser

AGC AAC CGC CAG CGT CAG CTG GGG GAG CGC CTG GCC ATC AAC ACC ACC
Ser Asn Arg Gln Arg Gln Leu Gly Glu Arg Leu Ala Ile Asn Thr Thr

ATT CAA GGA AGT GCG GCC GAT CTT ATA AAA AAG GCC ATG GTG GAC ATC CAC
Ile Gln Gly Ser Ala Ala Asp Leu Ile Lys Lys Ala Met Val Asp Ile His

CGG CAA CTG AAA GGG CAA GGA TTT AAA TGC CGG ATG ATC CTC CAG GTG CAC
Arg Gln Leu Lys Gly Gln Gly Phe Lys Cys Arg Met Ile Leu Gln Val His
```

*FIGURE 1G*

```
GAC GAA CTC CTC TCC GAG GTG CCT AAA GAA GAA CTG GAA AAG GTG GCA CCT
Asp Glu Leu Leu Ser Glu Val Pro Lys Glu Glu Leu Glu Lys Val Ala Pro

ATA ATA AAA AGC ACC ATG GAG CAA GCC TTA CCT TTT AAG GTT CCC ATA AAG
Ile Ile Lys Ser Thr Met Glu Gln Ala Leu Pro Phe Lys Val Pro Ile Lys

GCC AAC CTC AAG GTA GGG CCT AAC TGG CAA GAC ATG GAA GAG TAC GAG GTG
Ala Asn Leu Lys Val Gly Pro Asn Trp Gln Asp Met Glu Glu Tyr Glu Val
2602
GAA TGA     Glu End
```

*FIGURE 1H*

```
(SEQ ID NO:3) ATG ACT GAA GTT GTA TTC ACG GTT TTA GAC TCT AGC TAC GAG GTT GGT
(SEQ ID NO:4) Met Thr Glu Val Val Phe Thr Val Leu Asp Ser Ser Tyr Glu Val Gly

AAA GAG CCT CAG GTA ATC ATA TGG GGT ATT GCT GAG AAC GGC GAG AGG GTA
Lys Glu Pro Gln Val Ile Ile Trp Gly Ile Ala Glu Asn Gly Glu Arg Val

GTC CTC ATT GAC AGG TCT TTT CGC CCA TAC TTC TAT GCG CTG CTT GCA CCG
Val Leu Ile Asp Arg Ser Phe Arg Pro Tyr Phe Tyr Ala Leu Leu Ala Pro

GGC GCC GAT CCT AAG CAG GTA GCA CAA CGT ATT CGT GCA TTG AGT AGG CCA
Gly Ala Asp Pro Lys Gln Val Ala Gln Arg Ile Arg Ala Leu Ser Arg Pro

AAG AGC CCG ATT ATA GGT GTA GAG GAT GAC AAG AGG AAG TAC TTC GGG AGG
Lys Ser Pro Ile Ile Gly Val Glu Asp Asp Lys Arg Lys Tyr Phe Gly Arg

CCG CGT AGG GTC TTA CGT ATT CGC ACC GTG CTA CCC GAG GCT GTT AGG GAG
Pro Arg Arg Val Leu Arg Ile Arg Thr Val Leu Pro Glu Ala Val Arg Glu

TAT CGC GAA CTC GTA AAG AAC GTT GAT GGT GTT GAG GAT GTT CTA GAG GCG
Tyr Arg Glu Leu Val Lys Asn Val Asp Gly Val Glu Asp Val Leu Glu Ala
```

| | | | | | | | | | | | | | | | | |
|---|---|---|---|---|---|---|---|---|---|---|---|---|---|---|---|---|
| GAT | ATA | CGC | TTC | GCT | ATG | CGC | TAT | CTC | ATA | GAT | CAC | GAT | CTA | TTT | CCT | TTC |
| Asp | Ile | Arg | Phe | Ala | Met | Arg | Tyr | Leu | Ile | Asp | His | Asp | Leu | Phe | Pro | Phe |
| ACC | TGG | TAC | CGT | GTA | GAG | GCT | GAG | CCC | CTC | GAG | AAC | AAG | ATG | GGC | TTC | CGT |
| Thr | Trp | Tyr | Arg | Val | Glu | Ala | Glu | Pro | Leu | Glu | Asn | Lys | Met | Gly | Phe | Arg |
| GTC | GAC | AAG | GTA | TAC | CTG | GTT | AAG | AGC | AGG | CCG | GAG | CCA | CTT | TAT | GGT | GAG |
| Val | Asp | Lys | Val | Tyr | Leu | Val | Lys | Ser | Arg | Pro | Glu | Pro | Leu | Tyr | Gly | Glu |
| GCT | CTC | GCA | CCA | ACC | AAG | CTT | CCC | GAT | CTT | AGG | ATA | CTC | GCG | TTC | GAT | ATT |
| Ala | Leu | Ala | Pro | Thr | Lys | Leu | Pro | Asp | Leu | Arg | Ile | leu | Ala | Phe | Asp | Ile |
| GAA | GTT | TAT | AGC | AAG | CAA | GGG | TCG | CCG | CGT | CCA | GAG | CGC | GAT | CCT | GTA | ATA |
| Glu | Val | Tyr | Ser | Lys | Gln | Gly | Ser | Pro | Arg | Pro | Glu | Arg | Asp | Pro | Val | Ile |
| GTG | ATA | GCT | GTG | AAG | ACT | GAC | GAT | GGC | GAT | GAG | GTG | CTA | TTC | ATT | GCA | GAG |
| Val | Ile | Ala | Val | Lys | Thr | Asp | Asp | Gly | Asp | Glu | Val | Leu | Phe | Ile | Ala | Glu |
| GGC | AAA | GAC | GAT | CGA | AAA | CCG | ATA | CGC | GAG | TTT | GTA | GAG | TAC | GTG | AAG | AGG |
| Gly | Lys | Asp | Asp | Arg | Lys | Pro | Ile | Arg | Glu | Phe | Val | Glu | Tyr | Val | Lys | Arg |

```
TAT GAC CCC GAC ATA ATA GTC GGT TAT AAC AAT CAT TTC GAT TGG CCT
Tyr Asp Pro Asp Ile Ile Val Gly Tyr Asn Asn His Phe Asp Trp Pro

TAT CTT TTG AGG CGC GCC CGC ATC CTA GGC ATA AAG CTT GAT GTG ACT AGA
Tyr Leu Leu Arg Arg Ala Arg Ile Leu Gly Ile Lys Leu Asp Val Thr Arg

AGA GTT GGC GCC GAG CCC ACC ACT AGC GTA CAT GGG CAC GTC TCT GTC CCT
Arg Val Gly Ala Glu Pro Thr Thr Ser Val His Gly His Val Ser Val Pro

GGC AGG CTT AAC GTA GAT CTG TAC GAC TAT GCC GAA GAG ATG CCA GAG ATC
Gly Arg Leu Asn Val Asp Leu Tyr Asp Tyr Ala Glu Glu Met Pro Glu Ile

AAG ATA AAG AGT CTC GAG GTT ATC ATC GCA GAG TAT CTA GGC GTG ATG AAG AAG
Lys Ile Lys Ser Leu Glu Val Ile Ile Ala Glu Tyr Leu Gly Val Met Lys Lys

AGT GAA CGC GTT ATC AAT TGG TGG GAG ATT CCA GAC TAT TGG GAC GAC
Ser Glu Arg Val Ile Asn Trp Trp Glu Ile Pro Asp Tyr Trp Asp Asp

CCG AAG AGA CCA CTA TTA CTG CAA TAC GCG CTC GAT GTC CGC GCT
Pro Lys Arg Pro Leu Leu Leu Gln Tyr Ala Arg Asp Val Arg Ala
```

*FIGURE 2C*

ACT TAC GGC TTA GCC GAG AAG ATA TTG CCG TTT GCT ATC CAG TTG TCG TAC
Thr Tyr Gly Leu Ala Glu Lys Ile Leu Pro Phe Ala Ile Gln Leu Ser Tyr

GTA ACA GGT CTC CCA CTA GAC CAG GTA GGT GCG ATG AGT GTT GGC TTT CGA
Val Thr Gly Leu Pro Leu Asp Gln Val Gly Ala Met Ser Val Gly Phe Arg

CTT GAA TGG TAC CTG ATA CGC GCG TTT AAG ATG AAA GAG CTT GTG CCG
Leu Glu Trp Tyr Leu Ile Arg Ala Ala Phe Lys Met Lys Glu Leu Val Pro

AAC CGC GTT GAG CGC CCA GAA GAG ACT TAC CGT GGC GCT ATA GTT CTT GAG
Asn Arg Val Glu Arg Pro Glu Glu Thr Tyr Arg Gly Ala Ile Val Leu Glu

CCG TTG AGA GGC GTG CAC GAG AAT ATA GCC GTA CTC GAC TTT AGC TCG ATG
Pro Leu Arg Gly Val His Glu Asn Ile Ala Val Leu Asp Phe Ser Ser Met

TAC CCA AAC ATC ATG ATA AAG TAC AAT GTT GGT CCT CAG ACG CTT GTG AGG
Tyr Pro Asn Ile Met Ile Lys Tyr Asn Val Gly Pro Gln Thr Leu Val Arg

CCT GGT GAA AAG TGT GGC GAG TGT GGT TGC TGG GAG GCC CCG GAG GTC AAG
Pro Gly Glu Lys Cys Gly Glu Cys Gly Cys Trp Gly Ala Pro Glu Val Lys

*FIGURE 2D*

CAC AGG TTC CGT AGG TGT CCG CCC GGC TTC TTC AAG ACA GTT CTT GAG AGG
His Arg Phe Arg Arg Cys Pro Pro Gly Phe Phe Lys Thr Val Leu Glu Arg

CTG TTA GAG CTT CGT AAG CGT GTG GCT GAA ATG AAG TAT CCT CCG
Leu Leu Glu Leu Arg Lys Arg Val Ala Glu Met Lys Tyr Pro Pro

GAT AGC CCA GAA TAT CGA CTG TTG GAT GAA AGG CAG AAG CGC TTC AAG GTT
Asp Ser Pro Glu Tyr Arg Leu Leu Asp Glu Arg Gln Lys Arg Phe Lys Val

CTT GCA AAC GCT AGT TAC GGC GAC ATG GGT TGG AGC GGC GCT AGG TGG TAT
Leu Ala Asn Ala Ser Tyr Gly Asp Met Gly Trp Ser Gly Ala Arg Trp Tyr

TGC AGG GAG TGC GCA AAG GCT GTC ACG GCT TGG GGT CAC CTC ATA CGC
Cys Arg Glu Cys Ala Lys Ala Val Thr Ala Trp Gly His Leu Ile Arg

ACC GCC ATC AAG ATA GCT CGT AAA CTA GGC CTC AAG GTG ATC TAC GGT GAC
Thr Ala Ile Lys Ile Ala Arg Lys Leu Gly Leu Lys Val Ile Tyr Gly Asp

ACA GAT TCG CTC TTC GTG ACC TAT GAT CCG GAG AAG GTG GAA AAT TTC ATC
Thr Asp Ser Leu Phe Val Thr Tyr Asp Pro Glu Lys Val Glu Asn Phe Ile

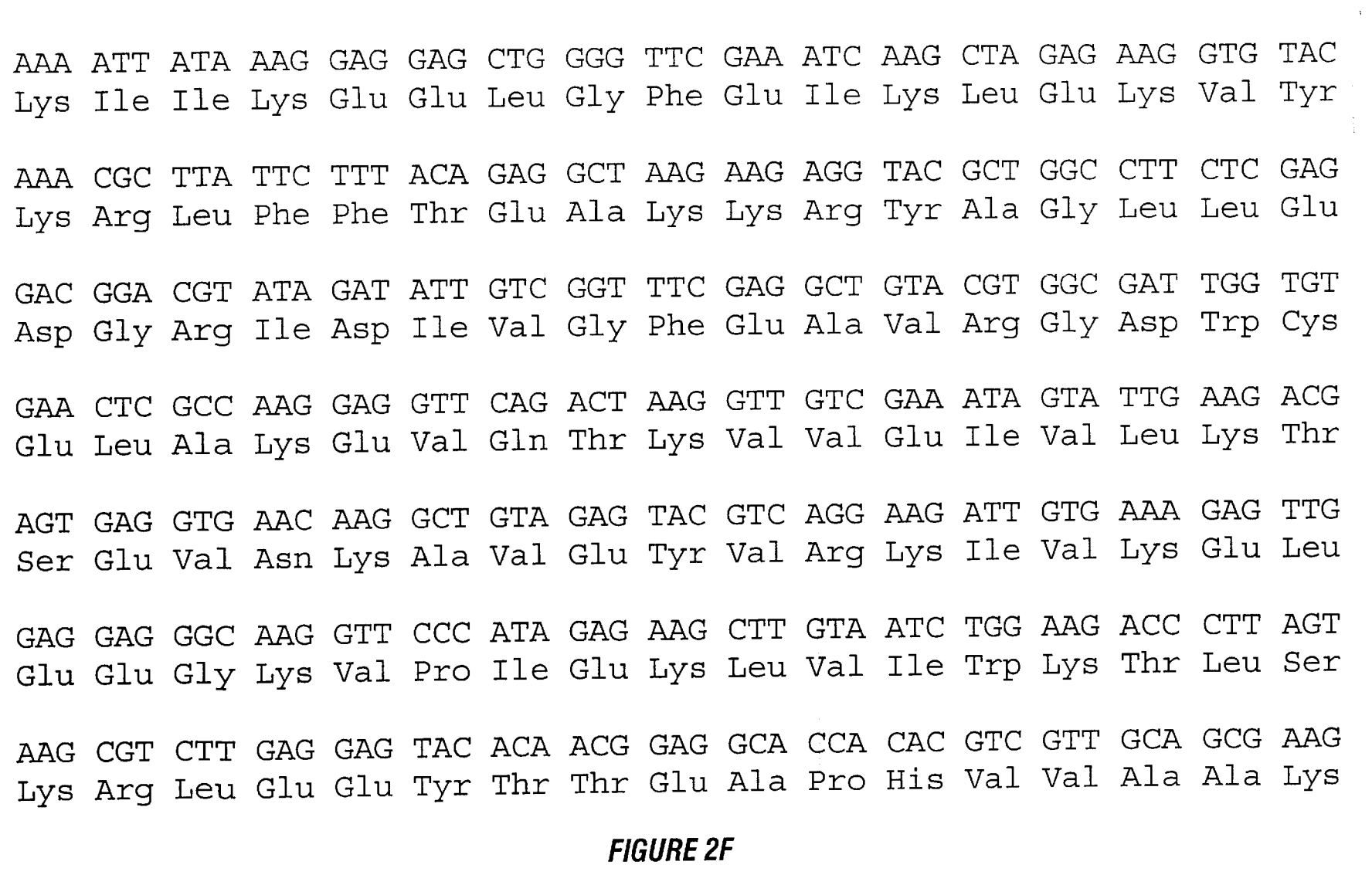

```
AGG ATG CTG TCA GCA GGC TAC CGG GTA AGC CCA GGC GAC AAG ATA GGG TAT
Arg Met Leu Ser Ala Gly Tyr Arg Val Ser Pro Gly Asp Lys Ile Gly Tyr

GTA ATA GTG AAG GGT GGT GGC GGC CGT ATC AGT CAA AGA GCA TGG CCA TAC TTC
Val Ile Val Lys Gly Gly Gly Arg Ile Ser Gln Arg Ala Trp Pro Tyr Phe

ATG GTC AAG GAT CCT AGC CAG ATA GAC GTG ACC TAC TAT GTT GAC CAC CAA
Met Val Lys Asp Pro Ser Gln Ile Asp Val Thr Tyr Tyr Val Asp His Gln

ATC ATC CCG GCT GCA TTG AGA ATA CTG GGC TAC TTT GGC ATC ACC GAG AAG
Ile Ile Pro Ala Ala Leu Arg Ile Leu Gly Tyr Phe Gly Ile Thr Glu Lys

AAG CTG AAA GCA AGT GCA ACT GGG CAG AAG ACT CTC TTC GAC TTT CTA GCC
Lys Leu Lys Ala Ser Ala Thr Gly Gln Lys Thr Leu Phe Asp Phe Leu Ala

2412

AAG AAG AGC AAG TAA
Lys Lys Ser Lys End
```

*FIGURE 2G*

(SEQ ID NO:5) ATG ATA AAG GTC AAG GGC TGG CTG CTC GAT GCA GAT TAT ATC ACC GAA AAC
(SEQ ID NO:6) Met Ile Lys Val Lys Gly Trp Leu Leu Asp Ala Asp Tyr Ile Thr Glu Asn

GAT CGA GCC GTT ATA AGG CTA TGG TGT AAG GAT GAG GAA GGA ATA TTT ATC
Asp Arg Ala Val Ile Arg Leu Trp Cys Lys Asp Glu Glu Gly Ile Phe Ile

GCA TAC GAT CAC TCA TTC CAG CCC TAC TTT TAC GCA CTC AAA GAA GAG GGT
Ala Tyr Asp His Ser Phe Gln Pro Tyr Phe Tyr Ala Leu Lys Glu Glu Gly

ATC ACT GCC GAA GAT ATA GTG AAA GTT CAA ACG AAA AAT CTT GGT AGG GAG
Ile Thr Ala Glu Asp Ile Val Lys Val Gln Thr Lys Asn Leu Gly Arg Glu

ATT ACG CCG TTA AAA GTT GAG ACC ACA GCC AAA AAT CTT GGT AGG GAG
Ile Thr Pro Leu Lys Val Glu Thr Thr Ala Lys Asn Leu Gly Arg Glu

GTT GAA GTT TTC AAG ATA TAT GCA AGA CAC CCT CAG CAC GTC CCC AAA CTT
Val Glu Val Phe Lys Ile Tyr Ala Arg His Pro Gln His Val Pro Lys Leu

CGT GAG GTT GTT TCG CAG TAT CTG GAG ATT AGG GAG GCA GAC ATA CCT TTT
Arg Glu Val Val Ser Gln Tyr Leu Glu Ile Arg Glu Ala Asp Ile Pro Phe

*FIGURE 3A*

```
GCC TAT CGA TAC CTC ATA GAT AAA AAT CTT GCG TGT ATG GAT GGA GTT GTA
Ala Tyr Arg Tyr Leu Ile Asp Lys Asn Leu Ala Cys Met Asp Gly Val Val

ATT GAA GGC GTT GAA AGA CGT GAG AAG GGG TTG AGA TGT TAC GAA ATC AAG
Ile Glu Gly Val Glu Arg Arg Glu Lys Gly Leu Arg Cys Tyr Glu Ile Lys

AGA ATA GAA AGA GAT TCC AGA CAG GAT TTT CCC GAA CTC AAG GTT ATG GCG
Arg Ile Glu Arg Asp Ser Arg Gln Asp Phe Pro Glu Leu Lys Val Met Ala

TTT GAT TGC GAA ATG CTC TCA GAG GTT GGT ATG CCC GAT CCA GAG AAA GAT
Phe Asp Cys Glu Met Leu Ser Glu Val Gly Met Pro Asp Pro Glu Lys Asp

CCT ATC ATA GTC ATA ATT AAA TCG ATT CTT ACC AGA TTT GTC AAG ATA ATT
Pro Ile Ile Val Ile Ile Lys Ser Ile Leu Thr Arg Phe Val Lys Ile Ile

GGT GAT AAC GAG AGA GAA TTG CTT ACC AGA TAT AAT CAG GAC AGC TTT GAC
Gly Asp Asn Glu Arg Glu Leu Leu Thr Arg Tyr Asn Gln Asp Ser Phe Asp

ATT GAT CCC GAC ATT ATA GTT GGA TAC AAT CAG GAC AGC TTT GAC TGG CCC
Ile Asp Pro Asp Ile Ile Val Gly Tyr Asn Gln Asp Ser Phe Asp Trp Pro
```

*FIGURE 3B*

| TAT | ATC | AAG | AGA | GCT | GAG | AAA | CTG | AGG | GTT | AAG | CTT | GAC | ATC | GGA | AGA |
|-----|-----|-----|-----|-----|-----|-----|-----|-----|-----|-----|-----|-----|-----|-----|-----|
| Tyr | Ile | Lys | Arg | Ala | Glu | Lys | Leu | Arg | Val | Lys | Leu | Asp | Ile | Gly | Arg |

| GAT | AGA | AGC | GAA | CTG | GCT | ATC | AGG | GGA | GGA | AGA | CCA | AAG | ATT | GCT | GGC | AGG |
|-----|-----|-----|-----|-----|-----|-----|-----|-----|-----|-----|-----|-----|-----|-----|-----|-----|
| Asp | Arg | Ser | Glu | Leu | Ala | Ile | Arg | Gly | Gly | Arg | Pro | Lys | Ile | Ala | Gly | Arg |

| TTG | AAC | GTG | GAT | CTC | TAT | GAT | ATT | GCA | ATG | AGG | AGT | CTC | GAT | GTA | AAG | GTG |
|-----|-----|-----|-----|-----|-----|-----|-----|-----|-----|-----|-----|-----|-----|-----|-----|-----|
| Leu | Asn | Val | Asp | Leu | Tyr | Asp | Ile | Ala | Met | Arg | Ser | Leu | Asp | Val | Lys | Val |

| AAG | AAG | CTC | GAA | AAC | GTT | GCA | GAG | TTT | CTG | GGT | AAG | AAA | ATA | GAG | CTT | CGA |
|-----|-----|-----|-----|-----|-----|-----|-----|-----|-----|-----|-----|-----|-----|-----|-----|-----|
| Lys | Lys | Leu | Glu | Asn | Val | Ala | Glu | Phe | Leu | Gly | Lys | Lys | Ile | Glu | leu | Ala |

| GAT | ATT | GAA | GCG | AAG | GAT | ATC | TAC | AAG | CAC | TGG | ACA | TCG | GGC | GAC | AGG | GAA |
|-----|-----|-----|-----|-----|-----|-----|-----|-----|-----|-----|-----|-----|-----|-----|-----|-----|
| Asp | Ile | Glu | Ala | Lys | Asp | Ile | Tyr | Lys | His | Trp | Thr | Ser | Gly | Asp | Arg | Glu |

| AGC | GTA | ATC | AAA | TAC | TCC | CGG | CAG | GAC | ATC | CTG | CAC | ACG | TAC | TTC | ATA | GCT |
|-----|-----|-----|-----|-----|-----|-----|-----|-----|-----|-----|-----|-----|-----|-----|-----|-----|
| Ser | Val | Ile | Lys | Tyr | Ser | Arg | Gln | Asp | Ile | Leu | His | Thr | Tyr | Phe | Ile | Ala |

| GAA | GAA | TTG | CTG | CCA | ATG | CAT | TAC | GAA | CTT | TCC | AGA | ATG | ATA | CGC | ATA | CCT |
|-----|-----|-----|-----|-----|-----|-----|-----|-----|-----|-----|-----|-----|-----|-----|-----|-----|
| Glu | Glu | Leu | Leu | Pro | Met | His | Tyr | Glu | Leu | Ser | Arg | Met | Ile | Arg | Ile | Pro |

*FIGURE 3C*

CTC GAT GAT GTG ACA AGG AGC GGG AGA GGT AAG CAG GTT GAG TGG CTG CTG
Leu Asp Asp Val Thr Arg Ser Gly Arg Gly Lys Gln Val Glu Trp Leu Leu

TTA AGC GAA GCA CAC AAA CTT GGC GAA CTT GCA CCC ACC CCC AGA GAG ATG
Leu Ser Glu Ala His Lys Leu Gly Glu Leu Ala Pro Thr Pro Arg Glu Met

GCC GAC AGC TAT GAA GGA GCA TTC GTG CTC GAG CCC GCA AGA GGA TTG CAT
Ala Asp Ser Tyr Glu Gly Ala Phe Val Leu Glu Pro Ala Arg Gly Leu His

GAG AAC GTA ATC TGC CTG GAC TTT GCG TCC ATG TAT CCC TCA ATA ATG ATT
Glu Asn Val Ile Cys Leu Asp Phe Ala Ser Met Tyr Pro Ser Ile Met Ile

TCA TAC AAC ATC AGC CCC GAC ACG CTT GTA ATA GGC AAA TGC GAC GAT TGC
Ser Tyr Asn Ile Ser Pro Asp Thr Leu Val Ile Gly Lys Cys Asp Asp Cys

AAT GTA GCG CCG GAG GTG GGG CAC AAA TTC AGG AAA CAT CCT GAT GGT TTT
Asn Val Ala Pro Glu Val Gly His Lys Phe Arg Lys His Pro Asp Gly Phe

TTC AAA AGA ATA CTC AAA ATG CTG ATT GAG AAA AGA AGA GAA ATA AAG AAG
Phe Lys Arg Ile Leu Lys Met Leu Ile Glu Lys Arg Arg Glu Ile Lys Lys

*FIGURE 3D*

```
GTT ATG AAA ACA CTT GAC TAC AAC TCG CCA GAA TAC AAG CTG CTC GAT ATA
Val Met Lys Thr Leu Asp Tyr Asn Ser Pro Glu Tyr Lys Leu Leu Asp Ile

AAG CAG GCA ACG CTG AAA GTT CTT ACA AAC TCG TTT TAC GGT TAT ACT GGG
Lys Gln Ala Thr Leu Lys Val Leu Thr Asn Ser Phe Tyr Gly Tyr Thr Gly

TGG AGT CTT GCG AGA TGG TAC TGC AAG GAG TGC GCT GAA GCT ACA ACG GCA
Trp Ser Leu Ala Arg Trp Tyr Cys Lys Glu Cys Ala Glu Ala Thr Thr Ala

TGG GGC AGA CAC TTT ATC AAA ACA TCT GCA AGA ATT GCG AAA GAG CTT GGA
Trp Gly Arg His Phe Ile Lys Thr Ser Ala Arg Ile Ala Lys Glu Leu Gly

TTT GAA GTG CTA TAT GGG GAT ACA GAT AGC ATC TTT GTT AAA AAA GAT GGA
Phe Glu Val Leu Tyr Gly Asp Thr Asp Ser Ile Phe Val Lys Lys Asp Gly

TTG AGC CTG GAA GAG CTC AAA GAA GTT AAA GAA AAG CTC ATA GGT AAA CTT
Leu Ser Leu Glu Glu Leu Lys Glu Val Lys Lys Leu Ile Gly Lys Leu

TCG GAA GAG ATG CCA ATA CAA ATA GAT GAA TAC TAC GAG ACA ATA
Ser Glu Glu Met Pro Ile Gln Ile Asp Glu Tyr Tyr Glu Thr Ile
```

*FIGURE 3E*

```
TTC TTC GTT GAA AAG AAA AGG TAT GCT GGA TTG ACA CAG GAT GGA AGA ATA
Phe Phe Val Glu Lys Lys Arg Tyr Ala Gly Leu Thr Gln Asp Gly Arg Ile

ATT GTA AAG GGT CTT GAA GTC AGA GGC GAC TGG TGC GAG CTT GCA AAG
Ile Val Lys Gly Leu Glu Val Arg Arg Gly Asp Trp Cys Glu Leu Ala Lys

AAG ATA CAG AAA GGT GTA ATA GAA ATT CTG AAG GAA AAG AAT CCT GAA
Lys Ile Gln Lys Gly Val Ile Glu Ile Leu Lys Glu Lys Asn Pro Glu

AAA GCT GCT GAG TAT GTG AAA GGA GTC ATA CAG GAG ATA AAG GCA AAA
Lys Ala Ala Glu Tyr Val Lys Gly Val Ile Gln Glu Ile Lys Ala Lys

ATT CCG CTT GAA GAT TAT ATC ATC TAC AAG GGA TTG ACG AGA AAA CCA TCA
Ile Pro Leu Glu Asp Tyr Ile Ile Tyr Lys Gly Leu Thr Arg Lys Pro Ser

AAG TAC GAG AGT ATG CAG GCT CAC GTA AAA GCT GCC ATG AAG CGC GCA AAG
Lys Tyr Glu Ser Met Gln Ala His Val Lys Ala Ala Met Lys Arg Ala Lys

AGA GGA ATA GTA TAC ACA ATC GGC TCA AAG GTT GGT TTT GTC GTT ACA AAA
Arg Gly Ile Val Tyr Thr Ile Gly Ser Lys Val Gly Phe Val Val Thr Lys
```

*FIGURE 3F*

```
GGT GTG GGG AAC ATA GGT GAT AGG GCT TTT CCA TCT GAT CTG ATA GAG GAC
Gly Val Gly Asn Ile Gly Asp Arg Ala Phe Pro Ser Asp Leu Ile Glu Asp

TTT GAC GGT GAA GTG ATC ACA GAT CTT GAC GGA AAC AAG TAC AAG ATC GAC
Phe Asp Gly Glu Val Ile Thr Asp Leu Asp Gly Asn Lys Tyr Lys Ile Asp

AAG GAA TAC TAT ATA GAC CAT CAG GTA CTG CCA TCG GTT CTT CGA ATT CTC
Lys Glu Tyr Tyr Ile Asp His Gln Val Leu Pro Ser Val Leu Arg Ile Leu

GAG AGG TTC GGA TAC ACC GAG GCA CAG CTA AAA GGT GCT GCG GAG CAG CAA
Glu Arg Phe Gly Tyr Thr Glu Ala Gln Leu Lys Gly Ala Ala Glu Gln Gln

ACG CTA GAT GCT TTC TGG TAA
Thr Leu Asp Ala Phe Trp End
```

*FIGURE 3G*

(SEQ ID NO:7) ATG AGT ATA ATG GCC AGA CAG CTT ACC CTT GCT GAC TTC TCT GGG ATC AAG
(SEQ ID NO:8)     Met Ser Ile Met Ala Arg Gln Leu Thr Leu Ala Asp Phe Ser Gly Ile Lys

AGA GAG GAA CCA GTT AAA CAG GAA GAA AAG ACG CAG GAG GAA GAG AGG CCT
Arg Glu Glu Pro Val Lys Gln Glu Glu Lys Thr Gln Glu Glu Glu Arg Pro

CTG GAA AGG CCA GCG AGG CTA AGA AAG GAC ACA GTT AAA CAG GCG CAG GAG
Leu Glu Arg Pro Ala Arg Leu Arg Lys Asp Thr Val Lys Gln Ala Gln Glu

GAG AGA AAG TAC TTT CTT CTC TCC GTA GAC TAT GAT CCT GAA ACG GGT AAG
Glu Arg Lys Tyr Phe Leu Leu Ser Val Asp Tyr Asp Pro Glu Thr Gly Lys

GCT GTC TGC AAG CTT TAT GAT CCT GAA ACG GGT GAG CTA CAC GTC CTT TAC
Ala Val Cys Lys Leu Tyr Asp Pro Gly Thr Gly Glu Leu His Val Leu Tyr

GAC AGC ACG GGT CAC AAG TCA TAC TTC CTT GTG GAT TTA GAG CCA GAT CAG
Asp Ser Thr Gly His Lys Ser Tyr Phe Leu Val Asp Leu Glu Pro Asp Gln

ATC CAA AAA ATT GTT AAG GAT GAG TCC TTT GTT AGG CTT GAG
Ile Gln Lys Ile Val Lys Asp Glu Ser Phe Val Arg Leu Glu

*FIGURE 4A*

```
AAG ACC ACT AAA ATA GAC CCC TAC ACT TGG AAA CCT ATT AAC CTA ACC AAG
Lys Thr Thr Lys Ile Asp Pro Tyr Thr Trp Lys Pro Ile Asn Leu Thr Lys

ATT GTG GTG AAT GAC CCC CTC GCT GTG AGA CGC CTA AGA GAA TAT GTC CCA
Ile Val Val Asn Asp Pro Leu Ala Val Arg Arg Leu Arg Glu Tyr Val Pro

AGG GCC TAT GAA GCT CAT ATA AAA TAT TTT AAC AAT TAC ATT TAC GAT TTC
Arg Ala Tyr Glu Ala His Ile Lys Tyr Phe Asn Asn Tyr Ile Tyr Asp Phe

AGC CTC ATA CCA GGG ATG CCC TAC GTG AAG GTA AAG GGG AAG CTA GTC CCC
Ser Leu Ile Pro Gly Met Pro Tyr Val Lys Val Lys Gly Lys Leu Val Pro

CTT AAG CCG GAG GTT GAC GTC AAA GAG GTA GAC TGG GCT CCC CTC TTT GAG TCC
Leu Lys Pro Glu Val Asp Val Lys Glu Val Lys Glu Ala Phe Lys Asp Ala

GAC CAG ATA GCT CAA GAG ATG GCG CTA GAC TGG GCT CCC GCT CCC CTC TTT GAG TCC
Asp Gln Ile Ala Gln Glu Met Ala Leu Asp Trp Ala Pro Leu Phe Glu Ser

GAG ATT CCG TCG GTG AAG AGG GTC GCA ATA GAT ATA GAG GTT TAT ACT CCC
Glu Ile Pro Ser Val Lys Arg Val Ala Ile Asp Ile Glu Val Tyr Thr Pro
```

*FIGURE 4B*

```
ATG ATG GGT AGG GTA CCG CAT CCA GTA AAG GCC GAG TAC CCC GTG ATA AGC
Met Met Gly Arg Val Pro Asp Pro Val Lys Ala Glu Tyr Pro Val Ile Ser

GTA GCC CTA GCA GGG AGC GAT GGC CTG AAA CTG CTA GTC CTT GAT AGG
Val Ala leu Ala Gly Ser Asp Gly Leu Lys Leu Leu Val Leu Asp Arg GGA GAT AGT CCG ATT CAA AGT AAG GAT ATC AAG GTT GAG GTC TTC CGC ACA
Gly Asp Ser Pro Ile Gln Ser lys Asp Ile Lys Val Glu Val Phe Arg Thr GAG AGG GAG CTT CTC TCC AGG TTG TTT GAC ATT CTT AAG GAA TAT CCC ATG
Glu Arg Glu Leu Leu Ser Arg Leu Phe Asp Ile Leu Lys Glu Tyr Pro Met GTT CTG ACC TTT AAC GGA GAC GAT ATC GAT TTC GAT CCA TAC CTG ATC TTC ACA
Val Leu Thr Phe Asn Gly Asp Asp Ile Asp Phe Asp Pro Tyr Leu Ile Phe Arg GGT TTC AAG CTC GGG TTA CTA CAG GAT GAG ATA CCC TTC GAG ATC TCT AGT
Gly Phe Lys Leu Gly Leu Leu Gln Asp Glu Ile Pro Phe Glu Ile Ser Ser TTT GGC AGG AAA CCT GAC GCG AAG TTC AGA TAT GGA TTT CAC ATA GAT TTG
Phe Gly Arg Lys Pro Asp Ala Lys Phe Arg Tyr Gly Phe His Ile Asp Leu
```

FIGURE 4C

```
TAC AGG TTC TTC AAC AAG GCG GTC AGG AAC TAT GCA TTT GAG GGG AAG
Tyr Arg Phe Phe Asn Lys Ala Val Arg Asn Tyr Ala Phe Glu Gly Lys

TAC TCA GAG TAC AAC CTT GAC ACC GTA GCC CAG GCA CTC TTG GGT CTC TCC
Tyr Ser Glu Tyr Asn Leu Asp Thr Val Ala Gln Ala Leu Leu Gly Leu Ser

AAG GTC AAG TTG GAC GAG TCC ATT AGC GAC CTA AAC ATG TCT AAA CTC GTG
Lys Val Lys Leu Asp Glu Ser Ile Ser Asp Leu Asn Met Ser Lys Leu Val

GAG TAC AAC TAC AGG GAC TCG GAG ATG ACG CTG AAG TTG ACC ACG TTC AAC
Glu Tyr Asn Tyr Arg Asp Ser Glu Ile Thr Leu Lys Leu Thr Thr Phe Asn

AAC GAA CTA GTA TGG AAG TTG ATT GTA CTC TTC TCC AGA ATT TCC AAG CTT
Asn Glu Leu Val Trp Lys Leu Ile Val Leu Phe Ser Arg Ile Ser Lys Leu

GGT ATA GAG GAG CTA ACT AGG ACA GAG ATA TCA GCC TGG GTA AAG AAC CTG
Gly Ile Glu Glu Leu Thr Arg Thr Glu Ile Ser Ala Trp Val Lys Asn Leu

TAC TAC TGG GAA CAT AGG AAA AGG AAC TGG TTA ATC CCC CTC AAG GAG GAA
Tyr Tyr Trp Glu His Arg Lys Arg Asn Trp Leu Ile Pro Leu Lys Glu Glu
```

*FIGURE 4D*

```
ATC CTT GAA CGC TCC TCT GGG TTG AAG ACA GCT ATT ATC AAG GGA AAG
Ile Leu Glu Arg Ser Ser Gly Leu Lys Thr Ala Ile Ile Lys Gly Lys

GGA TAC AAG GGC GCA GTG GAC CCA CCT GCC GTT GGG GTT TAC TTT GAC
Gly Tyr Lys Gly Ala Val Asp Pro Pro Val Gly Val Tyr Phe Asp

GTA GTT GTT CTG GAC TTC GCC TCA CTG TAT CCC TCC ATC AGG AAC TGG
Val Val Val Leu Asp Phe Ala Ser Leu Tyr Pro Ser Ile Ile Arg Asn Trp

AAC CTC AGT TAT GAA ACC GTT GAT GTG AAG GAA TGT AAC AAG AAA AGG GAT
Asn Leu Ser Tyr Glu Thr Val Asp Val Lys Glu Cys Asn Lys Lys Arg Asp

ATA AGG GAT GAG AGT GGG GCG AAA ATC CAT GAG GTG TGC GTG GAC AGG CCC
Ile Arg Asp Glu Ser Gly Ala Lys Ile His Glu Val Cys Val Asp Arg Pro

GGG ATT ACT GCA GTG GTA ACT GGC TTA CTT AGG GAC TTC AGG GTC AAA ATT
Gly Ile Thr Ala Val Val Thr Gly Leu Leu Arg Asp Phe Arg Val Lys Ile

TAC AAG AAA GGG AAA CAG AGC AAC ATA GAC GAG GAG AGA AAG ATG TTG
Tyr Lys Lys Gly Lys Gln Ser Asn Ile Asp Glu Glu Arg Lys Met Leu
```

*FIGURE 4E*

```
TAC GAC GTG GTA CAG AGG GGC ATG AAG GTG TTC ATT AAT GCG ACC TAT GGC
Tyr Asp Val Val Gln Arg Gly Met Lys Val Phe Ile Asn Ala Thr Tyr Gly

GTC TTC GGT GCG GAG ACC TTC CCC TTG TAC GCC CCA GCA GTT GCA GAG AGC
Val Phe Gly Ala Glu Thr Phe Pro Leu Tyr Ala Pro Ala Val Ala Glu Ser

GTT ACA GCC CTA GGT AGG TAC GTA ATC ACG TCC ACC AAG GAA ATG GCT AAC
Val Thr Ala Leu Gly Arg Tyr Val Ile Thr Ser Thr Lys Glu Met Ala Asn

AAG CTT GGG CTG AAG GTT GTG TAC GGG GAT ACG GAC TCG CTC TTC ATT CAC
Lys Leu Gly Leu Lys Val Val Tyr Gly Asp Thr Asp Ser Leu Phe Ile His

CAG CCT GAT AAG AAG AAG CTG GAG GAA CTG GTG GAG TGG ACC AGG CAG AAC
Gln Pro Asp Lys Lys Lys Leu Glu Glu Leu Val Glu Trp Thr Arg Gln Asn

TTC GGG CTT GAT CTA GAG GTG GAC AAA ACT TAC AGG TTC ATT GCC TTC TCC
Phe Gly Leu Asp Leu Glu Val Asp Lys Thr Tyr Arg Phe Ile Ala Phe Ser

GGT CTT AAG AAG AAC TAC TTC GGT GTG TTC AAG GAT TCC AAG CTT GAC ATA
Gly Leu Lys Lys Asn Tyr Phe Gly Val Phe Lys Asp Ser Lys Val Asp Ile
```

*FIGURE 4F*

AAG GGC ATG TTG GCA AAG AAG AGG AAC ACC CCA GAG TTT CTG AAG CAG GCC
Lys Gly Met Leu Ala Lys Lys Arg Asn Thr Pro Glu Phe Leu Lys Gln Ala

TTT AAT GAG GCT AAG GAG AGG CTA GCG AAG GTT CAG AAC CAG GAG GAG CTC
Phe Asn Glu Ala Lys Glu Arg Leu Ala Lys Val Gln Asn Gln Glu Glu Leu

GAA AAG GCA ATT CAA GAC TTA ACG GCG CAG GTT AAG GAG GTG TAC AGG AAG
Glu Lys Ala Ile Gln Asp Leu Thr Ala Gln Val Lys Glu Val Tyr Arg Lys

CTT AAG ATG AAG GAA TAT AAC TTG GAT GAG CTC GCC TTC AGG GTC ATG TTA
Leu Lys Met Lys Glu Tyr Asn Leu Asp Glu Leu Ala Phe Arg Val Met Leu

TCC AGG GAC GTG AAG TCC TAT GAG ATG AAC ACC CCA CAG CAC GTT AAG GCT
Ser Arg Asp Val Lys Ser Tyr Glu Met Asn Thr Pro Gln His Val Lys Ala

GCG GCA CAG CTG GCG GAG ATG AAC GTA CAA GTG ATG TCA AGG GAT ATA ATT
Ala Ala Gln Leu Ala Glu Met Asn Val Gln Val Met Ser Arg Asp Ile Ile

AGC TTC GTA AAG ACT AAG GAG GGA GTT AAA CCT GTC CAG CTA GCT
Ser Phe Val Lys Thr Lys Glu Gly Val Lys Pro Val Gln Leu Ala

*FIGURE 4G*

AAG CTT TCA GAG ATT GAT GTG GAT AAA TAC TAT GAG AGC GTG AGA AGT ACC
Lys Leu Ser Glu Ile Asp Val Asp Lys Tyr Tyr Glu Ser Val Arg Ser Thr

TTC GAA CAG TTA TTG AAA AGC TTC AAT GTG AGC TGG GAT AGA ATA GAG TCC
Phe Glu Gln Leu Leu Lys Ser Phe Asn Val Ser Trp Asp Arg Ile Glu Ser

2634

ACG ACA TCA ATC GAC TCG TTC TTC AAG ACT TAG
Thr Thr Ser Ile Asp Ser Phe Phe Lys Thr End

*FIGURE 4H*

```
(SEQ ID NO:9)  ATG GAG AGG GTT CGC CTA GTG AAG GTG GTT ACC AAG GAT CCT CTA ATC GTG
(SEQ ID NO:10) Met Glu Arg Val Arg Leu Val Lys Val Val Thr Lys Asp Pro Leu Ile Val

AGG AAG ATT AGG AGC AAG TTT AAC ACT GCG TGG GAG GCT AAG ATA AAG TAT
Arg Lys Ile Arg Ser Lys Phe Asn Thr Ala Trp Glu Ala Lys Ile Lys Tyr

CAT GCA AAC TAC ATC TAC GAT AAT AGG CTG ATA CCT GGA ATG AGG TAT GTT
His Ala Asn Tyr Ile Tyr Asp Asn Arg Leu Ile Pro Gly Met Arg Tyr Val

ACA GAC TTC TCC AAC GGT GCG CAA AAG CTT GTA ATG GTT AAG CCA GAG ATA
Thr Asp Phe Ser Asn Gly Ala Gln Lys Leu Val Met Val Lys Pro Glu Ile

CCC CAA TCC CTT GTT GAG AAA GTA AGG GAG AAT GAG CCT CCT
Pro Gln Ser Leu Val Glu Lys Val Arg Glu Asn Glu Pro Pro

GAA ACA GTG AAG CTG GCT GAG GAA CTC CTC TTG TTC GAG GAG TCA CCG
Glu Thr Val Lys Leu Ala Glu Glu Leu Leu Leu Phe Glu Glu Ser Pro

CCC AGG GTG AAG CGC GTA GCA GTC GAC ATA GAG GTT TTC ACC CCA TTC AAA
Pro Arg Val Lys Arg Val Ala Val Asp Ile Glu Val Phe Thr Pro Phe Lys
```

FIGURE 5A

```
GGG CGT ATC CCC AGC CCG AAG CTC GCC GAA TAC CCT GTG ATT AGC ATA GCA
Gly Arg Ile Pro Ser Pro Lys Leu Ala Glu Tyr Pro Val Ile Ser Ile Ala

TTG GCC GGT AGC GAC GGC TTG AAG AAA ATC CTC CTG CTG GCC AGG GAA TAC
Leu Ala Gly Ser Asp Gly Leu Lys Lys Ile Leu Leu Leu Ala Arg Glu Tyr

AAG CAT GAT TTC GAC TAC ATG ATG GAG CAT TAC CCT GTT GAA GCC GAG GTG
Lys His Asp Phe Asp Tyr Met Met Glu His Tyr Pro Val Glu Ala Glu Val

GAG GTG TTC GAC TCC GAG AAA GAC ATG TTG CTG GAA CGG TTG AGA ATA ATG
Glu Val Phe Asp Ser Glu Lys Asp Met Leu Leu Glu Arg Leu Arg Ile Met

GGG AGC TAT CCC GTC CTC GTC ACT TAC AAC GGT GAT AAT TTC GAC CTT CAA
Gly Ser Tyr Pro Val Leu Val Thr Tyr Asn Gly Asp Asn Phe Asp Leu Gln

TAC CTG TAC GTG AGA GCC TTC AAG CTG GGG ATT CTG AGA AGC CAT ATC CCG
Tyr Leu Tyr Val Arg Ala Phe Lys Leu Gly Ile Leu Arg Ser His Ile Pro

TTG AAG ATA GGG GAG GAT ATG ATT AGA ATT GAC ACA AGC ATA CAC CTA GAT
Leu Lys Ile Gly Glu Asp Met Ile Arg Ile Asp Thr Ser Ile His Leu Asp
```

*FIGURE 5B*

```
CTA TAC AAG TTC TTC TCG AAC AGG GCT GTT AAA AAC TAT GCT TTC GGG GGG
Leu Tyr Lys Phe Phe Ser Asn Arg Ala Val Lys Asn Tyr Ala Phe Gly Gly

AAA TAC CAG GAG GAG AAG CTT GAC GCT GTT TCA GGG GCA CTG CTA GGA GTG
Lys Tyr Gln Glu Glu Lys Leu Asp Ala Val Ser Gly Ala Leu Leu Gly Val

TCG AAA ATA GGT TTC GAG GAA ACA ATC GGC GGC ATA TCG GCC TCA CTA TTA
Ser Lys Ile Gly Phe Glu Glu Thr Ile Gly Gly Ile Ser Ala Ser Leu Leu

GCC GCC TAC AAC TAC AGG GAT GCC GAG ATC ACG TTA AAC CTA ACC ATG TTC
Ala Ala Tyr Asn Tyr Arg Asp Ala Glu Ile Thr Leu Asn Leu Thr Met Phe

AGT AAT GAA CTC GTT TGG AAA CTC ATT ATT CTT CTA GCT AGG GTT TCC AAG
Ser Asn Glu Leu Val Trp Lys Leu Ile Ile Leu Leu Ala Arg Val Ser Lys

ACA AGC ATT GAA GAC CTG TGT AGG CAG ATT TCC TAC TGG ATT CAA AAT
Thr Ser Ile Glu Asp Leu Cys Arg Gln Ile Ser Tyr Trp Ile Gln Asn

CTG TTC TTC TGG GAG CGC AGG AAG CTC ATA CCT AAC AAG GAG
Leu Phe Phe Trp Glu Arg Arg Lys Leu Gly Tyr Leu Ile Pro Asn Lys Glu
```

*FIGURE 5C*

```
GAC ATT CTG AGG CAT GTA AGG GGG ACG AAG GCG ATT ATT GAG GGT
Asp Ile Leu Arg His Val Arg Gly Thr Lys Ala Ile Ile Glu Gly

AAG TAC GCT GGA GCC TTA GTG GTT GAG CCT CCG AAA GGG GCT TTC TTC
Lys Tyr Ala Gly Ala Leu Val Val Glu Pro Pro Lys Gly Ala Phe Phe

AAC GTG GTC GTC GAC ATA GCC TCC CTA TAC CCT AGC ATT ATC AAA AAA
Asn Val Val Val Asp Ile Ala Ser Leu Tyr Pro Ser Ile Ile Lys Lys

TAC AAT CTG AGC TAT GAG ACC GTT GAC ATG AAG TGG TGT AGC AAG ACA ATA
Tyr Asn Leu Ser Tyr Glu Thr Val Asp Met Lys Trp Cys Ser Lys Thr Ile

GAT ATT GTC GAT GAA GGG AGA AGG CTT CAC GAA GTC TGC GTT GAC AAG
Asp Ile Val Asp Glu Gly Arg Arg Leu His Glu Val Cys Val Asp Lys

CCC GGG TTG ACC GCG CAA CTA ACC GGT ATT CTA AGG GAT TAC AGG CTT GGA
Pro Gly Leu Thr Ala Gln Leu Thr Gly Ile Leu Arg Asp Tyr Arg Val Gly

ATA TAT AAG AAG AGG TCT AAG GAT AAG AGC CTT CCC CCT GAA ACC CTG GCC
Ile Tyr Lys Lys Arg Ser Lys Asp Lys Ser Leu Pro Pro Glu Thr Leu Ala
```

```
TGG TAC GAG GTG GTT CAG AGA GCT ATT AAG GTG TTC ATA AAC GCT AGC TAC
Trp Tyr Glu Val Val Gln Arg Ala Ile Lys Val Phe Ile Asn Ala Ser Tyr

GGG GTC TTC GGG GAT GAG AAG TTC TCT CTG TAC TCC CCA GCA GTG GCT GAA
Gly Val Phe Gly Asp Glu Lys Phe Ser Leu Tyr Ser Pro Ala Val Ala Glu

AGC GTT ACC GCG ATG GGT AGG TCC TTC TAC ACT ATT GTG AGA AAG GCC
Ser Val Thr Ala Met Gly Arg Ser Phe Tyr Thr Ile Val Arg Lys Ala

GCG GAT CTC GGG GTT AAA ACA CTG TAT GGC GAC ACG GAC TCG ATA TTC GTC
Ala Asp Leu Gly Val Lys Thr Leu Tyr Gly Asp Thr Asp Ser Ile Phe Val

TGG GCC CCA ACC CAG GAG CAG TTG AGG AAG CTA CAG TCA TGG ATC CTT GAG
Trp Ala Pro Thr Gln Glu Gln Leu Arg Lys Leu Gln Ser Trp Ile Leu Glu

AAG CTA GGC CTG GAG ATC GAG ATT GAC AAG TCT TTT ACA TAC GTG GTT TTC
Lys Leu Gly Leu Glu Ile Glu Ile Asp Lys Ser Phe Thr Tyr Val Val Phe

ACA GGG CTT AAG AAA AAC TAC CTG GGC AGA ACG GTT GAC GGC GGC ATA GAG
Thr Gly Leu Lys Lys Asn Tyr Leu Gly Arg Thr Val Asp Gly Gly Ile Glu
```

```
ATC AAG GGG CTT GTC SCG AAG AAG AGG AAT ACT CCG GAG TTC CTG AAA GAC
Ile Lys Gly Leu Val Xxx Lys Lys Arg Asn Thr Pro Glu Phe Leu Lys Asp

TTG TTC GAG AAT GTT ATC GAA AAG CTT AAA AGC GTT GAA AAC CCC GCG GGT
Leu Phe Glu Asn Val Ile Glu Lys Leu Lys Ser Val Glu Asn Pro Ala Gly

TTC ATA GAG TTC GTC AAG TGG TTG GAG CAT CAG AAG ACA ATA CAT AAC
Phe Ile Glu Phe Val Lys Trp Leu Glu His Gln Val Lys Thr Ile His Asn

GAT ATT AGG AGG AAG GAG ATA ACG CTC GAC CGG CTC GCC ATA AGG GTG GCC
Asp Ile Arg Arg Lys Glu Ile Thr Leu Asp Arg Leu Ala Ile Arg Val Ala

TTA ACC AAG ACG CCA TCC CTC TAC ACT AAG CCG CAT GTG AAG
Leu Thr Lys Thr Pro Ser Leu Tyr Thr Lys Pro His Val Lys

GCA GCC CTC CAA TTA ATG AAC TAC GGG TAC AGC GTG GAG GAG GGG GAT ATT
Ala Ala Leu Gln Leu Met Asn Tyr Gly Tyr Ser Val Glu Glu Gly Asp Ile

ATA ACG TTT GTC AAG GTG AAG AGC AAG GAG GGC TAT AAG GCT ATA CAG TTA
Ile Thr Phe Val Lys Val Lys Ser Lys Glu Gly Tyr Lys Ala Ile Gln Leu
```

*FIGURE 5F*

ACG AGG CTT CAC GAA GTA GAC CCT GAT AAG TAC ATT GAG CTT GTT AAA AGC
Thr Arg Leu His Glu Val Asp Pro Asp Lys Tyr Ile Glu Leu Val Lys Ser

GGT CTT GAA CAA TTC CTC TCA GCC TTC GGA ATA AGG TGG GAG GAT ATC ATA
Gly Leu Glu Gln Phe Leu Ser Ala Phe Gly Ile Arg Trp Glu Asp Ile Ile

GGC TCC GGC GGG TTA ACC GAG CTT TTG AGA AAC AAT AGG GCG TAG
Gly Ser Gly Gly Leu Thr Glu Leu Leu Arg Asn Asn Arg Ala End

*FIGURE 5G*

(SEQ ID NO:11) ATG GAT TTT GAA TAC GTA ACG GGA GAA GAG GGA TTA AAA AAG GCA ATA AAA
(SEQ ID NO:12) Met Asp Phe Glu Tyr Val Thr Gly Glu Glu Gly Leu Lys Lys Ala Ile Lys

AGG CTC GAA AAT TCT CCA TAC TAC CTT TAC CTG GAT ACG GAA ACC ACA GGA GAC
Arg Leu Glu Asn Ser Pro Tyr Tyr Leu Tyr Leu Asp Thr Glu Thr Thr Gly Asp

AGG ATA AGG CTC GTA CAA ATC GGA GAC GAA GAA AAC ACC TAC GTT ATT GAC
Arg Ile Arg Leu Val Gln Ile Gly Asp Glu Glu Asn Thr Tyr Val Ile Asp

CTC TAC GAA ATT CAG GAT ATA GAA CCT CTG AGG AAA TTA ATA AAC GAA AGG
Leu Tyr Glu Ile Gln Asp Ile Glu Pro Leu Arg Lys Leu Ile Asn Glu Arg

GGG ATA GTA GGG CAC AAC CTT AAG TTC GAT CTT AAG TAC CTC TAC AGG TAC
Gly Ile Val Gly His Asn Leu Lys Phe Asp Leu Lys Tyr Leu Tyr Arg Tyr

GGG ATA TTT CCC TCG GCA ACG TTT GAC ACT ATG ATA GCG AGC TAC CTC CTC
Gly Ile Phe Pro Ser Ala Thr Phe Asp Thr Met Ile Ala Ser Tyr Leu Leu

GGA TAC GAG AGA CAC TCC CTC AAT CAC ATA GTT TCA AAC CTA CTC GGA TAT
Gly Tyr Glu Arg His Ser Leu Asn His Ile Val Ser Asn Leu Leu Gly Tyr

*FIGURE 6A*

```
TCC ATG GAC AAG AGT TAT CAG ACT TCC GAC TGG GGA GCG AGC GTT CTG AGC
Ser Met Asp Lys Ser Tyr Gln Thr Ser Asp Trp Gly Ala Ser Val Leu Ser

GAC GCT CAG CTC AAG TAC GCT GCA AAC GAC GTT ATA GTC CTC AGA GAA CTC
Asp Ala Gln Leu Lys Tyr Ala Ala Asn Asp Val Ile Val Leu Arg Glu Leu

TTC CCT AAG ATG AGG GAC ATG TTA AAC GAG CTA GAC GCT GAG AGG GGA GAG
Phe Pro Lys Met Arg Asp Met Leu Asn Glu Leu Asp Ala Glu Arg Gly Glu

GAA CTC CTC AAG ACT AGA ACG GCA AAG ATT TTC GAT CTG AAG AGT CCC GTA
Glu Leu Leu Lys Thr Arg Thr Ala Lys Ile Phe Asp Leu Lys Ser Pro Val

GCA ATA GTG GAA ATG GCT TTC GTA GAA GTT GCA AAA CTC GAG ATA AAC
Ala Ile Val Glu Met Ala Phe Val Arg Glu Val Ala Lys Leu Glu Ile Asn

GGC TTT CCC GTG GAC GTA GAA GAG CTA ACC AAC AAG TTA AAA GCT GTG GAA
Gly Phe Pro Val Asp Val Glu Glu leu Thr Asn Lys Leu Lys Ala Val Glu AGG GAA ACC CAG AAG AGG ATA CAG GAG TTT TAC ATA AAG TAC ATA GTT GAC
Arg Glu Thr Gln Lys Arg Ile Gln Glu Phe Tyr Ile Lys Tyr Arg Val Asp
```

*FIGURE 6B*

CCT CTC TCT CCG AAA CAG CTC CTG ACG AAG TTT AAA CTG
Pro Leu Ser Pro Lys Gln Leu Leu Thr Lys Phe Lys Leu

AAC CTT CCC AAG ACT CCT AAA GGG AAC GTA TCT GAC AAG GCT CTT
Asn Leu Pro Lys Thr Pro Lys Gly Asn Val Ser Asp Lys Ala Leu

ACT TCC TAT CAG GAC GTA GAA CCC GTA AAA CTC GTT CTG GAA ATA AGA AAG
Thr Ser Tyr Gln Asp Val Glu Pro Val Lys Leu Val Leu Glu Ile Arg Lys

CTT AAG AAA ATC GCC GAC AAG TTA AAG GAG TTA AAA GAA CAC TTC AAG AAC
Leu Lys Lys Ile Ala Asp Lys Leu Lys Glu Leu Lys Glu His Leu Lys Asn

GGG AGA GTT TAC CCG GAG TTC AAG CAA ATA CAG AAC ATA GGA GCT GTA ACG GGA AGG ATG
Gly Arg Val Tyr Pro Glu Phe Lys Gln Ile Gln Asn Ile Gly Ala Val Thr Gly Arg Met

TCC TCC GCA CAC CCA AAT ATC CAG AAC ATA CAC AGG GAT ATG AGA GGA ATT
Ser Ser Ala His Pro Asn Ile Gln Asn Ile His Arg Asp Met Arg Gly Ile

TTC AAG GCG GAG GGA AAT ACT TTC GTC ATT TCG GAC TTT TCT CAG ATA
Phe Lys Ala Glu Gly Asn Thr Phe Val Ile Ser Asp Phe Ser Gln Ile

```
GAG CTC AGG ATT GCG GCC GAA TAC GTA AAG GAC CCG CTT ATG CTG GAC GCC
Glu Leu Arg Ile Ala Ala Glu Tyr Val Lys Asp Pro Leu Met Leu Asp Ala

TTC AAA AAG GGA AAG GAC ATG CAC AGG TAC ACC GCT TCA GTG GTA CTC GGA
Phe Lys Lys Gly Lys Asp Met His Arg Tyr Thr Ala Ser Val Val Leu Gly

AAA GAG GAA GAA ATA ACA AAA GAG GAG AGA CAG CTC GCA AAA GCT ATA
Lys Glu Glu Glu Ile Thr Lys Glu Glu Arg Gln Leu Ala Lys Ala Ile

AAC TTC GGT CTC ATA TAC GGC ATT TCC GCT AAA GGG CTT GCA GAA TAC GCA
Asn Phe Gly Leu Ile Tyr Gly Ile Ser Ala Lys Gly Leu Ala Glu Tyr Ala

AAG CTT GGT TAC GGC GTT GAA ATT TCT TTA GAA GAA GCT CAG GTT TTG AGA
Lys Leu Gly Tyr Gly Val Glu Ile Ser Leu Glu Glu Ala Gln Val Leu Arg

GAG AGG TTT TTC AAG AAC TTC AAA GCT TTC AAA GAG TGG CAC GAC AGA GTT
Glu Arg Phe Phe Lys Asn Phe Lys Ala Phe Lys Glu Trp His Asp Arg Val

AAG AAA GAA CTA AAG GGA GAG GTA AAA GGT CAT ACG CTT CTT GGA
Lys Lys Glu Leu Lys Gly Glu Val Lys Gly His Thr Leu Leu Gly
```

```
AGG AGA TTT TCC GCA AAT ACC TTT AAC GAC GCT GTA AAT TAC CCC ATA CAG
Arg Arg Phe Ser Ala Asn Thr Phe Asn Asp Ala Val Asn Tyr Pro Ile Gln

GGA ACG GGT GCG GAC CTA CTA AAA CTG GCA GTT CTA CTT TTT GAC GCA AAC
Gly Thr Gly Ala Asp Leu Leu Lys Leu Ala Val Leu Leu Phe Asp Ala Asn

CTC CAG AAA AAG GGA ATA GAT GCA AAG CTC GTG CAC GAC GAG
Leu Gln Lys Lys Gly Ile Asp Ala Lys Leu Val His Asp Glu

ATA GTC GTA GAG TGC GAA AAA GGA GAA GTA AAA GAA ATA CTC
Ile Val Val Glu Cys Glu Lys Gly Glu Val Lys Glu Ile Leu

GAA AAA GCC ATG AAA ACG GCG GGA AAG ATA ATA CTG AAA GAG GTT CCC GTG
Glu Lys Ala Met Lys Thr Ala Gly Lys Ile Ile Leu Lys Glu Val Pro Val

1725

GAA GTA GAA AGC GTT ATA AAC GAA AGG TGG ACG AAA GAT TAA
Glu Val Glu Ser Val Ile Asn Glu Arg Trp Thr Lys Asp End
```

*FIGURE 6E*

SEQUENCE LISTING

<160> NUMBER OF SEQ ID NOS: 12

<210> SEQ ID NO 1
<211> LENGTH: 2607
<212> TYPE: DNA
<213> ORGANISM: Ammonifex degensii
<220> FEATURE:
<221> NAME/KEY: CDS
<222> LOCATION: (1)...(2604)

<400> SEQUENCE: 1

```
gtg aag gga aaa acc ttg ctc ctt ttg gac ggc tcg agc ata gcc tac      48
Val Lys Gly Lys Thr Leu Leu Leu Leu Asp Gly Ser Ser Ile Ala Tyr
 1               5                  10                  15 cgg gcc ttt ttc gcc ctt ccc tcc ctc cgc acc cgt acc ggc ctg ccc      96
Arg Ala Phe Phe Ala Leu Pro Ser Leu Arg Thr Arg Thr Gly Leu Pro
                20                  25                  30 acc ggt gcc gtg tac ggc ttt acc tcc atg ctc ttc aaa gtg ctg gaa     144
Thr Gly Ala Val Tyr Gly Phe Thr Ser Met Leu Phe Lys Val Leu Glu
            35                  40                  45 gaa agg cgt ccc acg gcc ata gtg gcg gct ttc gat aaa agc aag acc     192
Glu Arg Arg Pro Thr Ala Ile Val Ala Ala Phe Asp Lys Ser Lys Thr
        50                  55                  60 acc ttc cgg cac gcc ctg gcg gag acc tac aag gcc cac cgc ccc gcc     240
Thr Phe Arg His Ala Leu Ala Glu Thr Tyr Lys Ala His Arg Pro Ala
 65                 70                  75                  80 act ccg gat gaa ctg cgc cag cag ttc aac ctc atc aag gaa gtg ctg     288
Thr Pro Asp Glu Leu Arg Gln Gln Phe Asn Leu Ile Lys Glu Val Leu
                85                  90                  95 act gcc ctc aac gtt ccg gta gtg gaa aag gag ggt ttt gag gcc gac     336
Thr Ala Leu Asn Val Pro Val Val Glu Lys Glu Gly Phe Glu Ala Asp
               100                 105                 110 gac ctc atc ggc act ctg gta gac cgg gcg gaa aaa gag ggt tgg cag     384
Asp Leu Ile Gly Thr Leu Val Asp Arg Ala Glu Lys Glu Gly Trp Gln
           115                 120                 125 tgc ctt atc gtc acc ggc gac ctc gac gcc ctg cag ctg gtt tcc ccc     432
Cys Leu Ile Val Thr Gly Asp Leu Asp Ala Leu Gln Leu Val Ser Pro
       130                 135                 140 ctc acc acc gtc gtc ctc atg cgc aag ggg ata agc gaa ata gcg gtc     480
Leu Thr Thr Val Val Leu Met Arg Lys Gly Ile Ser Glu Ile Ala Val
145                 150                 155                 160 ttt aac gag gcg gag gtg aaa cgc cgc ttc ggc gtc aca ccc cgc caa     528
Phe Asn Glu Ala Glu Val Lys Arg Arg Phe Gly Val Thr Pro Arg Gln
               165                 170                 175 ctc ccc gac ttc aaa gcc ttg gcc gga gat gcc tcg gac aac atc ccc     576
Leu Pro Asp Phe Lys Ala Leu Ala Gly Asp Ala Ser Asp Asn Ile Pro
           180                 185                 190 ggg ctt ccg ggc ata ggg ccc aaa act gcc tcc cgt ctg cta cag tcc     624
```

```
                Gly Leu Pro Gly Ile Gly Pro Lys Thr Ala Ser Arg Leu Leu Gln Ser
                            195                 200                 205 cac cag agc ctg gag aaa ttg ctg gag agc aag gaa ttt ttt ccg gcc        672
His Gln Ser Leu Glu Lys Leu Leu Glu Ser Lys Glu Phe Phe Pro Ala
            210                 215                 220 aag ctg cgc gaa acc tta gaa agg cac aag gaa gaa gcg gtt ttg gcc        720
Lys Leu Arg Glu Thr Leu Glu Arg His Lys Glu Glu Ala Val Leu Ala
225                 230                 235                 240 aag aaa ctg gcc ctc atc cgc cgc gat gtg ccg ctg gaa gag gag atc        768
Lys Lys Leu Ala Leu Ile Arg Arg Asp Val Pro Leu Glu Glu Glu Ile
                245                 250                 255 atc cgg ccc tgg ccg gga ccc aac att tta gcc acg ctg gag gtc ttc        816
Ile Arg Pro Trp Pro Gly Pro Asn Ile Leu Ala Thr Leu Glu Val Phe
            260                 265                 270 tcg cgc ctg gaa ttc cgc acc ttg gcc aag aga ttc ctc gag ctt ttc        864
Ser Arg Leu Glu Phe Arg Thr Leu Ala Lys Arg Phe Leu Glu Leu Phe
        275                 280                 285 ccc gag gca cgc ctc ctg tcc gcc agt ggc ctt acc ccc tcc gct gtc        912
Pro Glu Ala Arg Leu Leu Ser Ala Ser Gly Leu Thr Pro Ser Ala Val
    290                 295                 300 cgc gta aag gta gaa aga ccc gaa gaa cta gaa aga ctg ggg gaa gag        960
Arg Val Lys Val Glu Arg Pro Glu Glu Leu Glu Arg Leu Gly Glu Glu
305                 310                 315                 320 ctc gga agg caa gaa ttt gcg gcc ctg gct tac ccc ccc gtt ctt cgg       1008
Leu Gly Arg Gln Glu Phe Ala Ala Leu Ala Tyr Pro Pro Val Leu Arg
                325                 330                 335 cgc aaa gcc act tct tct ttc ttg gct ctc tgt ctg gga ggg gaa aag       1056
Arg Lys Ala Thr Ser Ser Phe Leu Ala Leu Cys Leu Gly Gly Glu Lys
            340                 345                 350 gtc ttc ctg ctg gaa ggg ccg gag gtg ctc aag agc ttc ttc cgg ctg       1104
Val Phe Leu Leu Glu Gly Pro Glu Val Leu Lys Ser Phe Phe Arg Leu
        355                 360                 365 ctc gaa gaa aag gga ggt ctt gtc agt acc tac gac gct aaa tcc tgc       1152
Leu Glu Glu Lys Gly Gly Leu Val Ser Thr Tyr Asp Ala Lys Ser Cys
    370                 375                 380 ctt cac gcc ctg gaa cct tac ggc ttc aag ccc gaa atg atc ggg ttt       1200
Leu His Ala Leu Glu Pro Tyr Gly Phe Lys Pro Glu Met Ile Gly Phe
385                 390                 395                 400 gac gtc ctg ctg gca gcc tac ctg gtg aac ccc gcc gcc aac aac gaa       1248
Asp Val Leu Leu Ala Ala Tyr Leu Val Asn Pro Ala Ala Asn Asn Glu
                405                 410                 415 ctg ggg gcg atc gcc ttc gag cac gcg ggc ttt atg ctc tcc ccg gga       1296
Leu Gly Ala Ile Ala Phe Glu His Ala Gly Phe Met Leu Ser Pro Gly
            420                 425                 430 gca gag ctc ccg gaa aaa gcc cag gcg atc tac cag ctc acc ccc atc       1344
Ala Glu Leu Pro Glu Lys Ala Gln Ala Ile Tyr Gln Leu Thr Pro Ile
        435                 440                 445 cta aaa agt aag att aag ctt cag gaa cag gag tac ctt tat tac tcc       1392
Leu Lys Ser Lys Ile Lys Leu Gln Glu Gln Glu Tyr Leu Tyr Tyr Ser
    450                 455                 460 gtg gag ctt ccc tta gcc gcc gtc ttg gcc gac atg gag aaa gtc ggg       1440
Val Glu Leu Pro Leu Ala Ala Val Leu Ala Asp Met Glu Lys Val Gly
465                 470                 475                 480 gtg aaa gtt tcg gag gaa agg ctg cgt tct ctc tcc aag gag ctg gga       1488
Val Lys Val Ser Glu Glu Arg Leu Arg Ser Leu Ser Lys Glu Leu Gly
                485                 490                 495 gag cag ctg gct cag ctt tcc gag gaa atc tat aag ctc gcc ggc gag       1536
Glu Gln Leu Ala Gln Leu Ser Glu Glu Ile Tyr Lys Leu Ala Gly Glu
            500                 505                 510
```

-continued

| | |
|---|---|
| cgc ttc aac ctg aat tcc ccc cgc cag ctc ggc tac atc ctg ttc gag<br>Arg Phe Asn Leu Asn Ser Pro Arg Gln Leu Gly Tyr Ile Leu Phe Glu<br>515                      520                    525 | 1584 |
| aag ttg gga ctc aaa ccg gtc aag aag acc aaa acc ggc tac tcc acc<br>Lys Leu Gly Leu Lys Pro Val Lys Lys Thr Lys Thr Gly Tyr Ser Thr<br>530                      535                    540 | 1632 |
| gac gct tcg gtc cta gaa aag cta gcc gag cac gag atc gtg gct aag<br>Asp Ala Ser Val Leu Glu Lys Leu Ala Glu His Glu Ile Val Ala Lys<br>545                      550                    555                    560 | 1680 |
| gtg ctc gtc tac cgg cag ctg gcc aaa cta aag agc act tac acc gac<br>Val Leu Val Tyr Arg Gln Leu Ala Lys Leu Lys Ser Thr Tyr Thr Asp<br>                  565                    570                    575 | 1728 |
| gca ctt cca gag ctc atc gac ccg gcc acc ggg cgc ctg cac acc acc<br>Ala Leu Pro Glu Leu Ile Asp Pro Ala Thr Gly Arg Leu His Thr Thr<br>580                      585                    590 | 1776 |
| ttc ttg cag gca ggg acg gca acg gga aga ctg gcc tcc gcc gag ccc<br>Phe Leu Gln Ala Gly Thr Ala Thr Gly Arg Leu Ala Ser Ala Glu Pro<br>                  595                    600                    605 | 1824 |
| aac ctg cag aac att ccc gta cgc gat tct ctg gga agg cgc atc cgg<br>Asn Leu Gln Asn Ile Pro Val Arg Asp Ser Leu Gly Arg Arg Ile Arg<br>610                      615                    620 | 1872 |
| cag gcc ttc gtg gct gag ggc ccc gac tac gtg cta cta agc gcc gac<br>Gln Ala Phe Val Ala Glu Gly Pro Asp Tyr Val Leu Leu Ser Ala Asp<br>625                      630                    635                    640 | 1920 |
| tac tcc cag ata gag ctt cgg gtc ttg gcc cac ctt tcc gaa gat ccg<br>Tyr Ser Gln Ile Glu Leu Arg Val Leu Ala His Leu Ser Glu Asp Pro<br>                  645                    650                    655 | 1968 |
| ggg ctg tgt gag gcc ttt gtt aaa gga gaa gac att cac gcc cgc acg<br>Gly Leu Cys Glu Ala Phe Val Lys Gly Glu Asp Ile His Ala Arg Thr<br>660                      665                    670 | 2016 |
| gcg gcc gag atc ttc ggc gtt tct cct cag gaa gtg acg ccg gag atg<br>Ala Ala Glu Ile Phe Gly Val Ser Pro Gln Glu Val Thr Pro Glu Met<br>                  675                    680                    685 | 2064 |
| cgg gcc aag gcc aag gtg gta aac ttc ggg atc gtt tac ggc atg agc<br>Arg Ala Lys Ala Lys Val Val Asn Phe Gly Ile Val Tyr Gly Met Ser<br>690                      695                    700 | 2112 |
| gat tac ggc ctt tcc cag gag ctc aag atc gag ccc ggc gag gcg cac<br>Asp Tyr Gly Leu Ser Gln Glu Leu Lys Ile Glu Pro Gly Glu Ala His<br>705                      710                    715                    720 | 2160 |
| gag tat ata gaa cgg tac ttc cgg cgc tat ccg cgc gtg aag cag ttc<br>Glu Tyr Ile Glu Arg Tyr Phe Arg Arg Tyr Pro Arg Val Lys Gln Phe<br>                  725                    730                    735 | 2208 |
| atc gag cgg gtg atc gcc cag gcc cga gag aag ggc tac gtg acc act<br>Ile Glu Arg Val Ile Ala Gln Ala Arg Glu Lys Gly Tyr Val Thr Thr<br>740                      745                    750 | 2256 |
| att ctc aac cgc cgc cgc tac atc cct gaa ata ctg agc agc aac cgc<br>Ile Leu Asn Arg Arg Arg Tyr Ile Pro Glu Ile Leu Ser Ser Asn Arg<br>                  755                    760                    765 | 2304 |
| aac cag cgt cag ctg ggg gag cgc ctg gcc atc aac acc acc att caa<br>Asn Gln Arg Gln Leu Gly Glu Arg Leu Ala Ile Asn Thr Thr Ile Gln<br>770                      775                    780 | 2352 |
| gga agt gcg gcc gat ctt ata aaa aag gcc atg gtg gac atc cac cgg<br>Gly Ser Ala Ala Asp Leu Ile Lys Lys Ala Met Val Asp Ile His Arg<br>785                      790                    795                    800 | 2400 |
| caa ctg aaa ggg caa gga ttt aaa tgc cgg atg atc ctc cag gtg cac<br>Gln Leu Lys Gly Gln Gly Phe Lys Cys Arg Met Ile Leu Gln Val His<br>                  805                    810                    815 | 2448 |
| gac gaa ctc ctc ttc gag gtg cct aaa gaa gaa ctg gaa aag gtg gca<br>Asp Glu Leu Leu Phe Glu Val Pro Lys Glu Glu Leu Glu Lys Val Ala<br>820                      825                    830 | 2496 |

```
cct ata ata aaa agc acc atg gag caa gcc tta cct ttt aag gtt ccc    2544
Pro Ile Ile Lys Ser Thr Met Glu Gln Ala Leu Pro Phe Lys Val Pro
        835                 840                 845 ata aag gcc aac ctc aag gta ggg cct aac tgg caa gac atg gaa gag    2592
Ile Lys Ala Asn Leu Lys Val Gly Pro Asn Trp Gln Asp Met Glu Glu
850                 855                 860 tac gag gtg gaa tga                                                2607
Tyr Glu Val Glu
865

<210> SEQ ID NO 2
<211> LENGTH: 868
<212> TYPE: PRT
<213> ORGANISM: Ammonifex degensii

<400> SEQUENCE: 2

Val Lys Gly Lys Thr Leu Leu Leu Asp Gly Ser Ser Ile Ala Tyr
 1               5                  10                  15

Arg Ala Phe Phe Ala Leu Pro Ser Leu Arg Thr Arg Thr Gly Leu Pro
            20                  25                  30

Thr Gly Ala Val Tyr Gly Phe Thr Ser Met Leu Phe Lys Val Leu Glu
        35                  40                  45

Glu Arg Arg Pro Thr Ala Ile Val Ala Ala Phe Asp Lys Ser Lys Thr
 50                  55                  60

Thr Phe Arg His Ala Leu Ala Glu Thr Tyr Lys Ala His Arg Pro Ala
65                  70                  75                  80

Thr Pro Asp Glu Leu Arg Gln Gln Phe Asn Leu Ile Lys Glu Val Leu
                85                  90                  95

Thr Ala Leu Asn Val Pro Val Glu Lys Gly Phe Glu Ala Asp
            100                 105                 110

Asp Leu Ile Gly Thr Leu Val Asp Arg Ala Glu Lys Glu Gly Trp Gln
            115                 120                 125

Cys Leu Ile Val Thr Gly Asp Leu Asp Ala Leu Gln Leu Val Ser Pro
        130                 135                 140

Leu Thr Thr Val Val Leu Met Arg Lys Gly Ile Ser Glu Ile Ala Val
145                 150                 155                 160

Phe Asn Glu Ala Glu Val Lys Arg Arg Phe Gly Val Thr Pro Arg Gln
                165                 170                 175

Leu Pro Asp Phe Lys Ala Leu Ala Gly Asp Ala Ser Asp Asn Ile Pro
            180                 185                 190

Gly Leu Pro Gly Ile Gly Pro Lys Thr Ala Ser Arg Leu Leu Gln Ser
        195                 200                 205

His Gln Ser Leu Glu Lys Leu Leu Glu Ser Lys Glu Phe Phe Pro Ala
    210                 215                 220

Lys Leu Arg Glu Thr Leu Glu Arg His Lys Glu Glu Ala Val Leu Ala
225                 230                 235                 240

Lys Lys Leu Ala Leu Ile Arg Arg Asp Val Pro Leu Glu Glu Glu Ile
                245                 250                 255

Ile Arg Pro Trp Pro Gly Pro Asn Ile Leu Ala Thr Leu Glu Val Phe
            260                 265                 270

Ser Arg Leu Glu Phe Arg Thr Leu Ala Lys Arg Phe Leu Glu Leu Phe
        275                 280                 285

Pro Glu Ala Arg Leu Leu Ser Ala Ser Gly Leu Thr Pro Ser Ala Val
    290                 295                 300

Arg Val Lys Val Glu Arg Pro Glu Glu Leu Glu Arg Leu Gly Glu Glu
```

-continued

```
305                 310                 315                 320

Leu Gly Arg Gln Glu Phe Ala Ala Leu Ala Tyr Pro Pro Val Leu Arg
                325                 330                 335

Arg Lys Ala Thr Ser Ser Phe Leu Ala Leu Cys Leu Gly Gly Glu Lys
                340                 345                 350

Val Phe Leu Leu Glu Gly Pro Glu Val Leu Lys Ser Phe Phe Arg Leu
                355                 360                 365

Leu Glu Glu Lys Gly Gly Leu Val Ser Thr Tyr Asp Ala Lys Ser Cys
                370                 375                 380

Leu His Ala Leu Glu Pro Tyr Gly Phe Lys Pro Glu Met Ile Gly Phe
385                 390                 395                 400

Asp Val Leu Leu Ala Ala Tyr Leu Val Asn Pro Ala Ala Asn Asn Glu
                405                 410                 415

Leu Gly Ala Ile Ala Phe Glu His Ala Gly Phe Met Leu Ser Pro Gly
                420                 425                 430

Ala Glu Leu Pro Glu Lys Ala Gln Ala Ile Tyr Gln Leu Thr Pro Ile
                435                 440                 445

Leu Lys Ser Lys Ile Lys Leu Gln Glu Gln Tyr Leu Tyr Tyr Ser
                450                 455                 460

Val Glu Leu Pro Leu Ala Ala Val Leu Ala Asp Met Glu Lys Val Gly
465                 470                 475                 480

Val Lys Val Ser Glu Glu Arg Leu Arg Ser Leu Ser Lys Glu Leu Gly
                485                 490                 495

Glu Gln Leu Ala Gln Leu Ser Glu Glu Ile Tyr Lys Leu Ala Gly Glu
                500                 505                 510

Arg Phe Asn Leu Asn Ser Pro Arg Gln Leu Gly Tyr Ile Leu Phe Glu
                515                 520                 525

Lys Leu Gly Leu Lys Pro Val Lys Lys Thr Lys Thr Gly Tyr Ser Thr
                530                 535                 540

Asp Ala Ser Val Leu Glu Lys Leu Ala Glu His Glu Ile Val Ala Lys
545                 550                 555                 560

Val Leu Val Tyr Arg Gln Leu Ala Lys Leu Lys Ser Thr Tyr Thr Asp
                565                 570                 575

Ala Leu Pro Glu Leu Ile Asp Pro Ala Thr Gly Arg Leu His Thr Thr
                580                 585                 590

Phe Leu Gln Ala Gly Thr Ala Thr Gly Arg Leu Ala Ser Ala Glu Pro
                595                 600                 605

Asn Leu Gln Asn Ile Pro Val Arg Asp Ser Leu Gly Arg Arg Ile Arg
                610                 615                 620

Gln Ala Phe Val Ala Glu Gly Pro Asp Tyr Val Leu Leu Ser Ala Asp
625                 630                 635                 640

Tyr Ser Gln Ile Glu Leu Arg Val Leu Ala His Leu Ser Glu Asp Pro
                645                 650                 655

Gly Leu Cys Glu Ala Phe Val Lys Gly Glu Asp Ile His Ala Arg Thr
                660                 665                 670

Ala Ala Glu Ile Phe Gly Val Ser Pro Gln Glu Val Thr Pro Glu Met
                675                 680                 685

Arg Ala Lys Ala Lys Val Val Asn Phe Gly Ile Val Tyr Gly Met Ser
                690                 695                 700

Asp Tyr Gly Leu Ser Gln Glu Leu Lys Ile Glu Pro Gly Glu Ala His
705                 710                 715                 720

Glu Tyr Ile Glu Arg Tyr Phe Arg Arg Tyr Pro Arg Val Lys Gln Phe
                725                 730                 735
```

-continued

```
Ile Glu Arg Val Ile Ala Gln Ala Arg Glu Lys Gly Tyr Val Thr Thr
            740                 745                 750
Ile Leu Asn Arg Arg Tyr Ile Pro Glu Ile Leu Ser Ser Asn Arg
        755                 760                 765
Asn Gln Arg Gln Leu Gly Glu Arg Leu Ala Ile Asn Thr Thr Ile Gln
        770                 775                 780
Gly Ser Ala Ala Asp Leu Ile Lys Lys Ala Met Val Asp Ile His Arg
785                 790                 795                 800
Gln Leu Lys Gly Gln Gly Phe Lys Cys Arg Met Ile Leu Gln Val His
                805                 810                 815
Asp Glu Leu Leu Phe Glu Val Pro Lys Glu Glu Leu Glu Lys Val Ala
            820                 825                 830
Pro Ile Ile Lys Ser Thr Met Glu Gln Ala Leu Pro Phe Lys Val Pro
        835                 840                 845
Ile Lys Ala Asn Leu Lys Val Gly Pro Asn Trp Gln Asp Met Glu Glu
    850                 855                 860
Tyr Glu Val Glu
865

<210> SEQ ID NO 3
<211> LENGTH: 2412
<212> TYPE: DNA
<213> ORGANISM: Pyrolobus fumarius
<220> FEATURE:
<221> NAME/KEY: CDS
<222> LOCATION: (1)...(2410)

<400> SEQUENCE: 3 atg act gaa gtt gta ttc acg gtt tta gac tct agc tac gag gtt gtt      48
Met Thr Glu Val Val Phe Thr Val Leu Asp Ser Ser Tyr Glu Val Val
1               5                   10                  15 ggt aaa gag cct cag gta atc ata tgg ggt att gct gag aac ggc gag      96
Gly Lys Glu Pro Gln Val Ile Ile Trp Gly Ile Ala Glu Asn Gly Glu
                20                  25                  30 agg gta gtc ctc att gac agg tct ttt cgc cca tac ttc tat gcg ctg     144
Arg Val Val Leu Ile Asp Arg Ser Phe Arg Pro Tyr Phe Tyr Ala Leu
            35                  40                  45 ctt gca ccg ggc gcc gat cct aag cag gta gca caa cgt att cgt gca     192
Leu Ala Pro Gly Ala Asp Pro Lys Gln Val Ala Gln Arg Ile Arg Ala
        50                  55                  60 ttg agt agg cca aag agc ccg att ata ggt gta gag gat gac aag agg     240
Leu Ser Arg Pro Lys Ser Pro Ile Ile Gly Val Glu Asp Asp Lys Arg
65                  70                  75                  80 aag tac ttc ggg agg cct cgt agg gtc tta cgt att cgc acc gtg cta     288
Lys Tyr Phe Gly Arg Pro Arg Arg Val Leu Arg Ile Arg Thr Val Leu
                85                  90                  95 ccc gag gct gtt agg gag tat cgc gaa ctc gta aag aac gtt gat ggt     336
Pro Glu Ala Val Arg Glu Tyr Arg Glu Leu Val Lys Asn Val Asp Gly
                100                 105                 110 gtt gag gat gtt cta gag gcg gat ata cgc ttc gct atg cgc tat ctc     384
Val Glu Asp Val Leu Glu Ala Asp Ile Arg Phe Ala Met Arg Tyr Leu
            115                 120                 125 ata gat cac gat cta ttt cct ttc acc tgg tac cgt gta gag gct gag     432
Ile Asp His Asp Leu Phe Pro Phe Thr Trp Tyr Arg Val Glu Ala Glu
        130                 135                 140 ccc ctc gag aac aag atg ggc ttc cgt gtc gac aag gta tac ctg gtt     480
Pro Leu Glu Asn Lys Met Gly Phe Arg Val Asp Lys Val Tyr Leu Val
145                 150                 155                 160
```

-continued

| | |
|---|---|
| aag agc agg ccg gag cca ctt tat ggt gag gct ctc gca cca acc aag<br>Lys Ser Arg Pro Glu Pro Leu Tyr Gly Glu Ala Leu Ala Pro Thr Lys<br>                165                 170                175 | 528 |
| ctt ccc gat ctt agg ata ctc gcg ttc gat att gaa gtt tat agc aag<br>Leu Pro Asp Leu Arg Ile Leu Ala Phe Asp Ile Glu Val Tyr Ser Lys<br>        180                   185                 190 | 576 |
| caa ggg tcg ccg cgt cca gag cgc gat cct gta ata gtg ata gct gtg<br>Gln Gly Ser Pro Arg Pro Glu Arg Asp Pro Val Ile Val Ile Ala Val<br>             195                 200              205 | 624 |
| aag act gac gat ggc gat gag gtg cta ttc att gca gag ggc aaa gac<br>Lys Thr Asp Asp Gly Asp Glu Val Leu Phe Ile Ala Glu Gly Lys Asp<br>210                   215                 220 | 672 |
| gat cga aaa ccg ata cgc gag ttt gta gag tac gtg aag agg tat gac<br>Asp Arg Lys Pro Ile Arg Glu Phe Val Glu Tyr Val Lys Arg Tyr Asp<br>225                   230                 235               240 | 720 |
| ccc gac ata ata gtc ggt tat aac aac aat cat ttc gat tgg cct tat<br>Pro Asp Ile Ile Val Gly Tyr Asn Asn Asn His Phe Asp Trp Pro Tyr<br>                 245                 250               255 | 768 |
| ctt ttg agg cgc gcc cgc atc cta ggc ata aag ctt gat gtg act aga<br>Leu Leu Arg Arg Ala Arg Ile Leu Gly Ile Lys Leu Asp Val Thr Arg<br>        260                   265                 270 | 816 |
| aga gtt ggc gcc gag ccc acc act agc gta cat ggg cac gtc tct gtc<br>Arg Val Gly Ala Glu Pro Thr Thr Ser Val His Gly His Val Ser Val<br>             275                 280              285 | 864 |
| cct ggc agg ctt aac gta gat ctg tac gac tat gcc gaa gag atg cca<br>Pro Gly Arg Leu Asn Val Asp Leu Tyr Asp Tyr Ala Glu Glu Met Pro<br>290                   295                 300 | 912 |
| gag atc aag ata aag agt ctc gag gag gtc gca gag tat cta ggc gtg<br>Glu Ile Lys Ile Lys Ser Leu Glu Glu Val Ala Glu Tyr Leu Gly Val<br>305                   310                 315              320 | 960 |
| atg aag aag agt gaa cgc gtt atc atc aat tgg tgg gag att cca gac<br>Met Lys Lys Ser Glu Arg Val Ile Ile Asn Trp Trp Glu Ile Pro Asp<br>                 325                 330               335 | 1008 |
| tat tgg gac gac ccg aag aag aga cca cta tta ctg caa tac gcg cgc<br>Tyr Trp Asp Asp Pro Lys Lys Arg Pro Leu Leu Leu Gln Tyr Ala Arg<br>             340                 345              350 | 1056 |
| gac gat gtc cgc gct act tac ggc tta gcc gag aag ata ttg ccg ttt<br>Asp Asp Val Arg Ala Thr Tyr Gly Leu Ala Glu Lys Ile Leu Pro Phe<br>                 355                 360              365 | 1104 |
| gct atc cag ttg tcg tac gta aca ggt ctc cca cta gac cag gta ggt<br>Ala Ile Gln Leu Ser Tyr Val Thr Gly Leu Pro Leu Asp Gln Val Gly<br>370                   375                 380 | 1152 |
| gcg atg agt gtt ggc ttt cga ctt gaa tgg tac ctg ata cgc gcg gcg<br>Ala Met Ser Val Gly Phe Arg Leu Glu Trp Tyr Leu Ile Arg Ala Ala<br>385                   390                 395              400 | 1200 |
| ttt aag atg aaa gag ctt gtg ccg aac cgc gtt gag cgc cca gaa gag<br>Phe Lys Met Lys Glu Leu Val Pro Asn Arg Val Glu Arg Pro Glu Glu<br>             405                 410              415 | 1248 |
| act tac cgt ggc gct ata gtt ctt gag ccg ttg aga ggc gtg cac gag<br>Thr Tyr Arg Gly Ala Ile Val Leu Glu Pro Leu Arg Gly Val His Glu<br>             420                 425              430 | 1296 |
| aat ata gcc gta ctc gac ttt agc tcg atg tac cca aac atc atg ata<br>Asn Ile Ala Val Leu Asp Phe Ser Ser Met Tyr Pro Asn Ile Met Ile<br>        435                   440                 445 | 1344 |
| aag tac aat gtt ggt cct gac acg ctt gtg agg cct ggt gaa aag tgt<br>Lys Tyr Asn Val Gly Pro Asp Thr Leu Val Arg Pro Gly Glu Lys Cys<br>450                   455                 460 | 1392 |
| ggc gag tgt ggt tgc tgg gag gcc ccg gag gtc aag cac agg ttc cgt<br>Gly Glu Cys Gly Cys Trp Glu Ala Pro Glu Val Lys His Arg Phe Arg<br>465                   470                 475              480 | 1440 |

-continued

| | | |
|---|---|---|
| agg tgt ccg ccc ggc ttc ttc aag aca gtt ctt gag agg ctg tta gag<br>Arg Cys Pro Pro Gly Phe Phe Lys Thr Val Leu Glu Arg Leu Leu Glu<br>485                      490                   495 | 1488 |
| ctt cgt aag cgt gtg cgt gct gaa atg aag aag tat cct ccg gat agc<br>Leu Arg Lys Arg Val Arg Ala Glu Met Lys Lys Tyr Pro Pro Asp Ser<br>500                      505                   510 | 1536 |
| cca gaa tat cga ctg ttg gat gaa agg cag aag gcg ttg aag gtt ctt<br>Pro Glu Tyr Arg Leu Leu Asp Glu Arg Gln Lys Ala Leu Lys Val Leu<br>515                      520                   525 | 1584 |
| gca aac gct agt tac ggc tac atg ggt tgg agc ggc gct agg tgg tat<br>Ala Asn Ala Ser Tyr Gly Tyr Met Gly Trp Ser Gly Ala Arg Trp Tyr<br>530                      535                   540 | 1632 |
| tgc agg gag tgc gca aag gct gtc acg gct tgg ggt agg cac ctc ata<br>Cys Arg Glu Cys Ala Lys Ala Val Thr Ala Trp Gly Arg His Leu Ile<br>545                      550                   555                   560 | 1680 |
| cgc acc gcc atc aac ata gct cgt aaa cta ggc ctc aag gtg atc tac<br>Arg Thr Ala Ile Asn Ile Ala Arg Lys Leu Gly Leu Lys Val Ile Tyr<br>                      565                   570                   575 | 1728 |
| ggt gac aca gat tcg ctc ttc gtg acc tat gat ccg gag aag gtg gaa<br>Gly Asp Thr Asp Ser Leu Phe Val Thr Tyr Asp Pro Glu Lys Val Glu<br>580                      585                   590 | 1776 |
| aat ttc atc aaa att ata aag gag gag ctg ggg ttc gaa atc aag cta<br>Asn Phe Ile Lys Ile Ile Lys Glu Glu Leu Gly Phe Glu Ile Lys Leu<br>                      595                   600                   605 | 1824 |
| gag aag gtg tac aaa cgc tta ttc ttt aca gag gct aag aag agg tac<br>Glu Lys Val Tyr Lys Arg Leu Phe Phe Thr Glu Ala Lys Lys Arg Tyr<br>610                      615                   620 | 1872 |
| gct ggc ctt ctc gag gac gga cgt ata gat att gtc ggt ttc gag gct<br>Ala Gly Leu Leu Glu Asp Gly Arg Ile Asp Ile Val Gly Phe Glu Ala<br>625                      630                   635                   640 | 1920 |
| gta cgt ggc gat tgg tgt gaa ctc gcc aag gag gtt cag act aag gtt<br>Val Arg Gly Asp Trp Cys Glu Leu Ala Lys Glu Val Gln Thr Lys Val<br>                      645                   650                   655 | 1968 |
| gtc gaa ata gta ttg aag acg agt gag gtg aac aag gct gta gag tac<br>Val Glu Ile Val Leu Lys Thr Ser Glu Val Asn Lys Ala Val Glu Tyr<br>660                      665                   670 | 2016 |
| gtc agg aag att gtg aaa gag ttg gag gag ggc aag gtt ccc ata gag<br>Val Arg Lys Ile Val Lys Glu Leu Glu Glu Gly Lys Val Pro Ile Glu<br>675                      680                   685 | 2064 |
| aag ctt gta atc tgg aag acc ctt agt aag cgt ctt gag gag tac aca<br>Lys Leu Val Ile Trp Lys Thr Leu Ser Lys Arg Leu Glu Glu Tyr Thr<br>690                      695                   700 | 2112 |
| acg gag gca cca cac gtc gtt gca gcg aag agg atg ctg tca gca ggc<br>Thr Glu Ala Pro His Val Val Ala Ala Lys Arg Met Leu Ser Ala Gly<br>705                      710                   715                   720 | 2160 |
| tac cgg gta agc cca ggc gac aag ata ggg tat gta ata gtg aag ggt<br>Tyr Arg Val Ser Pro Gly Asp Lys Ile Gly Tyr Val Ile Val Lys Gly<br>                      725                   730                   735 | 2208 |
| ggt ggc cgt atc agt caa aga gca tgg cca tac ttc atg gtc aag gat<br>Gly Gly Arg Ile Ser Gln Arg Ala Trp Pro Tyr Phe Met Val Lys Asp<br>740                      745                   750 | 2256 |
| cct agc cag ata gac gtg acc tac tat gtt gac cac caa atc atc ccg<br>Pro Ser Gln Ile Asp Val Thr Tyr Tyr Val Asp His Gln Ile Ile Pro<br>755                      760                   765 | 2304 |
| gct gca ttg aga ata ctg ggc tac ttt ggc atc acc gag aag aag ctg<br>Ala Ala Leu Arg Ile Leu Gly Tyr Phe Gly Ile Thr Glu Lys Lys Leu<br>770                      775                   780 | 2352 |
| aaa gca agt gca act ggg cag aag act ctc ttc gac ttt cta gcc aag<br>Lys Ala Ser Ala Thr Gly Gln Lys Thr Leu Phe Asp Phe Leu Ala Lys | 2400 |

```
                785               790               795               800
aag agc aag t aa                                                                    2412
Lys Ser Lys
```

<210> SEQ ID NO 4
<211> LENGTH: 803
<212> TYPE: PRT
<213> ORGANISM: Pyrolobus fumarius

<400> SEQUENCE: 4

```
Met Thr Glu Val Val Phe Thr Val Leu Asp Ser Ser Tyr Glu Val Val
 1               5                  10                  15

Gly Lys Glu Pro Gln Val Ile Ile Trp Gly Ile Ala Glu Asn Gly Glu
            20                  25                  30

Arg Val Val Leu Ile Asp Arg Ser Phe Arg Pro Tyr Phe Tyr Ala Leu
        35                  40                  45

Leu Ala Pro Gly Ala Asp Pro Lys Gln Val Ala Gln Arg Ile Arg Ala
    50                  55                  60

Leu Ser Arg Pro Lys Ser Pro Ile Ile Gly Val Glu Asp Asp Lys Arg
65                  70                  75                  80

Lys Tyr Phe Gly Arg Pro Arg Val Leu Arg Ile Arg Thr Val Leu
                85                  90                  95

Pro Glu Ala Val Arg Glu Tyr Arg Glu Leu Val Lys Asn Val Asp Gly
            100                 105                 110

Val Glu Asp Val Leu Glu Ala Asp Ile Arg Phe Ala Met Arg Tyr Leu
        115                 120                 125

Ile Asp His Asp Leu Phe Pro Phe Thr Trp Tyr Arg Val Glu Ala Glu
130                 135                 140

Pro Leu Glu Asn Lys Met Gly Phe Arg Val Asp Lys Val Tyr Leu Val
145                 150                 155                 160

Lys Ser Arg Pro Glu Pro Leu Tyr Gly Glu Ala Leu Ala Pro Thr Lys
                165                 170                 175

Leu Pro Asp Leu Arg Ile Leu Ala Phe Asp Ile Glu Val Tyr Ser Lys
            180                 185                 190

Gln Gly Ser Pro Arg Pro Glu Arg Asp Pro Val Ile Val Ile Ala Val
        195                 200                 205

Lys Thr Asp Asp Gly Asp Glu Val Leu Phe Ile Ala Glu Gly Lys Asp
    210                 215                 220

Asp Arg Lys Pro Ile Arg Glu Phe Val Glu Tyr Val Lys Arg Tyr Asp
225                 230                 235                 240

Pro Asp Ile Ile Val Gly Tyr Asn Asn Asn His Phe Asp Trp Pro Tyr
                245                 250                 255

Leu Leu Arg Arg Ala Arg Ile Leu Gly Ile Lys Leu Asp Val Thr Arg
            260                 265                 270

Arg Val Gly Ala Glu Pro Thr Thr Ser Val His Gly His Val Ser Val
        275                 280                 285

Pro Gly Arg Leu Asn Val Asp Leu Tyr Asp Tyr Ala Glu Glu Met Pro
    290                 295                 300

Glu Ile Lys Ile Lys Ser Leu Glu Glu Val Ala Glu Tyr Leu Gly Val
305                 310                 315                 320

Met Lys Lys Ser Glu Arg Val Ile Ile Asn Trp Trp Glu Ile Pro Asp
                325                 330                 335

Tyr Trp Asp Asp Pro Lys Lys Arg Pro Leu Leu Leu Gln Tyr Ala Arg
            340                 345                 350
```

-continued

```
Asp Asp Val Arg Ala Thr Tyr Gly Leu Ala Glu Lys Ile Leu Pro Phe
        355                 360                 365

Ala Ile Gln Leu Ser Tyr Val Thr Gly Leu Pro Leu Asp Gln Val Gly
        370                 375                 380

Ala Met Ser Val Gly Phe Arg Leu Glu Trp Tyr Leu Ile Arg Ala Ala
385                 390                 395                 400

Phe Lys Met Lys Glu Leu Val Pro Asn Arg Val Glu Arg Pro Glu Glu
                405                 410                 415

Thr Tyr Arg Gly Ala Ile Val Leu Glu Pro Leu Arg Gly Val His Glu
                420                 425                 430

Asn Ile Ala Val Leu Asp Phe Ser Ser Met Tyr Pro Asn Ile Met Ile
            435                 440                 445

Lys Tyr Asn Val Gly Pro Asp Thr Leu Val Arg Pro Gly Glu Lys Cys
        450                 455                 460

Gly Glu Cys Gly Cys Trp Glu Ala Pro Glu Val Lys His Arg Phe Arg
465                 470                 475                 480

Arg Cys Pro Pro Gly Phe Phe Lys Thr Val Leu Glu Arg Leu Leu Glu
                485                 490                 495

Leu Arg Lys Arg Val Arg Ala Glu Met Lys Lys Tyr Pro Pro Asp Ser
                500                 505                 510

Pro Glu Tyr Arg Leu Leu Asp Glu Arg Gln Lys Ala Leu Lys Val Leu
            515                 520                 525

Ala Asn Ala Ser Tyr Gly Tyr Met Gly Trp Ser Gly Ala Arg Trp Tyr
        530                 535                 540

Cys Arg Glu Cys Ala Lys Ala Val Thr Ala Trp Gly Arg His Leu Ile
545                 550                 555                 560

Arg Thr Ala Ile Asn Ile Ala Arg Lys Leu Gly Leu Lys Val Ile Tyr
                565                 570                 575

Gly Asp Thr Asp Ser Leu Phe Val Thr Tyr Asp Pro Glu Lys Val Glu
            580                 585                 590

Asn Phe Ile Lys Ile Ile Lys Glu Glu Leu Gly Phe Glu Ile Lys Leu
        595                 600                 605

Glu Lys Val Tyr Lys Arg Leu Phe Phe Thr Glu Ala Lys Lys Arg Tyr
    610                 615                 620

Ala Gly Leu Leu Glu Asp Gly Arg Ile Asp Ile Val Gly Phe Glu Ala
625                 630                 635                 640

Val Arg Gly Asp Trp Cys Glu Leu Ala Lys Glu Val Gln Thr Lys Val
                645                 650                 655

Val Glu Ile Val Leu Lys Thr Ser Glu Val Asn Lys Ala Val Glu Tyr
            660                 665                 670

Val Arg Lys Ile Val Lys Glu Leu Glu Glu Gly Lys Val Pro Ile Glu
        675                 680                 685

Lys Leu Val Ile Trp Lys Thr Leu Ser Lys Arg Leu Glu Glu Tyr Thr
    690                 695                 700

Thr Glu Ala Pro His Val Val Ala Ala Lys Arg Met Leu Ser Ala Gly
705                 710                 715                 720

Tyr Arg Val Ser Pro Gly Asp Lys Ile Gly Tyr Val Ile Val Lys Gly
                725                 730                 735

Gly Gly Arg Ile Ser Gln Arg Ala Trp Pro Tyr Phe Met Val Lys Asp
            740                 745                 750

Pro Ser Gln Ile Asp Val Thr Tyr Tyr Val Asp His Gln Ile Ile Pro
        755                 760                 765

Ala Ala Leu Arg Ile Leu Gly Tyr Phe Gly Ile Thr Glu Lys Lys Leu
```

```
                         770                775                780
Lys Ala Ser Ala Thr Gly Gln Lys Thr Leu Phe Asp Phe Leu Ala Lys
785                 790                795                800

Lys Ser Lys

<210> SEQ ID NO 5
<211> LENGTH: 2367
<212> TYPE: DNA
<213> ORGANISM: Archaeoglobus lithotrophicus
<220> FEATURE:
<221> NAME/KEY: CDS
<222> LOCATION: (1)...(2364)

<400> SEQUENCE: 5 atg ata aag gtc aag ggc tgg ctg ctc gat gca gat tat atc acc gaa        48
Met Ile Lys Val Lys Gly Trp Leu Leu Asp Ala Asp Tyr Ile Thr Glu
 1               5                  10                  15 aac gat cga gcc gtt ata agg cta tgg tgt aag gat gag gaa gga ata        96
Asn Asp Arg Ala Val Ile Arg Leu Trp Cys Lys Asp Glu Glu Gly Ile
             20                  25                  30 ttt atc gca tac gat cac tca ttc cag ccc tac ttt tac gca ctc aaa       144
Phe Ile Ala Tyr Asp His Ser Phe Gln Pro Tyr Phe Tyr Ala Leu Lys
         35                  40                  45 gaa gag ggt atc act gcc gaa gat ata gtg aaa ata aag gtt caa acg       192
Glu Glu Gly Ile Thr Ala Glu Asp Ile Val Lys Ile Lys Val Gln Thr
     50                  55                  60 aaa aaa gaa gta att acg ccg tta aaa gtt gag gaa acc aca gcc aaa       240
Lys Lys Glu Val Ile Thr Pro Leu Lys Val Glu Glu Thr Thr Ala Lys
 65                  70                  75                  80 aat ctt ggt agg gag gtt gaa gtt ttc aag ata tat gca aga cac cct       288
Asn Leu Gly Arg Glu Val Glu Val Phe Lys Ile Tyr Ala Arg His Pro
                 85                  90                  95 cag cac gtc ccc aaa ctt cgt gag gtt gtt tcg cag tat ctg gag att       336
Gln His Val Pro Lys Leu Arg Glu Val Val Ser Gln Tyr Leu Glu Ile
            100                 105                 110 agg gag gca gac ata cct ttt gcc tat cga tac ctc ata gat aaa aat       384
Arg Glu Ala Asp Ile Pro Phe Ala Tyr Arg Tyr Leu Ile Asp Lys Asn
        115                 120                 125 ctt gcg tgt atg gat gga gtt gta att gaa ggc gtt gaa aga cgt gag       432
Leu Ala Cys Met Asp Gly Val Val Ile Glu Gly Val Glu Arg Arg Glu
    130                 135                 140 aag ggg ttg aga tgt tac gaa atc aag aga ata gaa aga gat tcc aga       480
Lys Gly Leu Arg Cys Tyr Glu Ile Lys Arg Ile Glu Arg Asp Ser Arg
145                 150                 155                 160 cag gat ttt ccc gaa ctc aag gtt atg gcg ttt gat tgc gaa atg ctc       528
Gln Asp Phe Pro Glu Leu Lys Val Met Ala Phe Asp Cys Glu Met Leu
                165                 170                 175 tca gag gtt ggt atg ccc gat cca gag aaa gat cct atc ata gtc ata       576
Ser Glu Val Gly Met Pro Asp Pro Glu Lys Asp Pro Ile Ile Val Ile
            180                 185                 190 tca att aaa tcg ggt gaa tac gag gaa atc ctc aac ggt gat aac gag       624
Ser Ile Lys Ser Gly Glu Tyr Glu Glu Ile Leu Asn Gly Asp Asn Glu
        195                 200                 205 aga gaa ttg ctt acc aga ttt gtc aag ata att cgc gat att gat ccc       672
Arg Glu Leu Leu Thr Arg Phe Val Lys Ile Ile Arg Asp Ile Asp Pro
    210                 215                 220 gac att ata gtt gga tac aat cag gac agc ttt gac tgg ccc tat atc       720
Asp Ile Ile Val Gly Tyr Asn Gln Asp Ser Phe Asp Trp Pro Tyr Ile
225                 230                 235                 240 aag aag aga gct gag aaa ctg agg gtt aag ctt gac atc gga aga gat       768
```

```
Lys Lys Arg Ala Glu Lys Leu Arg Val Lys Leu Asp Ile Gly Arg Asp
            245                 250                 255 aga agc gaa ctg gct atc agg gga gga aga cca aag att gct ggc agg       816
Arg Ser Glu Leu Ala Ile Arg Gly Gly Arg Pro Lys Ile Ala Gly Arg
        260                 265                 270 ttg aac gtg gat ctc tat gat att gca atg agg agt ctc gat gta aag       864
Leu Asn Val Asp Leu Tyr Asp Ile Ala Met Arg Ser Leu Asp Val Lys
                275                 280                 285 gtg aag aag ctc gaa aac gtt gca gag ttt ctg ggt aag aaa ata gag       912
Val Lys Lys Leu Glu Asn Val Ala Glu Phe Leu Gly Lys Lys Ile Glu
        290                 295                 300 ctt gca gat att gaa gcg aag gat atc tac aag cac tgg aca tcg ggc       960
Leu Ala Asp Ile Glu Ala Lys Asp Ile Tyr Lys His Trp Thr Ser Gly
305                 310                 315                 320 gac agg gaa agc gta atc aaa tac tcc cgg cag gac atc ctg cac acg      1008
Asp Arg Glu Ser Val Ile Lys Tyr Ser Arg Gln Asp Ile Leu His Thr
                325                 330                 335 tac ttc ata gct gaa gaa ttg ctg cca atg cat tac gaa ctt tcc aga      1056
Tyr Phe Ile Ala Glu Glu Leu Leu Pro Met His Tyr Glu Leu Ser Arg
                340                 345                 350 atg ata cgc ata cct ctc gat gat gtg aca agg agc ggg aga ggt aag      1104
Met Ile Arg Ile Pro Leu Asp Asp Val Thr Arg Ser Gly Arg Gly Lys
        355                 360                 365 cag gtt gag tgg ctg ctg tta agc gaa gca cac aaa ctt ggc gaa ctt      1152
Gln Val Glu Trp Leu Leu Leu Ser Glu Ala His Lys Leu Gly Glu Leu
370                 375                 380 gca ccc aac ccc aga gag atg gcc gac agc tat gaa gga gca ttc gtg      1200
Ala Pro Asn Pro Arg Glu Met Ala Asp Ser Tyr Glu Gly Ala Phe Val
385                 390                 395                 400 ctc gag ccc gca aga gga ttg cat gag aac gta atc tgc ctg gac ttt      1248
Leu Glu Pro Ala Arg Gly Leu His Glu Asn Val Ile Cys Leu Asp Phe
                405                 410                 415 gcg tcc atg tat ccc tca ata atg att tca tac aac atc agc ccc gac      1296
Ala Ser Met Tyr Pro Ser Ile Met Ile Ser Tyr Asn Ile Ser Pro Asp
                420                 425                 430 acg ctt gta ata ggc aaa tgc gac gat tgc aat gta gcg ccg gag gtg      1344
Thr Leu Val Ile Gly Lys Cys Asp Asp Cys Asn Val Ala Pro Glu Val
            435                 440                 445 ggg cac aaa ttc agg aaa cat cct gat ggt ttt ttc aaa aga ata ctc      1392
Gly His Lys Phe Arg Lys His Pro Asp Gly Phe Phe Lys Arg Ile Leu
        450                 455                 460 aaa atg ctg att gag aaa aga aga gaa ata aag aag gtt atg aaa aca      1440
Lys Met Leu Ile Glu Lys Arg Arg Glu Ile Lys Lys Val Met Lys Thr
465                 470                 475                 480 ctt gac tac aac tcg cca gaa tac aag ctg ctc gat ata aag cag gca      1488
Leu Asp Tyr Asn Ser Pro Glu Tyr Lys Leu Leu Asp Ile Lys Gln Ala
                485                 490                 495 acg ctg aaa gtt ctt aca aac tcg ttt tac ggt tat act ggg tgg agt      1536
Thr Leu Lys Val Leu Thr Asn Ser Phe Tyr Gly Tyr Thr Gly Trp Ser
                500                 505                 510 ctt gcg aga tgg tac tgc aag gag tgc gct gaa gct aca acg gca tgg      1584
Leu Ala Arg Trp Tyr Cys Lys Glu Cys Ala Glu Ala Thr Thr Ala Trp
        515                 520                 525 ggc aga cac ttt atc aaa aca tct gca aga att gcg aaa gag ctt gga      1632
Gly Arg His Phe Ile Lys Thr Ser Ala Arg Ile Ala Lys Glu Leu Gly
            530                 535                 540 ttt gaa gtg cta tat ggg gat aca gat agc atc ttt gtt aaa aaa gat      1680
Phe Glu Val Leu Tyr Gly Asp Thr Asp Ser Ile Phe Val Lys Lys Asp
545                 550                 555                 560
```

```
gga ttg agc ctg gaa gag ctc aaa aaa gaa gtt aaa aag ctc ata ggt      1728
Gly Leu Ser Leu Glu Glu Leu Lys Lys Glu Val Lys Lys Leu Ile Gly
                565                 570                 575 aaa ctt tcg gaa gag atg cca ata caa ata gag ata gat gaa tac tac      1776
Lys Leu Ser Glu Glu Met Pro Ile Gln Ile Glu Ile Asp Glu Tyr Tyr
            580                 585                 590 gag aca ata ttc ttc gtt gaa aag aaa agg tat gct gga ttg aca cag      1824
Glu Thr Ile Phe Phe Val Glu Lys Lys Arg Tyr Ala Gly Leu Thr Gln
        595                 600                 605 gat gga aga ata att gta aag ggt ctt gaa gtc aga aga ggc gac tgg      1872
Asp Gly Arg Ile Ile Val Lys Gly Leu Glu Val Arg Arg Gly Asp Trp
    610                 615                 620 tgc gag ctt gca aag aag ata cag aaa ggt gta ata gaa atc att ctg      1920
Cys Glu Leu Ala Lys Lys Ile Gln Lys Gly Val Ile Glu Ile Ile Leu
625                 630                 635                 640 aag gaa aag aat cct gaa aaa gct gct gag tat gtg aaa gga gtc ata      1968
Lys Glu Lys Asn Pro Glu Lys Ala Ala Glu Tyr Val Lys Gly Val Ile
                645                 650                 655 gag gag ata aag gca ggc aaa att ccg ctt gaa gat tat atc atc tac      2016
Glu Glu Ile Lys Ala Gly Lys Ile Pro Leu Glu Asp Tyr Ile Ile Tyr
            660                 665                 670 aag gga ttg acg aga aaa cca tca aag tac gag agt atg cag gct cac      2064
Lys Gly Leu Thr Arg Lys Pro Ser Lys Tyr Glu Ser Met Gln Ala His
        675                 680                 685 gta aaa gct gcc atg aag gcg gca aag aga gga ata gta tac aca atc      2112
Val Lys Ala Ala Met Lys Ala Ala Lys Arg Gly Ile Val Tyr Thr Ile
    690                 695                 700 ggc tca aag gtt ggt ttt gtc gtt aca aaa ggt gtg ggg aac ata ggt      2160
Gly Ser Lys Val Gly Phe Val Val Thr Lys Gly Val Gly Asn Ile Gly
705                 710                 715                 720 gat agg gct ttt cca tct gat ctg ata gag gac ttt gac ggt gaa gtg      2208
Asp Arg Ala Phe Pro Ser Asp Leu Ile Glu Asp Phe Asp Gly Glu Val
                725                 730                 735 atc aca gat ctt gac gga aac aag tac aag atc gac aag gaa tac tat      2256
Ile Thr Asp Leu Asp Gly Asn Lys Tyr Lys Ile Asp Lys Glu Tyr Tyr
            740                 745                 750 ata gac cat cag gta ctg cca tcg gtt ctt cga att ctc gag agg ttc      2304
Ile Asp His Gln Val Leu Pro Ser Val Leu Arg Ile Leu Glu Arg Phe
        755                 760                 765 gga tac acc gag gca cag cta aaa ggt gct gcg gag cag caa acg cta      2352
Gly Tyr Thr Glu Ala Gln Leu Lys Gly Ala Ala Glu Gln Gln Thr Leu
    770                 775                 780 gat gct ttc tgg taa                                                  2367
Asp Ala Phe Trp
785

<210> SEQ ID NO 6
<211> LENGTH: 788
<212> TYPE: PRT
<213> ORGANISM: Archaeoglobus lithotrophicus

<400> SEQUENCE: 6

Met Ile Lys Val Lys Gly Trp Leu Leu Asp Ala Asp Tyr Ile Thr Glu
 1               5                  10                  15

Asn Asp Arg Ala Val Ile Arg Leu Trp Cys Lys Asp Glu Glu Gly Ile
            20                  25                  30

Phe Ile Ala Tyr Asp His Ser Phe Gln Pro Tyr Phe Tyr Ala Leu Lys
        35                  40                  45

Glu Glu Gly Ile Thr Ala Glu Asp Ile Val Lys Ile Lys Val Gln Thr
    50                  55                  60
```

-continued

```
Lys Lys Glu Val Ile Thr Pro Leu Lys Val Glu Thr Thr Ala Lys
 65                  70                  75                  80

Asn Leu Gly Arg Glu Val Glu Val Phe Lys Ile Tyr Ala Arg His Pro
             85                  90                  95

Gln His Val Pro Lys Leu Arg Glu Val Val Ser Gln Tyr Leu Glu Ile
            100                 105                 110

Arg Glu Ala Asp Ile Pro Phe Ala Tyr Arg Tyr Leu Ile Asp Lys Asn
        115                 120                 125

Leu Ala Cys Met Asp Gly Val Ile Glu Gly Val Glu Arg Arg Glu
130                 135                 140

Lys Gly Leu Arg Cys Tyr Glu Ile Lys Arg Ile Glu Arg Asp Ser Arg
145                 150                 155                 160

Gln Asp Phe Pro Glu Leu Lys Val Met Ala Phe Asp Cys Glu Met Leu
                165                 170                 175

Ser Glu Val Gly Met Pro Asp Pro Glu Lys Asp Pro Ile Ile Val Ile
            180                 185                 190

Ser Ile Lys Ser Gly Glu Tyr Glu Glu Ile Leu Asn Gly Asp Asn Glu
        195                 200                 205

Arg Glu Leu Leu Thr Arg Phe Val Lys Ile Ile Arg Asp Ile Asp Pro
210                 215                 220

Asp Ile Ile Val Gly Tyr Asn Gln Asp Ser Phe Asp Trp Pro Tyr Ile
225                 230                 235                 240

Lys Lys Arg Ala Glu Lys Leu Arg Val Lys Leu Asp Ile Gly Arg Asp
                245                 250                 255

Arg Ser Glu Leu Ala Ile Arg Gly Gly Arg Pro Lys Ile Ala Gly Arg
            260                 265                 270

Leu Asn Val Asp Leu Tyr Asp Ile Ala Met Arg Ser Leu Asp Val Lys
        275                 280                 285

Val Lys Lys Leu Glu Asn Val Ala Glu Phe Leu Gly Lys Lys Ile Glu
290                 295                 300

Leu Ala Asp Ile Glu Ala Lys Asp Ile Tyr Lys His Trp Thr Ser Gly
305                 310                 315                 320

Asp Arg Glu Ser Val Ile Lys Tyr Ser Arg Gln Asp Ile Leu His Thr
                325                 330                 335

Tyr Phe Ile Ala Glu Glu Leu Leu Pro Met His Tyr Glu Leu Ser Arg
            340                 345                 350

Met Ile Arg Ile Pro Leu Asp Asp Val Thr Arg Ser Gly Arg Gly Lys
        355                 360                 365

Gln Val Glu Trp Leu Leu Leu Ser Glu Ala His Lys Leu Gly Glu Leu
370                 375                 380

Ala Pro Asn Pro Arg Glu Met Ala Asp Ser Tyr Glu Gly Ala Phe Val
385                 390                 395                 400

Leu Glu Pro Ala Arg Gly Leu His Glu Asn Val Ile Cys Leu Asp Phe
                405                 410                 415

Ala Ser Met Tyr Pro Ser Ile Met Ile Ser Tyr Asn Ile Ser Pro Asp
            420                 425                 430

Thr Leu Val Ile Gly Lys Cys Asp Asp Cys Asn Val Ala Pro Glu Val
        435                 440                 445

Gly His Lys Phe Arg Lys His Pro Asp Gly Phe Phe Lys Arg Ile Leu
450                 455                 460

Lys Met Leu Ile Glu Lys Arg Arg Glu Ile Lys Lys Val Met Lys Thr
465                 470                 475                 480
```

```
Leu Asp Tyr Asn Ser Pro Glu Tyr Lys Leu Asp Ile Lys Gln Ala
                485                 490                 495

Thr Leu Lys Val Leu Thr Asn Ser Phe Tyr Gly Tyr Thr Gly Trp Ser
            500                 505                 510

Leu Ala Arg Trp Tyr Cys Lys Glu Cys Ala Glu Ala Thr Thr Ala Trp
            515                 520                 525

Gly Arg His Phe Ile Lys Thr Ser Ala Arg Ile Ala Lys Glu Leu Gly
        530                 535                 540

Phe Glu Val Leu Tyr Gly Asp Thr Asp Ser Ile Phe Val Lys Lys Asp
545                 550                 555                 560

Gly Leu Ser Leu Glu Glu Leu Lys Lys Glu Val Lys Lys Leu Ile Gly
                565                 570                 575

Lys Leu Ser Glu Glu Met Pro Ile Gln Ile Glu Ile Asp Glu Tyr Tyr
            580                 585                 590

Glu Thr Ile Phe Phe Val Glu Lys Lys Arg Tyr Ala Gly Leu Thr Gln
        595                 600                 605

Asp Gly Arg Ile Ile Val Lys Gly Leu Glu Val Arg Arg Gly Asp Trp
610                 615                 620

Cys Glu Leu Ala Lys Lys Ile Gln Lys Gly Val Ile Glu Ile Ile Leu
625                 630                 635                 640

Lys Glu Lys Asn Pro Glu Lys Ala Ala Glu Tyr Val Lys Gly Val Ile
                645                 650                 655

Glu Glu Ile Lys Ala Gly Lys Ile Pro Leu Glu Asp Tyr Ile Ile Tyr
            660                 665                 670

Lys Gly Leu Thr Arg Lys Pro Ser Lys Tyr Glu Ser Met Gln Ala His
        675                 680                 685

Val Lys Ala Ala Met Lys Ala Ala Lys Arg Gly Ile Val Tyr Thr Ile
690                 695                 700

Gly Ser Lys Val Gly Phe Val Thr Lys Gly Val Gly Asn Ile Gly
705                 710                 715                 720

Asp Arg Ala Phe Pro Ser Asp Leu Ile Glu Asp Phe Asp Gly Glu Val
                725                 730                 735

Ile Thr Asp Leu Asp Gly Asn Lys Tyr Lys Ile Asp Lys Glu Tyr Tyr
            740                 745                 750

Ile Asp His Gln Val Leu Pro Ser Val Leu Arg Ile Leu Glu Arg Phe
        755                 760                 765

Gly Tyr Thr Glu Ala Gln Leu Lys Gly Ala Ala Glu Gln Gln Thr Leu
770                 775                 780

Asp Ala Phe Trp
785

<210> SEQ ID NO 7
<211> LENGTH: 2634
<212> TYPE: DNA
<213> ORGANISM: Metallosphaera prunae
<220> FEATURE:
<221> NAME/KEY: CDS
<222> LOCATION: (1)...(2631)

<400> SEQUENCE: 7 atg agt ata atg gcc aga cag ctt acc ctt gct gac ttc tct ggg atc    48
Met Ser Ile Met Ala Arg Gln Leu Thr Leu Ala Asp Phe Ser Gly Ile
  1               5                  10                  15 aag aga gag gaa cca gtt aaa cag gaa gag aag acg cag gag gaa gag    96
Lys Arg Glu Glu Pro Val Lys Gln Glu Glu Lys Thr Gln Glu Glu Glu
                 20                  25                  30
```

-continued

| | |
|---|---|
| agg cct ctg gaa agg cca gcg agg cta aga aag gac aca gtt aaa cag<br>Arg Pro Leu Glu Arg Pro Ala Arg Leu Arg Lys Asp Thr Val Lys Gln<br>35                    40                    45 | 144 |
| gcg cag gag gag aga aag tac ttt ctt ctc tcc gta gac tat gat ggt<br>Ala Gln Glu Glu Arg Lys Tyr Phe Leu Leu Ser Val Asp Tyr Asp Gly<br>50                    55                    60 | 192 |
| aaa atg ggg aag gct gtc tgc aag ctt tat gat cct gaa acg ggt gag<br>Lys Met Gly Lys Ala Val Cys Lys Leu Tyr Asp Pro Glu Thr Gly Glu<br>65                       70                    75                    80 | 240 |
| cta cac gtc ctt tac gac agc acg ggt cac aag tca tac ttc ctt gtg<br>Leu His Val Leu Tyr Asp Ser Thr Gly His Lys Ser Tyr Phe Leu Val<br>85                     90                    95 | 288 |
| gat tta gag cca gat cag atc caa aaa att cca aag att gtt aag gat<br>Asp Leu Glu Pro Asp Gln Ile Gln Lys Ile Pro Lys Ile Val Lys Asp<br>100                   105                 110 | 336 |
| gag tcc ttt gtt agg ctt gag aag acc act aaa ata gac ccc tac act<br>Glu Ser Phe Val Arg Leu Glu Lys Thr Thr Lys Ile Asp Pro Tyr Thr<br>115                 120                 125 | 384 |
| tgg aaa cct att aac cta acc aag att gtg gtg aat gac ccc ctc gct<br>Trp Lys Pro Ile Asn Leu Thr Lys Ile Val Val Asn Asp Pro Leu Ala<br>130                   135                 140 | 432 |
| gtg aga cgc cta aga gaa tat gtc cca agg gcc tat gaa gct cat ata<br>Val Arg Arg Leu Arg Glu Tyr Val Pro Arg Ala Tyr Glu Ala His Ile<br>145                   150                 155                 160 | 480 |
| aaa tat ttt aac aat tat att tac gat ttc agc ctc ata cca ggg atg<br>Lys Tyr Phe Asn Asn Tyr Ile Tyr Asp Phe Ser Leu Ile Pro Gly Met<br>                    165                 170                 175 | 528 |
| ccc tac gtg gta aag aag ggg aag cta gtc ccc ctt aag ccg gag gtt<br>Pro Tyr Val Val Lys Lys Gly Lys Leu Val Pro Leu Lys Pro Glu Val<br>                    180                 185                 190 | 576 |
| gac gtc aaa gag gta aag gaa gcg ttc aag gat gct gac cag ata gct<br>Asp Val Lys Glu Val Lys Glu Ala Phe Lys Asp Ala Asp Gln Ile Ala<br>                    195                 200                 205 | 624 |
| caa gag atg gcg cta gac tgg gct ccc ctc ttt gag tcc gag att ccg<br>Gln Glu Met Ala Leu Asp Trp Ala Pro Leu Phe Glu Ser Glu Ile Pro<br>210                   215                 220 | 672 |
| tcg gtg aag agg gtc gca ata gat ata gag gtt tat act ccc atg atg<br>Ser Val Lys Arg Val Ala Ile Asp Ile Glu Val Tyr Thr Pro Met Met<br>225                   230                 235                 240 | 720 |
| ggt agg gta ccg gat cca gta aag gcc gag tac ccc gtg ata agc gta<br>Gly Arg Val Pro Asp Pro Val Lys Ala Glu Tyr Pro Val Ile Ser Val<br>                    245                 250                 255 | 768 |
| gcc cta gca ggg agc gat ggc ctg aaa ctg gtc cta gtc ctt gat agg<br>Ala Leu Ala Gly Ser Asp Gly Leu Lys Leu Val Leu Val Leu Asp Arg<br>                    260                 265                 270 | 816 |
| gga gat agt ccg att caa agt aag gat atc aag gtt gag gtc ttc cgc<br>Gly Asp Ser Pro Ile Gln Ser Lys Asp Ile Lys Val Glu Val Phe Arg<br>275                   280                 285 | 864 |
| aca gag agg gag ctt ctc tcc agg ttg ttt gac att ctt aag gaa tat<br>Thr Glu Arg Glu Leu Leu Ser Arg Leu Phe Asp Ile Leu Lys Glu Tyr<br>290                   295                 300 | 912 |
| ccc atg gtt ctg acc ttt aac gga gac gac ttc gat atc cca tac ctg<br>Pro Met Val Leu Thr Phe Asn Gly Asp Asp Phe Asp Ile Pro Tyr Leu<br>305                   310                 315                 320 | 960 |
| atc ttc aga ggt ttc aag ctc ggg tta cta cag gat gag ata ccc ttc<br>Ile Phe Arg Gly Phe Lys Leu Gly Leu Leu Gln Asp Glu Ile Pro Phe<br>                    325                 330                 335 | 1008 |
| gag atc tct agt ttt ggc agg aaa cct gac gcg aag ttc aga tat gga<br>Glu Ile Ser Ser Phe Gly Arg Lys Pro Asp Ala Lys Phe Arg Tyr Gly<br>                    340                 345                 350 | 1056 |

```
ttt cac ata gat ttg tac agg ttc ttc ttc aac aag gcg gtc agg aac    1104
Phe His Ile Asp Leu Tyr Arg Phe Phe Phe Asn Lys Ala Val Arg Asn
        355                 360                 365 tat gca ttt gag ggg aag tac tca gag tac aac ctt gac acc gta gcc    1152
Tyr Ala Phe Glu Gly Lys Tyr Ser Glu Tyr Asn Leu Asp Thr Val Ala
    370                 375                 380 cag gca ctc ttg ggt ctc tcc aag gtc aag ttg gac gag tcc att agc    1200
Gln Ala Leu Leu Gly Leu Ser Lys Val Lys Leu Asp Glu Ser Ile Ser
385                 390                 395                 400 gac cta aac atg tct aaa ctc gtg gag tac aac tac agg gac tcg gag    1248
Asp Leu Asn Met Ser Lys Leu Val Glu Tyr Asn Tyr Arg Asp Ser Glu
            405                 410                 415 atc acg ctg aag ttg acc acg ttc aac aac gaa cta gta tgg aag ttg    1296
Ile Thr Leu Lys Leu Thr Thr Phe Asn Asn Glu Leu Val Trp Lys Leu
        420                 425                 430 att gta ctc ttc tcc aga att tcc aag ctt ggt ata gag gag cta act    1344
Ile Val Leu Phe Ser Arg Ile Ser Lys Leu Gly Ile Glu Glu Leu Thr
    435                 440                 445 agg aca gag ata tca gcc tgg gta aag aac ctg tac tac tgg gaa cat    1392
Arg Thr Glu Ile Ser Ala Trp Val Lys Asn Leu Tyr Tyr Trp Glu His
450                 455                 460 agg aaa agg aac tgg tta atc ccc ctc aag gag gaa atc ctt gaa cgc    1440
Arg Lys Arg Asn Trp Leu Ile Pro Leu Lys Glu Glu Ile Leu Glu Arg
465                 470                 475                 480 tcc tct ggg ttg aag aca gct gcc att atc aag gga aag gga tac aag    1488
Ser Ser Gly Leu Lys Thr Ala Ala Ile Ile Lys Gly Lys Gly Tyr Lys
            485                 490                 495 ggc gca gtg gtc ata gac cca cct gtg ggg gtt tac ttt gac gta gtt    1536
Gly Ala Val Val Ile Asp Pro Pro Val Gly Val Tyr Phe Asp Val Val
        500                 505                 510 gtt ctg gac ttc gcc tca ctg tat ccc tcc atc atc agg aac tgg aac    1584
Val Leu Asp Phe Ala Ser Leu Tyr Pro Ser Ile Ile Arg Asn Trp Asn
    515                 520                 525 ctc agt tat gaa acc gtt gat gtg aag gaa tgt aac aag aaa agg gat    1632
Leu Ser Tyr Glu Thr Val Asp Val Lys Glu Cys Asn Lys Lys Arg Asp
530                 535                 540 ata agg gat gag agt ggg gcg aaa atc cat gag gtg tgc gtg gac agg    1680
Ile Arg Asp Glu Ser Gly Ala Lys Ile His Glu Val Cys Val Asp Arg
545                 550                 555                 560 ccc ggg att act gca gtg gta act ggc tta ctt agg gac ttc agg gtc    1728
Pro Gly Ile Thr Ala Val Val Thr Gly Leu Leu Arg Asp Phe Arg Val
            565                 570                 575 aaa att tac aag aag aaa ggg aaa cag agc aac ata gac gag gag aga    1776
Lys Ile Tyr Lys Lys Lys Gly Lys Gln Ser Asn Ile Asp Glu Glu Arg
        580                 585                 590 aag atg ttg tac gac gtg gta cag agg ggc atg aag gtg ttc att aat    1824
Lys Met Leu Tyr Asp Val Val Gln Arg Gly Met Lys Val Phe Ile Asn
    595                 600                 605 gcg acc tat ggc gtc ttc ggt gcg gag acc ttc ccc ttg tac gcc cca    1872
Ala Thr Tyr Gly Val Phe Gly Ala Glu Thr Phe Pro Leu Tyr Ala Pro
610                 615                 620 gca gtt gca gag agc gtt aca gcc cta ggt agg tac gta atc acg tcc    1920
Ala Val Ala Glu Ser Val Thr Ala Leu Gly Arg Tyr Val Ile Thr Ser
625                 630                 635                 640 acc aag gaa atg gct aac aag ctt ggg ctg aag gtt gtg tac ggg gat    1968
Thr Lys Glu Met Ala Asn Lys Leu Gly Leu Lys Val Val Tyr Gly Asp
            645                 650                 655 acg gac tcg ctc ttc att cac cag cct gat aag aag aag ctg gag gaa    2016
Thr Asp Ser Leu Phe Ile His Gln Pro Asp Lys Lys Lys Leu Glu Glu
```

-continued

```
                660                 665                 670
ctg gtg gag tgg acc agg cag aac ttc ggg ctt gat cta gag gtg gac      2064
Leu Val Glu Trp Thr Arg Gln Asn Phe Gly Leu Asp Leu Glu Val Asp
            675                 680                 685 aaa act tac agg ttc att gcc ttc tcc ggt ctt aag aag aac tac ttc      2112
Lys Thr Tyr Arg Phe Ile Ala Phe Ser Gly Leu Lys Lys Asn Tyr Phe
690                 695                 700 ggt gtg ttc aag gat tcc aag gtt gac ata aag ggc atg ttg gca aag      2160
Gly Val Phe Lys Asp Ser Lys Val Asp Ile Lys Gly Met Leu Ala Lys
705                 710                 715                 720 aag agg aac acc cca gag ttt ctg aag cag gcc ttc aat gag gct aag      2208
Lys Arg Asn Thr Pro Glu Phe Leu Lys Gln Ala Phe Asn Glu Ala Lys
            725                 730                 735 gag agg cta gcg aag gtt cag aac cag gag gag ctc gaa aag gca att      2256
Glu Arg Leu Ala Lys Val Gln Asn Gln Glu Glu Leu Glu Lys Ala Ile
            740                 745                 750 caa gac tta acg gcg cag gtt aag gag gtg tac agg aag ctt aag atg      2304
Gln Asp Leu Thr Ala Gln Val Lys Glu Val Tyr Arg Lys Leu Lys Met
            755                 760                 765 aag gaa tat aac ttg gat gag ctc gcc ttc agg gtc atg tta tcc agg      2352
Lys Glu Tyr Asn Leu Asp Glu Leu Ala Phe Arg Val Met Leu Ser Arg
            770                 775                 780 gac gtg aag tcc tat gag aag aac acc cca cag cac gtt aag gct gcg      2400
Asp Val Lys Ser Tyr Glu Lys Asn Thr Pro Gln His Val Lys Ala Ala
785                 790                 795                 800 gca cag ctg gcg gag atg aac gta caa gtg atg tca agg gat ata att      2448
Ala Gln Leu Ala Glu Met Asn Val Gln Val Met Ser Arg Asp Ile Ile
            805                 810                 815 agc ttc gta aag gta aag act aag gag gga gtt aaa cct gtc cag cta      2496
Ser Phe Val Lys Val Lys Thr Lys Glu Gly Val Lys Pro Val Gln Leu
            820                 825                 830 gct aag ctt tca gag att gat gtg gat aaa tac tat gag agc gtg aga      2544
Ala Lys Leu Ser Glu Ile Asp Val Asp Lys Tyr Tyr Glu Ser Val Arg
            835                 840                 845 agt acc ttc gaa cag tta ttg aaa agc ttc aat gtg agc tgg gat aga      2592
Ser Thr Phe Glu Gln Leu Leu Lys Ser Phe Asn Val Ser Trp Asp Arg
            850                 855                 860 ata gag tcc acg aca tca atc gac tcg ttc ttc aag act tag              2634
Ile Glu Ser Thr Thr Ser Ile Asp Ser Phe Phe Lys Thr
865                 870                 875
```

<210> SEQ ID NO 8
<211> LENGTH: 877
<212> TYPE: PRT
<213> ORGANISM: Metallosphaera prunae

<400> SEQUENCE: 8

```
Met Ser Ile Met Ala Arg Gln Leu Thr Leu Ala Asp Phe Ser Gly Ile
1               5                   10                  15

Lys Arg Glu Glu Pro Val Lys Gln Glu Glu Lys Thr Gln Glu Glu Glu
            20                  25                  30

Arg Pro Leu Glu Arg Pro Ala Arg Leu Arg Lys Asp Thr Val Lys Gln
        35                  40                  45

Ala Gln Glu Glu Arg Lys Tyr Phe Leu Leu Ser Val Asp Tyr Asp Gly
    50                  55                  60

Lys Met Gly Lys Ala Val Cys Lys Leu Tyr Asp Pro Glu Thr Gly Glu
65                  70                  75                  80

Leu His Val Leu Tyr Asp Ser Thr Gly His Lys Ser Tyr Phe Leu Val
                85                  90                  95
```

-continued

```
Asp Leu Glu Pro Asp Gln Ile Gln Lys Ile Pro Lys Ile Val Lys Asp
            100                 105                 110
Glu Ser Phe Val Arg Leu Glu Lys Thr Thr Lys Ile Asp Pro Tyr Thr
        115                 120                 125
Trp Lys Pro Ile Asn Leu Thr Lys Ile Val Asn Asp Pro Leu Ala
130                 135                 140
Val Arg Arg Leu Arg Glu Tyr Val Pro Arg Ala Tyr Glu Ala His Ile
145                 150                 155                 160
Lys Tyr Phe Asn Asn Tyr Ile Tyr Asp Phe Ser Leu Ile Pro Gly Met
                165                 170                 175
Pro Tyr Val Val Lys Lys Gly Lys Leu Val Pro Leu Lys Pro Glu Val
            180                 185                 190
Asp Val Lys Glu Val Lys Glu Ala Phe Lys Asp Ala Asp Gln Ile Ala
        195                 200                 205
Gln Glu Met Ala Leu Asp Trp Ala Pro Leu Phe Glu Ser Glu Ile Pro
    210                 215                 220
Ser Val Lys Arg Val Ala Ile Asp Ile Glu Val Tyr Thr Pro Met Met
225                 230                 235                 240
Gly Arg Val Pro Asp Pro Val Lys Ala Glu Tyr Pro Val Ile Ser Val
                245                 250                 255
Ala Leu Ala Gly Ser Asp Gly Leu Lys Leu Val Leu Val Leu Asp Arg
            260                 265                 270
Gly Asp Ser Pro Ile Gln Ser Lys Asp Ile Lys Val Glu Val Phe Arg
        275                 280                 285
Thr Glu Arg Glu Leu Leu Ser Arg Leu Phe Asp Ile Leu Lys Glu Tyr
    290                 295                 300
Pro Met Val Leu Thr Phe Asn Gly Asp Asp Phe Asp Ile Pro Tyr Leu
305                 310                 315                 320
Ile Phe Arg Gly Phe Lys Leu Gly Leu Leu Gln Asp Glu Ile Pro Phe
                325                 330                 335
Glu Ile Ser Ser Phe Gly Arg Lys Pro Asp Ala Lys Phe Arg Tyr Gly
            340                 345                 350
Phe His Ile Asp Leu Tyr Arg Phe Phe Asn Lys Ala Val Arg Asn
        355                 360                 365
Tyr Ala Phe Glu Gly Lys Tyr Ser Glu Tyr Asn Leu Asp Thr Val Ala
370                 375                 380
Gln Ala Leu Leu Gly Leu Ser Lys Val Lys Leu Asp Glu Ser Ile Ser
385                 390                 395                 400
Asp Leu Asn Met Ser Lys Leu Val Glu Tyr Asn Tyr Arg Asp Ser Glu
                405                 410                 415
Ile Thr Leu Lys Leu Thr Thr Phe Asn Asn Glu Leu Val Trp Lys Leu
            420                 425                 430
Ile Val Leu Phe Ser Arg Ile Ser Lys Leu Gly Ile Glu Glu Leu Thr
        435                 440                 445
Arg Thr Glu Ile Ser Ala Trp Val Lys Asn Leu Tyr Tyr Trp Glu His
    450                 455                 460
Arg Lys Arg Asn Trp Leu Ile Pro Leu Lys Glu Glu Ile Leu Glu Arg
465                 470                 475                 480
Ser Ser Gly Leu Lys Thr Ala Ala Ile Ile Lys Gly Lys Gly Tyr Lys
                485                 490                 495
Gly Ala Val Val Ile Asp Pro Pro Val Gly Val Tyr Phe Asp Val Val
            500                 505                 510
```

-continued

```
Val Leu Asp Phe Ala Ser Leu Tyr Pro Ser Ile Ile Arg Asn Trp Asn
            515                 520                 525

Leu Ser Tyr Glu Thr Val Asp Val Lys Glu Cys Asn Lys Lys Arg Asp
        530                 535                 540

Ile Arg Asp Glu Ser Gly Ala Lys Ile His Glu Val Cys Val Asp Arg
545                 550                 555                 560

Pro Gly Ile Thr Ala Val Val Thr Gly Leu Leu Arg Asp Phe Arg Val
                565                 570                 575

Lys Ile Tyr Lys Lys Gly Lys Gln Ser Asn Ile Asp Glu Glu Arg
            580                 585                 590

Lys Met Leu Tyr Asp Val Val Gln Arg Gly Met Lys Val Phe Ile Asn
        595                 600                 605

Ala Thr Tyr Gly Val Phe Gly Ala Glu Thr Phe Pro Leu Tyr Ala Pro
        610                 615                 620

Ala Val Ala Glu Ser Val Thr Ala Leu Gly Arg Tyr Val Ile Thr Ser
625                 630                 635                 640

Thr Lys Glu Met Ala Asn Lys Leu Gly Leu Lys Val Val Tyr Gly Asp
                645                 650                 655

Thr Asp Ser Leu Phe Ile His Gln Pro Asp Lys Lys Lys Leu Glu Glu
            660                 665                 670

Leu Val Glu Trp Thr Arg Gln Asn Phe Gly Leu Asp Leu Glu Val Asp
        675                 680                 685

Lys Thr Tyr Arg Phe Ile Ala Phe Ser Gly Leu Lys Lys Asn Tyr Phe
        690                 695                 700

Gly Val Phe Lys Asp Ser Lys Val Asp Ile Lys Gly Met Leu Ala Lys
705                 710                 715                 720

Lys Arg Asn Thr Pro Glu Phe Leu Lys Gln Ala Phe Asn Glu Ala Lys
                725                 730                 735

Glu Arg Leu Ala Lys Val Gln Asn Gln Glu Glu Leu Glu Lys Ala Ile
            740                 745                 750

Gln Asp Leu Thr Ala Gln Val Lys Glu Val Tyr Arg Lys Leu Lys Met
        755                 760                 765

Lys Glu Tyr Asn Leu Asp Glu Leu Ala Phe Arg Val Met Leu Ser Arg
        770                 775                 780

Asp Val Lys Ser Tyr Glu Lys Asn Thr Pro Gln His Val Lys Ala Ala
785                 790                 795                 800

Ala Gln Leu Ala Glu Met Asn Val Gln Val Met Ser Arg Asp Ile Ile
                805                 810                 815

Ser Phe Val Lys Val Lys Thr Lys Glu Gly Val Lys Pro Val Gln Leu
            820                 825                 830

Ala Lys Leu Ser Glu Ile Asp Val Asp Lys Tyr Tyr Glu Ser Val Arg
        835                 840                 845

Ser Thr Phe Glu Gln Leu Leu Lys Ser Phe Asn Val Ser Trp Asp Arg
        850                 855                 860

Ile Glu Ser Thr Thr Ser Ile Asp Ser Phe Phe Lys Thr
865                 870                 875
```

<210> SEQ ID NO 9
<211> LENGTH: 2289
<212> TYPE: DNA
<213> ORGANISM: Desulfurococcus sp.
<220> FEATURE:
<221> NAME/KEY: CDS
<222> LOCATION: (1)...(2286)
<220> FEATURE:
<221> NAME/KEY: variation

```
<222> LOCATION: (1801)..(1801)
<223> OTHER INFORMATION: s at position 1801 is either c or g

<400> SEQUENCE: 9 atg gag agg gtt cgc cta gtg aag gtg gtt acc aag gat cct cta atc      48
Met Glu Arg Val Arg Leu Val Lys Val Val Thr Lys Asp Pro Leu Ile
 1               5                  10                  15 gtg agg aag att agg agc aag ttt aac act gcg tgg gag gct aag ata      96
Val Arg Lys Ile Arg Ser Lys Phe Asn Thr Ala Trp Glu Ala Lys Ile
             20                  25                  30 aag tat cat gca aac tac atc tac gat aat agg ctg ata cct gga atg     144
Lys Tyr His Ala Asn Tyr Ile Tyr Asp Asn Arg Leu Ile Pro Gly Met
         35                  40                  45 agg tat gtt aca gac ttc tcc aac ggt gcg caa aag ctt gta atg gtt     192
Arg Tyr Val Thr Asp Phe Ser Asn Gly Ala Gln Lys Leu Val Met Val
     50                  55                  60 aag cca gag ata ccc caa tcc ctt gtt gag aaa gta agg gag ttg ttc     240
Lys Pro Glu Ile Pro Gln Ser Leu Val Glu Lys Val Arg Glu Leu Phe
 65                  70                  75                  80 agg aat gag cct cct gaa aca gtg aag ctg gct gag gaa ctc ctc ctc     288
Arg Asn Glu Pro Pro Glu Thr Val Lys Leu Ala Glu Glu Leu Leu Leu
                 85                  90                  95 ttg ttc gag gag tca ccg ccc aag gtg aag cgc gta gca gtc gac ata     336
Leu Phe Glu Glu Ser Pro Pro Lys Val Lys Arg Val Ala Val Asp Ile
            100                 105                 110 gag gtt ttc acc cca ttc aaa ggg cgt atc ccc agc ccg aag ctc gcc     384
Glu Val Phe Thr Pro Phe Lys Gly Arg Ile Pro Ser Pro Lys Leu Ala
        115                 120                 125 gaa tac cct gtg att agc ata gca ttg gcc ggt agc gac ggc ttg aag     432
Glu Tyr Pro Val Ile Ser Ile Ala Leu Ala Gly Ser Asp Gly Leu Lys
    130                 135                 140 aaa atc ctc ctg ctg gcc agg gaa tac aag cat gat ttc gac tac atg     480
Lys Ile Leu Leu Leu Ala Arg Glu Tyr Lys His Asp Phe Asp Tyr Met
145                 150                 155                 160 atg gag gat tac cct gtt gaa gcc gag gtg gag gtg ttc gac tcc gag     528
Met Glu Asp Tyr Pro Val Glu Ala Glu Val Glu Val Phe Asp Ser Glu
                165                 170                 175 aaa gac atg ttg ctg gaa gcc ttc aga ata atg ggg agc tat ccc gtc     576
Lys Asp Met Leu Leu Glu Ala Phe Arg Ile Met Gly Ser Tyr Pro Val
            180                 185                 190 gtc ctc act tac aac ggt gat aat ttc gac ctt caa tac ctg tac gtg     624
Val Leu Thr Tyr Asn Gly Asp Asn Phe Asp Leu Gln Tyr Leu Tyr Val
        195                 200                 205 aga gcc ttc aag ctg ggg att ctg aga agc cat atc ccg ttg aag ata     672
Arg Ala Phe Lys Leu Gly Ile Leu Arg Ser His Ile Pro Leu Lys Ile
    210                 215                 220 ggg gag gat atg att aga att gac aca agc ata cac cta gat cta tac     720
Gly Glu Asp Met Ile Arg Ile Asp Thr Ser Ile His Leu Asp Leu Tyr
225                 230                 235                 240 aag ttc ttc tcg aac agg gct gtt aaa aac tat gct ttc ggg ggg aaa     768
Lys Phe Phe Ser Asn Arg Ala Val Lys Asn Tyr Ala Phe Gly Gly Lys
                245                 250                 255 tac cag gag gag aag ctt gac gct gtt tca ggg gca ctg cta gga gtg     816
Tyr Gln Glu Glu Lys Leu Asp Ala Val Ser Gly Ala Leu Leu Gly Val
            260                 265                 270 tcg aaa ata ggt ttc gag gaa aca atc ggc ggc ata tcg gcc tca cta     864
Ser Lys Ile Gly Phe Glu Glu Thr Ile Gly Gly Ile Ser Ala Ser Leu
        275                 280                 285 tta gcc gcc tac aac tac agg gat gcc gag atc acg tta aac cta acc     912
Leu Ala Ala Tyr Asn Tyr Arg Asp Ala Glu Ile Thr Leu Asn Leu Thr
```

```
              290                 295                 300
atg ttc agt aat gaa ctc gtt tgg aaa ctc att att ctt cta gct agg      960
Met Phe Ser Asn Glu Leu Val Trp Lys Leu Ile Ile Leu Leu Ala Arg
305                 310                 315                 320 gtt tcc aag aca agc att gaa gac ctg tgt agg agg cag att tcc tac     1008
Val Ser Lys Thr Ser Ile Glu Asp Leu Cys Arg Arg Gln Ile Ser Tyr
                325                 330                 335 tgg att caa aat ctg ttc ttc tgg gag cgc agg aag ctc ggc tac ctc     1056
Trp Ile Gln Asn Leu Phe Phe Trp Glu Arg Arg Lys Leu Gly Tyr Leu
            340                 345                 350 ata cct aac aag gag gac att ctg agg cat gta agg ggg acg ggg acg     1104
Ile Pro Asn Lys Glu Asp Ile Leu Arg His Val Arg Gly Thr Gly Thr
        355                 360                 365 aag gcg att att gag ggt aag aag tac gct gga gcc tta gtg gtt gag     1152
Lys Ala Ile Ile Glu Gly Lys Lys Tyr Ala Gly Ala Leu Val Val Glu
370                 375                 380 cct ccg aaa ggg gct ttc ttc aac gtg gtc gtc ctc gac ata gcc tcc     1200
Pro Pro Lys Gly Ala Phe Phe Asn Val Val Val Leu Asp Ile Ala Ser
385                 390                 395                 400 cta tac cct agc att atc aaa aaa tac aat ctg agc tat gag acc gtt     1248
Leu Tyr Pro Ser Ile Ile Lys Lys Tyr Asn Leu Ser Tyr Glu Thr Val
                405                 410                 415 gac atg aag tgg tgt agc aag aca ata gat att gtc gat gaa acc ggg     1296
Asp Met Lys Trp Cys Ser Lys Thr Ile Asp Ile Val Asp Glu Thr Gly
            420                 425                 430 aga agg ctt cac gaa gtc tgc gtt gac aag ccc ggg ttg acc gcg caa     1344
Arg Arg Leu His Glu Val Cys Val Asp Lys Pro Gly Leu Thr Ala Gln
        435                 440                 445 cta acc ggt att cta agg gat tac agg gtt gga ata tat aag aag agg     1392
Leu Thr Gly Ile Leu Arg Asp Tyr Arg Val Gly Ile Tyr Lys Lys Arg
450                 455                 460 tct aag gat aag agc ctt ccc cct gaa acc ctg gcc tgg tac gag gtg     1440
Ser Lys Asp Lys Ser Leu Pro Pro Glu Thr Leu Ala Trp Tyr Glu Val
465                 470                 475                 480 gtt cag aga gct att aag gtg ttc ata aac gct agc tac ggg gtc ttc     1488
Val Gln Arg Ala Ile Lys Val Phe Ile Asn Ala Ser Tyr Gly Val Phe
                485                 490                 495 ggg gat gag aag ttc tct ctg tac tcc cca gca gtg gct gaa agc gtt     1536
Gly Asp Glu Lys Phe Ser Leu Tyr Ser Pro Ala Val Ala Glu Ser Val
            500                 505                 510 acc gcg atg ggt agg aag tcc ttc tac act att gtg aga aag gcc gcg     1584
Thr Ala Met Gly Arg Lys Ser Phe Tyr Thr Ile Val Arg Lys Ala Ala
        515                 520                 525 gat ctc ggg gtt aaa aca ctg tat ggc gac acg gac tcg ata ttc gtc     1632
Asp Leu Gly Val Lys Thr Leu Tyr Gly Asp Thr Asp Ser Ile Phe Val
530                 535                 540 tgg gcc cca acc cag gag cag ttg agg aag cta cag tca tgg atc ctt     1680
Trp Ala Pro Thr Gln Glu Gln Leu Arg Lys Leu Gln Ser Trp Ile Leu
545                 550                 555                 560 gag aag cta ggc ctg gag atc gag att gac aag tct ttt aca tac gtg     1728
Glu Lys Leu Gly Leu Glu Ile Glu Ile Asp Lys Ser Phe Thr Tyr Val
                565                 570                 575 gtt ttc aca ggg ctt aag aag aac tac ctg ggc aga acg gtt gac ggc     1776
Val Phe Thr Gly Leu Lys Lys Asn Tyr Leu Gly Arg Thr Val Asp Gly
            580                 585                 590 ggc ata gag atc aag ggg ctt gtc scg aag aag agg aat act ccg gag     1824
Gly Ile Glu Ile Lys Gly Leu Val Xaa Lys Lys Arg Asn Thr Pro Glu
        595                 600                 605 ttc ctg aaa gac ttg ttc gag aat gtt atc gaa aag ctt aaa agc gtt     1872
```

```
                                                                        1920
Phe Leu Lys Asp Leu Phe Glu Asn Val Ile Glu Lys Leu Lys Ser Val
    610                 615                 620
gaa aac ccc gcg ggt ttc ata gag ttc gtc aag tgg ttg gag cat cag         1920
Glu Asn Pro Ala Gly Phe Ile Glu Phe Val Lys Trp Leu Glu His Gln
625                 630                 635                 640 gtg aag aca ata cat aac gat att agg agg aag gag ata acg ctc gac         1968
Val Lys Thr Ile His Asn Asp Ile Arg Arg Lys Glu Ile Thr Leu Asp
            645                 650                 655 cgg ctc gcc ata agg gtg gcc tta acc aag acg cca tcc ctc tac act         2016
Arg Leu Ala Ile Arg Val Ala Leu Thr Lys Thr Pro Ser Leu Tyr Thr
        660                 665                 670 aag act aag ccg ccg cat gtt aag gca gcc ctc caa tta atg aac tac         2064
Lys Thr Lys Pro Pro His Val Lys Ala Ala Leu Gln Leu Met Asn Tyr
    675                 680                 685 ggg tac agc gtg gag gag ggg gat att ata acg ttt gtc aag gtg aag         2112
Gly Tyr Ser Val Glu Glu Gly Asp Ile Ile Thr Phe Val Lys Val Lys
690                 695                 700 agc aag gag ggc tat aag gct ata cag tta acg agg ctt cac gaa gta         2160
Ser Lys Glu Gly Tyr Lys Ala Ile Gln Leu Thr Arg Leu His Glu Val
705                 710                 715                 720 gac cct gat aag tac att gag ctt gtt aaa agc ggt ctt gaa caa ttc         2208
Asp Pro Asp Lys Tyr Ile Glu Leu Val Lys Ser Gly Leu Glu Gln Phe
            725                 730                 735 ctc tca gcc ttc gga ata agg tgg gag gat atc ata ggc tcc ggc ggg         2256
Leu Ser Ala Phe Gly Ile Arg Trp Glu Asp Ile Ile Gly Ser Gly Gly
        740                 745                 750 tta acc gag ctt ttg aga aac aat agg gcg tag                             2289
Leu Thr Glu Leu Leu Arg Asn Asn Arg Ala
    755                 760

SEQ ID NO 10
LENGTH: 762
TYPE: PRT
ORGANISM: Desulfurococcus sp.
FEATURE:
NAME/KEY: variation
LOCATION: (601)..(601)
OTHER INFORMATION: Xaa at position 601 is alanine or proline

SEQUENCE: 10

Met Glu Arg Val Arg Leu Val Lys Val Thr Lys Asp Pro Leu Ile
1               5                   10                  15

Val Arg Lys Ile Arg Ser Lys Phe Asn Thr Ala Trp Glu Ala Lys Ile
            20                  25                  30

Lys Tyr His Ala Asn Tyr Ile Tyr Asp Asn Arg Leu Ile Pro Gly Met
        35                  40                  45

Arg Tyr Val Thr Asp Phe Ser Asn Gly Ala Gln Lys Leu Val Met Val
    50                  55                  60

Lys Pro Glu Ile Pro Gln Ser Leu Val Glu Lys Val Arg Glu Leu Phe
65                  70                  75                  80

Arg Asn Glu Pro Pro Glu Thr Val Lys Leu Ala Glu Glu Leu Leu Leu
                85                  90                  95

Leu Phe Glu Glu Ser Pro Pro Lys Val Lys Arg Val Ala Val Asp Ile
            100                 105                 110

Glu Val Phe Thr Pro Phe Lys Gly Arg Ile Pro Ser Pro Lys Leu Ala
        115                 120                 125

Glu Tyr Pro Val Ile Ser Ile Ala Leu Ala Gly Ser Asp Gly Leu Lys
    130                 135                 140

Lys Ile Leu Leu Leu Ala Arg Glu Tyr Lys His Asp Phe Asp Tyr Met
```

```
           145                 150                 155                 160
Met Glu Asp Tyr Pro Val Ala Glu Val Glu Val Phe Asp Ser Glu
                    165                 170                 175
Lys Asp Met Leu Leu Glu Ala Phe Arg Ile Met Gly Ser Tyr Pro Val
                180                 185                 190
Val Leu Thr Tyr Asn Gly Asp Asn Phe Asp Leu Gln Tyr Leu Tyr Val
                195                 200                 205
Arg Ala Phe Lys Leu Gly Ile Leu Arg Ser His Ile Pro Leu Lys Ile
            210                 215                 220
Gly Glu Asp Met Ile Arg Ile Asp Thr Ser Ile His Leu Asp Leu Tyr
225                 230                 235                 240
Lys Phe Phe Ser Asn Arg Ala Val Lys Asn Tyr Ala Phe Gly Gly Lys
                    245                 250                 255
Tyr Gln Glu Glu Lys Leu Asp Ala Val Ser Gly Ala Leu Leu Gly Val
                260                 265                 270
Ser Lys Ile Gly Phe Glu Glu Thr Ile Gly Gly Ile Ser Ala Ser Leu
        275                 280                 285
Leu Ala Ala Tyr Asn Tyr Arg Asp Ala Glu Ile Thr Leu Asn Leu Thr
    290                 295                 300
Met Phe Ser Asn Glu Leu Val Trp Lys Leu Ile Ile Leu Leu Ala Arg
305                 310                 315                 320
Val Ser Lys Thr Ser Ile Glu Asp Leu Cys Arg Arg Gln Ile Ser Tyr
                    325                 330                 335
Trp Ile Gln Asn Leu Phe Phe Trp Glu Arg Arg Lys Leu Gly Tyr Leu
                340                 345                 350
Ile Pro Asn Lys Glu Asp Ile Leu Arg His Val Arg Gly Thr Gly Thr
            355                 360                 365
Lys Ala Ile Ile Glu Gly Lys Lys Tyr Ala Gly Ala Leu Val Val Glu
    370                 375                 380
Pro Pro Lys Gly Ala Phe Phe Asn Val Val Leu Asp Ile Ala Ser
385                 390                 395                 400
Leu Tyr Pro Ser Ile Ile Lys Lys Tyr Asn Leu Ser Tyr Glu Thr Val
                    405                 410                 415
Asp Met Lys Trp Cys Ser Lys Thr Ile Asp Ile Val Asp Glu Thr Gly
                420                 425                 430
Arg Arg Leu His Glu Val Cys Val Asp Lys Pro Gly Leu Thr Ala Gln
            435                 440                 445
Leu Thr Gly Ile Leu Arg Asp Tyr Arg Val Gly Ile Tyr Lys Lys Arg
    450                 455                 460
Ser Lys Asp Lys Ser Leu Pro Pro Glu Thr Leu Ala Trp Tyr Glu Val
465                 470                 475                 480
Val Gln Arg Ala Ile Lys Val Phe Ile Asn Ala Ser Tyr Gly Val Phe
                    485                 490                 495
Gly Asp Glu Lys Phe Ser Leu Tyr Ser Pro Ala Val Ala Glu Ser Val
                500                 505                 510
Thr Ala Met Gly Arg Lys Ser Phe Thr Ile Val Arg Lys Ala Ala
            515                 520                 525
Asp Leu Gly Val Lys Thr Leu Tyr Gly Asp Thr Asp Ser Ile Phe Val
    530                 535                 540
Trp Ala Pro Thr Gln Glu Gln Leu Arg Lys Leu Gln Ser Trp Ile Leu
545                 550                 555                 560
Glu Lys Leu Gly Leu Glu Ile Glu Ile Asp Lys Ser Phe Thr Tyr Val
                    565                 570                 575
```

```
Val Phe Thr Gly Leu Lys Lys Asn Tyr Leu Gly Arg Thr Val Asp Gly
            580                 585                 590

Gly Ile Glu Ile Lys Gly Leu Val Xaa Lys Lys Arg Asn Thr Pro Glu
        595                 600                 605

Phe Leu Lys Asp Leu Phe Glu Asn Val Ile Glu Lys Leu Lys Ser Val
            610                 615                 620

Glu Asn Pro Ala Gly Phe Ile Glu Phe Val Lys Trp Leu Glu His Gln
625                 630                 635                 640

Val Lys Thr Ile His Asn Asp Ile Arg Arg Lys Glu Ile Thr Leu Asp
                645                 650                 655

Arg Leu Ala Ile Arg Val Ala Leu Thr Lys Thr Pro Ser Leu Tyr Thr
            660                 665                 670

Lys Thr Lys Pro Pro His Val Lys Ala Ala Leu Gln Leu Met Asn Tyr
            675                 680                 685

Gly Tyr Ser Val Glu Gly Asp Ile Ile Thr Phe Val Lys Val Lys
            690                 695                 700

Ser Lys Glu Gly Tyr Lys Ala Ile Gln Leu Thr Arg Leu His Glu Val
705                 710                 715                 720

Asp Pro Asp Lys Tyr Ile Glu Leu Val Lys Ser Gly Leu Glu Gln Phe
                725                 730                 735

Leu Ser Ala Phe Gly Ile Arg Trp Glu Asp Ile Ile Gly Ser Gly Gly
            740                 745                 750

Leu Thr Glu Leu Leu Arg Asn Asn Arg Ala
            755                 760

<210> SEQ ID NO 11
<211> LENGTH: 1725
<212> TYPE: DNA
<213> ORGANISM: Aquifex pyrophilus
<220> FEATURE:
<221> NAME/KEY: CDS
<222> LOCATION: (1)...(1722)

<400> SEQUENCE: 11 atg gat ttt gaa tac gta acg gga gaa gag gga tta aaa aag gca ata      48
Met Asp Phe Glu Tyr Val Thr Gly Glu Glu Gly Leu Lys Lys Ala Ile
1               5                   10                  15 aaa agg ctc gaa aat tct cca tac ctt tac ctg gat acg gaa acc aca      96
Lys Arg Leu Glu Asn Ser Pro Tyr Leu Tyr Leu Asp Thr Glu Thr Thr
            20                  25                  30 gga gac agg ata agg ctc gta caa atc gga gac gaa gaa aac acc tac     144
Gly Asp Arg Ile Arg Leu Val Gln Ile Gly Asp Glu Glu Asn Thr Tyr
        35                  40                  45 gtt att gac ctc tac gaa att cag gat ata gaa cct ctg agg aaa tta     192
Val Ile Asp Leu Tyr Glu Ile Gln Asp Ile Glu Pro Leu Arg Lys Leu
    50                  55                  60 ata aac gaa agg ggg ata gta ggg cac aac ctt aag ttc gat ctt aag     240
Ile Asn Glu Arg Gly Ile Val Gly His Asn Leu Lys Phe Asp Leu Lys
65                  70                  75                  80 tac ctc tac agg tac ggg ata ttt ccc tcg gca acg ttt gac act atg     288
Tyr Leu Tyr Arg Tyr Gly Ile Phe Pro Ser Ala Thr Phe Asp Thr Met
                85                  90                  95 ata gcg agc tac ctc ctc gga tac gag aga cac tcc ctc aat cac ata     336
Ile Ala Ser Tyr Leu Leu Gly Tyr Glu Arg His Ser Leu Asn His Ile
            100                 105                 110 gtt tca aac cta ctc gga tat tcc atg gac aag agt tat cag act tcc     384
Val Ser Asn Leu Leu Gly Tyr Ser Met Asp Lys Ser Tyr Gln Thr Ser
        115                 120                 125
```

```
gac tgg gga gcg agc gtt ctg agc gac gct cag ctc aag tac gct gca      432
Asp Trp Gly Ala Ser Val Leu Ser Asp Ala Gln Leu Lys Tyr Ala Ala
    130                 135                 140 aac gac gtt ata gtc ctc aga gaa ctc ttc cct aag atg agg gac atg      480
Asn Asp Val Ile Val Leu Arg Glu Leu Phe Pro Lys Met Arg Asp Met
145                 150                 155                 160 tta aac gag cta gac gct gag agg gga gag gaa ctg ctc aag act aga      528
Leu Asn Glu Leu Asp Ala Glu Arg Gly Glu Glu Leu Leu Lys Thr Arg
            165                 170                 175 acg gca aag att ttc gat ctg aag agt ccc gta gca ata gtg gaa atg      576
Thr Ala Lys Ile Phe Asp Leu Lys Ser Pro Val Ala Ile Val Glu Met
        180                 185                 190 gct ttc gta agg gaa gtt gca aaa ctc gag ata aac ggc ttt ccc gtg      624
Ala Phe Val Arg Glu Val Ala Lys Leu Glu Ile Asn Gly Phe Pro Val
    195                 200                 205 gac gta gaa gag cta acc aac aag tta aaa gct gtg gaa agg gaa acc      672
Asp Val Glu Glu Leu Thr Asn Lys Leu Lys Ala Val Glu Arg Glu Thr
210                 215                 220 cag aag agg ata cag gag ttt tac ata aag tac aga gtt gac cct ctc      720
Gln Lys Arg Ile Gln Glu Phe Tyr Ile Lys Tyr Arg Val Asp Pro Leu
225                 230                 235                 240 tct ccg aaa cag ctc gcc tca ctc ctg acg aag aag ttt aaa ctg aac      768
Ser Pro Lys Gln Leu Ala Ser Leu Leu Thr Lys Lys Phe Lys Leu Asn
            245                 250                 255 ctt ccc aag act cct aaa ggg aac gta tct aca gac gac aag gct ctt      816
Leu Pro Lys Thr Pro Lys Gly Asn Val Ser Thr Asp Asp Lys Ala Leu
        260                 265                 270 act tcc tat cag gac gta gaa ccc gta aaa ctc gtt ctg gaa ata aga      864
Thr Ser Tyr Gln Asp Val Glu Pro Val Lys Leu Val Leu Glu Ile Arg
    275                 280                 285 aag ctt aag aag atc gcg gac aag tta aag gag tta aaa gaa cac ttg      912
Lys Leu Lys Lys Ile Ala Asp Lys Leu Lys Glu Leu Lys Glu His Leu
290                 295                 300 aag aac ggg aga gtt tac ccg gag ttc aag caa ata gga gct gta acg      960
Lys Asn Gly Arg Val Tyr Pro Glu Phe Lys Gln Ile Gly Ala Val Thr
305                 310                 315                 320 gga agg atg tcc tcc gca cac cca aat atc cag aac ata cac agg gat     1008
Gly Arg Met Ser Ser Ala His Pro Asn Ile Gln Asn Ile His Arg Asp
            325                 330                 335 atg aga gga att ttc aag gcg gag gag gga aat act ttc gtc att tcg     1056
Met Arg Gly Ile Phe Lys Ala Glu Glu Gly Asn Thr Phe Val Ile Ser
        340                 345                 350 gac ttt tct cag ata gag ctc agg att gcg gcc gaa tac gta aag gac     1104
Asp Phe Ser Gln Ile Glu Leu Arg Ile Ala Ala Glu Tyr Val Lys Asp
    355                 360                 365 ccg ctt atg ctg gac gcc ttc aaa aag gga aag gac atg cac agg tac     1152
Pro Leu Met Leu Asp Ala Phe Lys Lys Gly Lys Asp Met His Arg Tyr
370                 375                 380 acc gct tca gtg gta ctc gga aag aaa gag gaa gaa ata aca aaa gag     1200
Thr Ala Ser Val Val Leu Gly Lys Lys Glu Glu Glu Ile Thr Lys Glu
385                 390                 395                 400 gag aga cag ctc gca aaa gct ata aac ttc ggt ctc ata tac ggc att     1248
Glu Arg Gln Leu Ala Lys Ala Ile Asn Phe Gly Leu Ile Tyr Gly Ile
            405                 410                 415 tcc gct aaa ggg ctt gca gaa tac gca aag ctt ggt tac ggc gtt gaa     1296
Ser Ala Lys Gly Leu Ala Glu Tyr Ala Lys Leu Gly Tyr Gly Val Glu
        420                 425                 430 att tct tta gaa gaa gct cag gtt ttg aga gag agg ttt ttc aag aac     1344
Ile Ser Leu Glu Glu Ala Gln Val Leu Arg Glu Arg Phe Phe Lys Asn
```

```
                     435                 440                  445
ttc aaa gct ttc aaa gag tgg cac gac aga gtt aag aaa gaa cta aag       1392
Phe Lys Ala Phe Lys Glu Trp His Asp Arg Val Lys Lys Glu Leu Lys
        450                 455                 460 gaa aag gga gag gta aaa ggt cat acg ctt ctt gga agg aga ttt tcc       1440
Glu Lys Gly Glu Val Lys Gly His Thr Leu Leu Gly Arg Arg Phe Ser
465                 470                 475                 480 gca aat acc ttt aac gac gct gta aat tac ccc ata cag gga acg ggt       1488
Ala Asn Thr Phe Asn Asp Ala Val Asn Tyr Pro Ile Gln Gly Thr Gly
                485                 490                 495 gcg gac cta cta aaa ctg gca gtt cta ctt ttt gac gca aac ctc cag       1536
Ala Asp Leu Leu Lys Leu Ala Val Leu Leu Phe Asp Ala Asn Leu Gln
            500                 505                 510 aaa aag gga ata gat gca aag ctc gtg aac ctc gtg cac gac gag ata       1584
Lys Lys Gly Ile Asp Ala Lys Leu Val Asn Leu Val His Asp Glu Ile
        515                 520                 525 gtc gta gag tgc gaa aag gaa aaa gcg gaa gaa gta aaa gaa ata ctc       1632
Val Val Glu Cys Glu Lys Glu Lys Ala Glu Glu Val Lys Glu Ile Leu
    530                 535                 540 gaa aaa tcc atg aaa acg gcg gga aag ata ata ctg aaa gag gtt ccc       1680
Glu Lys Ser Met Lys Thr Ala Gly Lys Ile Ile Leu Lys Glu Val Pro
545                 550                 555                 560 gtg gaa gta gaa agc gtt ata aac gaa agg tgg acg aaa gat               1722
Val Glu Val Glu Ser Val Ile Asn Glu Arg Trp Thr Lys Asp
                565                 570 taa                                                                   1725

<210> SEQ ID NO 12
<211> LENGTH: 574
<212> TYPE: PRT
<213> ORGANISM: Aquifex pyrophilus

<400> SEQUENCE: 12

Met Asp Phe Glu Tyr Val Thr Gly Glu Glu Gly Leu Lys Lys Ala Ile
1               5                   10                  15

Lys Arg Leu Glu Asn Ser Pro Tyr Leu Tyr Leu Asp Thr Glu Thr Thr
            20                  25                  30

Gly Asp Arg Ile Arg Leu Val Gln Ile Gly Asp Glu Glu Asn Thr Tyr
        35                  40                  45

Val Ile Asp Leu Tyr Glu Ile Gln Asp Ile Glu Pro Leu Arg Lys Leu
    50                  55                  60

Ile Asn Glu Arg Gly Ile Val Gly His Asn Leu Lys Phe Asp Leu Lys
65                  70                  75                  80

Tyr Leu Tyr Arg Tyr Gly Ile Phe Pro Ser Ala Thr Phe Asp Thr Met
                85                  90                  95

Ile Ala Ser Tyr Leu Leu Gly Tyr Glu Arg His Ser Leu Asn His Ile
            100                 105                 110

Val Ser Asn Leu Leu Gly Tyr Ser Met Asp Lys Ser Tyr Gln Thr Ser
        115                 120                 125

Asp Trp Gly Ala Ser Val Leu Ser Asp Ala Gln Leu Lys Tyr Ala Ala
    130                 135                 140

Asn Asp Val Ile Val Leu Arg Glu Leu Phe Pro Lys Met Arg Asp Met
145                 150                 155                 160

Leu Asn Glu Leu Asp Ala Glu Arg Gly Glu Glu Leu Leu Lys Thr Arg
                165                 170                 175

Thr Ala Lys Ile Phe Asp Leu Lys Ser Pro Val Ala Ile Val Glu Met
            180                 185                 190
```

```
Ala Phe Val Arg Glu Val Ala Lys Leu Glu Ile Asn Gly Phe Pro Val
            195                 200                 205

Asp Val Glu Glu Leu Thr Asn Lys Leu Lys Ala Val Glu Arg Glu Thr
            210                 215                 220

Gln Lys Arg Ile Gln Glu Phe Tyr Ile Lys Tyr Arg Val Asp Pro Leu
225                 230                 235                 240

Ser Pro Lys Gln Leu Ala Ser Leu Leu Thr Lys Lys Phe Lys Leu Asn
                245                 250                 255

Leu Pro Lys Thr Pro Lys Gly Asn Val Ser Thr Asp Lys Ala Leu
                260                 265             270

Thr Ser Tyr Gln Asp Val Glu Pro Val Lys Leu Val Leu Glu Ile Arg
            275                 280                 285

Lys Leu Lys Lys Ile Ala Asp Lys Leu Lys Glu Leu Lys Glu His Leu
            290                 295                 300

Lys Asn Gly Arg Val Tyr Pro Glu Phe Lys Gln Ile Gly Ala Val Thr
305                 310                 315                 320

Gly Arg Met Ser Ser Ala His Pro Asn Ile Gln Asn Ile His Arg Asp
                325                 330                 335

Met Arg Gly Ile Phe Lys Ala Glu Glu Gly Asn Thr Phe Val Ile Ser
                340                 345                 350

Asp Phe Ser Gln Ile Glu Leu Arg Ile Ala Ala Glu Tyr Val Lys Asp
            355                 360                 365

Pro Leu Met Leu Asp Ala Phe Lys Lys Gly Lys Asp Met His Arg Tyr
            370                 375                 380

Thr Ala Ser Val Val Leu Gly Lys Lys Glu Glu Glu Ile Thr Lys Glu
385                 390                 395                 400

Glu Arg Gln Leu Ala Lys Ala Ile Asn Phe Gly Leu Ile Tyr Gly Ile
                405                 410                 415

Ser Ala Lys Gly Leu Ala Glu Tyr Ala Lys Leu Gly Tyr Gly Val Glu
                420                 425                 430

Ile Ser Leu Glu Glu Ala Gln Val Leu Arg Glu Arg Phe Phe Lys Asn
            435                 440                 445

Phe Lys Ala Phe Lys Glu Trp His Asp Arg Val Lys Lys Glu Leu Lys
            450                 455                 460

Glu Lys Gly Glu Val Lys Gly His Thr Leu Leu Gly Arg Arg Phe Ser
465                 470                 475                 480

Ala Asn Thr Phe Asn Asp Ala Val Asn Tyr Pro Ile Gln Gly Thr Gly
                485                 490                 495

Ala Asp Leu Leu Lys Leu Ala Val Leu Leu Phe Asp Ala Asn Leu Gln
                500                 505                 510

Lys Lys Gly Ile Asp Ala Lys Leu Val Asn Leu Val His Asp Glu Ile
            515                 520                 525

Val Val Glu Cys Glu Lys Glu Lys Ala Glu Glu Val Lys Glu Ile Leu
            530                 535                 540

Glu Lys Ser Met Lys Thr Ala Gly Lys Ile Ile Leu Lys Glu Val Pro
545                 550                 555                 560

Val Glu Val Glu Ser Val Ile Asn Glu Arg Trp Thr Lys Asp
                565                 570
```

ISOLATION AND IDENTIFICATION OF NOVEL POLYMERASES

This application is a divisional of application Ser. No. 09/907,166, filed Aug. 6, 1997, now U.S. Pat. No. 5,948, 666.

FIELD OF THE INVENTION

This invention relates to newly identified polynucleotides, polypeptides encoded by such polynucleotides, the use of such polynucleotides and polypeptides, as well as the production and isolation of such polynucleotides and polypeptides. More particularly, the polypeptides of the present invention have been identified as polymerases.

BACKGROUND OF THE INVENTION

Thermophilic bacteria have received considerable attention as sources of highly active and thermostable enzymes. Recently, the most extremely thermophilic organotrophic eubacteria presently known have been isolated and characterized. These bacteria, which belong to the genus thermotoga, are fermentative microorganisms metabolizing a variety of carbohydrates (Huber, R. and Stetter, K. O., in Ballows, et al., (Ed.), The Procaryotes, 2nd Ed., Springer-Verlaz, New York, pgs. 3809–3819 (1992)).

In Huber et al., 1986, Arch. Microbiol. 144:324–333, the isolation of the bacterium *Thermotoga maritima* is described. *T. maritima* is a eubacterium that is strictly anaerobic, rod-shaped, fermentative, hyperthermophilic, and grows between 55° C. and 90° C., with an optimum growth temperature of about 80° C. This eubacterium has been isolated from geothermally heated sea floors in Italy and the Azores. *T. maritima* cells have a sheath-like structure and monotrichous flagellation. *T. maritima* is classified in the eubacterium kingdom by virtue of having murein and fatty acid-containing lipids, diphtheria-toxin-resistant elongation factor 2, an RNA polymerase subunit pattern, and sensitivity to antibiotics.

Since, to date, most organisms identified from the archaeal domain are thermophiles or hyperthermophiles, archaea are also considered a fertile source of thermophilic enzymes.

SUMMARY OF THE INVENTION

The present invention provides polynucleotides and polypeptides encoded thereby which have been identified as polymerase enzymes. In accordance with one aspect of the present invention, there is provided novel enzymes, as well as active fragments, analogs and derivatives thereof.

In accordance with another aspect of the present invention, there are provided isolated nucleic acid molecules encoding enzymes of the present invention including mRNAs, DNAs, cDNAs, genomic DNAs as well as active analogs and fragments of such enzymes.

In accordance with another aspect of the present invention there are provided isolated nucleic acid molecules encoding mature polypeptides expressed by the DNA in SEQ ID Nos: 1, 3, 5, 7, 9, 11.

In accordance with yet a further aspect of the present invention, there is provided a process for producing such polypeptide by recombinant techniques comprising culturing recombinant prokaryotic and/or eukaryotic host cells, containing a nucleic acid sequence encoding an enzyme of the present invention, under conditions promoting expression of said enzyme and subsequent recovery of said enzyme.

In accordance with yet a further aspect of the present invention, there is provided a process for utilizing such enzymes, or polynucleotide encoding such enzymes for polymerizing DNA.

In accordance with yet a further aspect of the present invention, there is also provided nucleic acid probes comprising nucleic acid molecules of sufficient length to specifically hybridize to a nucleic acid sequence of the present invention.

In accordance with yet a further aspect of the present invention, there is provided a process for utilizing such enzymes, or polynucleotides encoding such enzymes, for in vitro purposes related to scientific research, for example, to generate probes for identifying similar sequences which might encode similar enzymes from other organisms.

These and other aspects of the present invention should be apparent to those skilled in the art from the teachings herein.

BRIEF DESCRIPTION OF THE DRAWINGS

The following drawings are illustrative of embodiments of the invention and are not meant to limit the scope of the invention as encompassed by the claims. Sequencing was performed using a 378 automated DNA sequencer (Applied Biosystems, Inc.).

FIGS. 1A–H shows the nucleotide and deduced amino acid sequence of DNA polymerase (3py1) from *Ammonifex degensii*.

FIGS. 2A–G shows the nucleotide and deduced amino acid sequence of DNA polymerase (1PY2) from *Pyrolobus furmarius*.

FIGS. 3A–G shows the nucleotide and deduced amino acid sequence of DNA polymerase (5PY1) from *Archaeoglobus lithotrophicus*.

FIGS. 4A–H shows the nucleotide and deduced amino acid sequence of DNA polymerase (23PY1) from *Metallosphaera prunae*.

FIGS. 5A–G shows the nucleotide and deduced amino acid sequence of DNA polymerase (29PY1) from *Desulfurococcus*.

FIGS. 6A–E shows the nucleotide and deduced amino acid sequence of DNA polymerase (34PY1) from *Aquifex* VF-5.

DESCRIPTION OF THE PREFERRED EMBODIMENTS

The term "gene" means the segment of DNA involved in producing a polypeptide chain; it includes regions preceding and following the coding region (leader and trailer) as well as intervening sequences (introns) between individual coding segments (exons).

A coding sequence is "operably linked to" another coding sequence when RNA polymerase will transcribe the two coding sequences into a single mRNA, which is then translated into a single polypeptide having amino acids derived from both coding sequences. The coding sequences need not be contiguous to one another so long as the expressed sequences are ultimately processed to produce the desired protein.

"Recombinant" enzymes refer to enzymes produced by recombinant DNA techniques; i.e., produced from cells transformed by an exogenous DNA construct encoding the desired enzyme. "Synthetic" enzymes are those prepared by chemical synthesis.

A DNA "coding sequence of" or a "nucleotide sequence encoding" a particular enzyme, is a DNA sequence which is transcribed and translated into an enzyme when placed under the control of appropriate regulatory sequences. A "promotor sequence" is a DNA regulatory region capable of binding RNA polymerase in a cell and initiating transcription of a downstream (3' direction) coding sequence. The promoter is part of the DNA sequence. This sequence region has a start codon at its 3' terminus. The promoter sequence does include the minimum number of bases where elements necessary to initiate transcription at levels detectable above background. However, after the RNA polymerase binds the sequence and transcription is initiated at the start codon (3' terminus with a promoter), transcription proceeds downstream in the 3' direction. Within the promotor sequence will be found a transcription initiation site (conveniently defined by mapping with nuclease S1) as well as protein binding domains (consensus sequences) responsible for the binding of RNA polymerase.

Figure 1E:
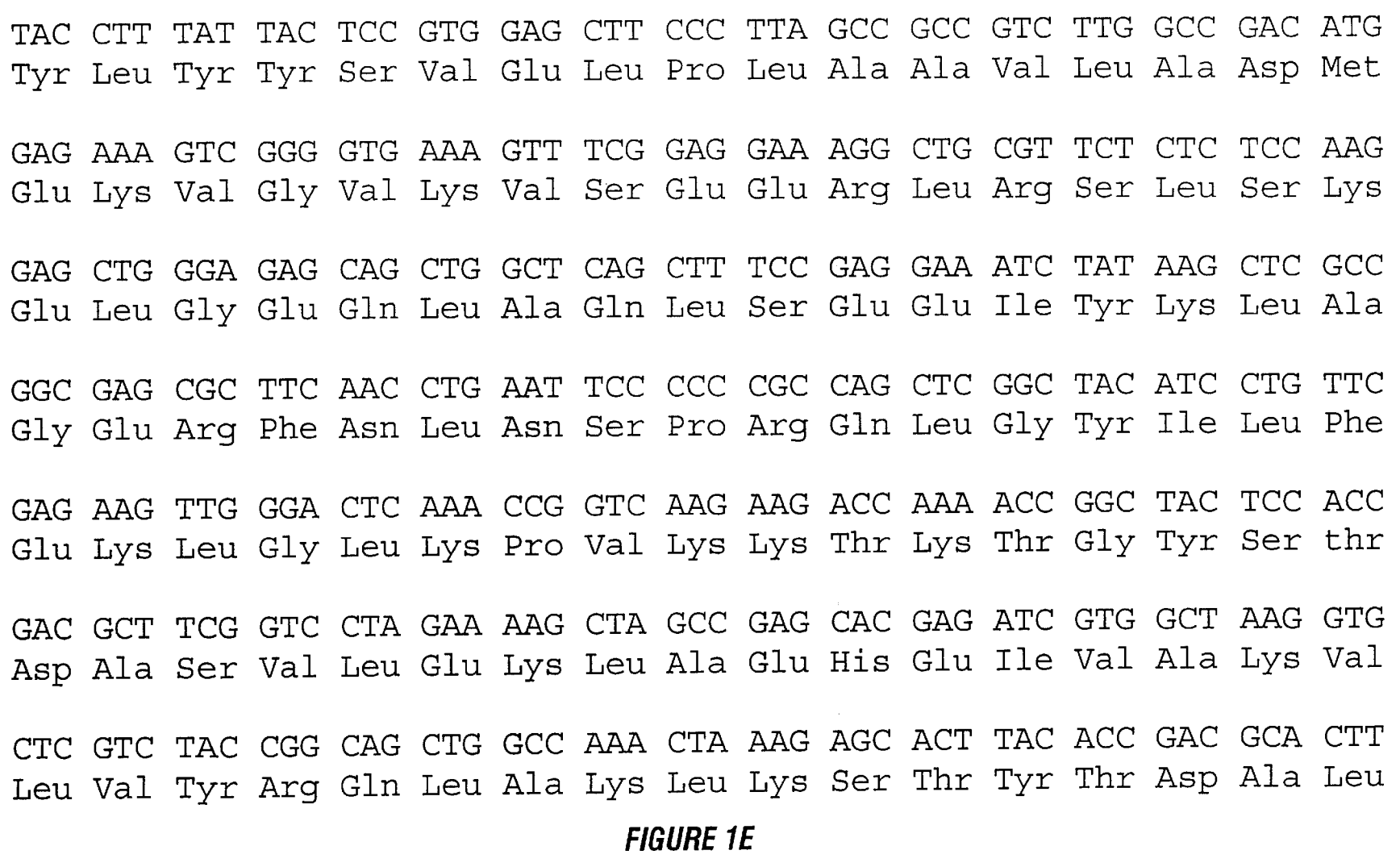

The present invention provides purified thermostable enzymes that catalyze DNA synthesis by addition of deoxynucleotides to the 3' end of a polynucleotide chain, using a complementary polynucleotide strand as a template. An exemplary purified enzyme is a polymerase derived from an organism referred herein as "Ammonifex degensii KC4" is a gram negative, chemolithoautotrophic eubacteria and has a very high temperature optimum. Ammonifex degensii KC4 was discovered in a deep sea isolate from the Middle Atlantic Ridge. Ammonifex degensii KC4 grows optimally at 70° C. and pH 7.0 in a low salt medium. This exemplary enzyme is shown in FIG. 1.

The polynucleotide encoding SEQ ID NO:1 was originally recovered from a genomic gene library derived from Ammonifex degensii KC4 as described below. It contains an open reading frame encoding a protein of 867 amino acid residues.

In one embodiment, the representative polymerase of SEQ ID NO:1 of the present invention has a molecular weight of about 95.6 kilodaltons as measured by SDS-PAGE gel electrophoresis and an inferred molecular weight from the nucleotide sequence of the gene. This purified enzyme may be used to polymerize DNA where desired. The polymerase enzyme of the present invention has a very high thermostability and has the closest homology to polymerase from Bacillus stearothermophilus with 56% identity and 75% similarity at the amino acid level.

In accordance with an aspect of the present invention, there are provided isolated nucleic acid molecules (polynucleotides) which encode for the mature enzymes having the deduced amino acid sequence of FIGS. 1–6 and SEQ ID NOs:1, 3, 5, 7, 9, 11.

This invention, in addition to the isolated nucleic acid molecule encoding an polymerase enzyme disclosed in FIGS. 1–6 (SEQ ID NOs:1, 3, 5, 7, 9, 11), also provides substantially similar sequences. Isolated nucleic acid sequences are substantially similar if: (i) they are capable of hybridizing under stringent conditions, hereinafter described, to SEQ ID NO:1; or (ii) they encode DNA sequences which are degenerate to SEQ ID NO:1. Degenerate DNA sequences encode the amino acid sequence of SEQ ID NO:2, but have variations in the nucleotide coding sequences. As used herein, "substantially similar" refers to the sequences having similar identity to the sequences of the instant invention. The nucleotide sequences that are substantially similar can be identified by hybridization or by sequence comparison. Enzyme sequences that are substantially similar can be identified by one or more of the following: proteolytic digestion, gel electrophoresis and/or microsequencing. One means for isolating a nucleic acid molecule encoding a polymerase enzyme is to probe a genomic gene library with a natural or artificially designed probe using art recognized procedures (see, for example: Current Protocols in Molecular Biology, Ausubel F. M. et al. (EDS.) Green Publishing Company Assoc. and John Wiley Interscience, New York, 1989, 1992). It is appreciated to one skilled in the art that SEQ ID NO:1, or fragments thereof (comprising at least 15 contiguous nucleotides), is a particularly useful probe. Other particular useful probes for this purpose are hybridizable fragments to the sequences of SEQ ID NO:1 (i.e., comprising at least 15 contiguous nucleotides).

With respect to nucleic acid sequences which hybridize to specific nucleic acid sequences disclosed herein, hybridization may be carried out under conditions of reduced stringency, medium stringency or even stringent conditions. As an example of oligonucleotide hybridization, a polymer membrane containing immobilized denatured nucleic acid is first prehybridized for 30 minutes at 45° C. in a solution consisting of 0.9 M NaCl, 50 mM $NaH_2PO_4$, pH 7.0, 5.0 mM $Na_2EDTA$, 0.5% SDS, 10×Denhardt's, and 0.5 mg/mL polyriboadenylic acid. Approximately $2 \times 10^7$ cpm (specific activity $4-9 \times 10^6$ cpm/$\mu$g) of $^{32}P$ end-labeled oligonucleotide probe are then added to the solution. After 12–16 hours of incubation, the membrane is washed for 30 minutes at room temperature in 1× SET (150 mM NaCl, 20 mM Tris hydrochloride, pH 7.8, 1 mM $Na_2EDTA$) containing 0.5% SDS, followed by a 30 minute wash in fresh 1× SET at Tm-10° C. for the oligo-nucleotide probe. The membrane is then exposed to auto-radiographic film for detection of hybridization signals.

In nucleic acid hybridization reactions, the conditions used to achieve a particular level of stringency will vary, depending on the nature of the nucleic acids being hybridized. For example, the length, degree of complementarity, nucleotide sequence composition (e.g., GC v. AT content), and nucleic acid type (e.g., RINA v. DNA) of the hybridizing regions of the nucleic acids can be considered in selecting hybridization conditions. An additional consideration is whether one of the nucleic acids is immobilized, for example, on a filter.

An example of progressively higher stringency conditions is as follows: 2×SSC/0.1% SDS at about room temperature (hybridization conditions); 0.2×SSC/0.1% SDS at about room temperature (low stringency conditions); 0.2×SSC/ 0.1% SDS at about 42° C. (moderate stringency conditions); and 0.1×SSC at about 68° C. (high stringency conditions). Washing can be carried out using only one of these conditions, e.g., high stringency conditions, or each of the conditions can be used, e.g., for 10–15 minutes each, in the order listed above, repeating any or all of the steps listed. However, as mentioned above, optimal conditions will vary, depending on the particular hybridization reaction involved, and can be determined empirically.

"Identity" as the term is used herein, refers to a polynucleotide sequence which comprises a percentage of the same bases as a reference polynucleotide (SEQ ID NO:1). For example, a polynucleotide which is at least 90% identical to a reference polynucleotide, has polynucleotide bases which are identical in 90% of the bases which make up the reference polynucleotide and may have different bases in 10% of the bases which comprise that polynucleotide sequence.

The present invention also relates to polynucleotides which differ from the reference polynucleotide such that the changes are silent changes, for example the changes do not alter the amino acid sequence encoded by the polynucleotide. The present invention also relates to nucleotide changes which result in amino acid substitutions, additions, deletions, fusions and truncations in the enzyme encoded by the reference polynucleotide (SEQ ID NO:1). In a preferred aspect of the invention these enzymes retain the same biological action as the enzyme encoded by the reference polynucleotide.

It is also appreciated that such probes can be and are preferably labeled with an analytically detectable reagent to facilitate identification of the probe. Useful reagents include but are not limited to radioactivity, fluorescent dyes or enzymes capable of catalyzing the formation of a detectable product. The probes are thus useful to isolate complementary copies of DNA from other animal sources or to screen such sources for related sequences.

The present invention provides substantially pure polymerase enzymes. The term "substantially pure" is used herein to describe a molecule, such as a polypeptide (e.g., a polymerase polypeptide, or a fragment thereof) that is substantially free of other proteins, lipids, carbohydrates, nucleic acids, and other biological materials with which it is naturally associated. For example, a substantially pure molecule, such as a polypeptide, can be at least 60%, by dry weight, the molecule of interest. The purity of the polypeptides can be determined using standard methods including, e.g., polyacrylamide gel electrophoresis (e.g., SDS-PAGE), column chromatography (e.g., high performance liquid chromatography (HPLC)), and amino-terminal amino acid sequence analysis.

Polymerase polypeptides included in the invention can have one of the amino acid sequences of polymerases shown in FIGS. 1 through 6 (SEQ ID Nos:2, 4, 6, 8, 10, 12), for example, the amino acid sequence of *Ammonifex degensii* KC4 (SEQ ID NO:2). Polymerase polypeptides, such as those isolated from *Ammonifex degensii* KC4, can be characterized by polymerizing DNA.

Also included in the invention are polypeptides having sequences that are "substantially identical" to the sequence of a polymerase polypeptide, such as one of SEQ ID NO:2, e.g., SEQ ID NO:4. A "substantially identical" amino acid sequence is a sequence that differs from a reference sequence only by conservative amino acid. substitutions, for example, substitutions of one amino acid for another of the same class (e.g., substitution of one hydrophobic amino acid, such as isoleucine, valine, leucine, or methionine, for another, or substitution of one polar amino acid for another, such as substitution of arginine for lysine, glutamic acid for aspartic acid, or glutamine for asparagine), or by one or more non-conservative substitutions, deletions, or insertions, provided that the polypeptide retains at least one polymerase-specific activity or a polymerase-specific epitope. For example, one or more amino acids can be deleted from a polymerase polypeptide, resulting in modification of the structure of the polypeptide, without significantly altering its biological activity. For example, amino- or carboxyl-terminal amino acids that are not required for polymerase biological activity, can be removed. Such modifications can result in the development of smaller active polymerase polypeptides.

Other polymerase polypeptides included in the invention are polypeptides having amino acid sequences that are at least 50% identical to the amino acid sequence of a polymerase polypeptide, such as any of polymerases in SEQ ID Nos:2, 4, 6, 8, 10, 12, e.g., SEQ ID NO:12. The length of comparison in determining amino acid sequence homology can be, for example, at least 15 amino acids, for example, at least 20, 25, or 35 amino acids. Homology can be measured using standard sequence analysis software (e.g., Sequence Analysis Software Package of the Genetics Computer Group, University of Wisconsin Biotechnology Center, 1710 University Avenue, Madison, Wis. 53705; also see Ausubel, et al., supra).

The invention also includes fragments of polymerase polypeptides that retain at least one polymerase-specific activity or epitope. Polymerase activity can be assayed by examining the polymerizing of DNA. For example, a polymerase polypeptide fragment containing, e.g., at least 8–10 amino acids can be used as an immunogen in the production of polymerase-specific antibodies. The fragment can contain, for example, an amino acid sequence that is conserved in polymerases, and this amino acid sequence can contain amino acids that are conserved in polymerases. Such fragments can easily be identified by comparing the sequences of polymerases found in FIGS. 1–X. In addition to their use as peptide immunogens, the above-described polymerase fragments can be used in immunoassays, such as ELISAs, to detect the presence of polymerase-specific antibodies in samples.

The polymerase polypeptides of the invention can be obtained using any of several standard methods. For example, polymerase polypeptides can be produced in a standard recombinant expression systems (see below), chemically synthesized (this approach may be limited to small polymerase peptide fragments), or purified from organisms in which they are naturally expressed.

The invention also provides isolated nucleic acid molecules that encode the polymerase polypeptides described above, as well as fragments thereof. For example, nucleic acids that encode any of SEQ ID Nos:1, 3, 5, 7, 9, 11 are included in the invention. These nucleic acids can contain naturally occurring nucleotide sequences, or sequences that differ from those of the naturally occurring nucleic acids that encode polymerases, but encode the same amino acids, due to the degeneracy of the genetic code. The nucleic acids of the invention can contain DNA or RNA nucleotides, or combinations or modifications thereof. Exemplary nucleic acids of the invention are shown in SEQ ID NO:1.

By "isolated nucleic acid" is meant a nucleic acid, e.g., a DNA or RNA molecule, that is not immediately contiguous with the 5' and 3' flanking sequences with which it normally is immediately contiguous when present in the naturally occurring genome of the organism from which it is derived. The term thus describes, for example, a nucleic acid that is incorporated into a vector, such as a plasmid or viral vector; a nucleic acid that is incorporated into the genome of a heterologous cell (or the genome of a homologous cell, but at a site different from that at which it naturally occurs); and a nucleic acid that exists as a separate molecule, e.g., a DNA fragment produced by PCR amplification or restriction enzyme digestion, or an RNA molecule produced by in vitro transcription. The term also describes a recombinant nucleic acid that forms part of a hybrid gene encoding additional polypeptide sequences that can be used, for example, in the production of a fusion protein.

The nucleic acid molecules of the invention can be used as templates in standard methods for production of polymerase gene products (e.g., polymerase RNAs and polymerase polypeptides). In addition, the nucleic acid molecules that encode polymerase polypeptides (and fragments thereof) and related nucleic acids, such as (1) nucleic acids containing sequences that are complementary to, or that hybridize to, nucleic acids encoding polymerase polypeptides, or fragments thereof (e.g., fragments containing at least 12, 15, 20, or 25 nucleotides); and (2) nucleic acids containing sequences that hybridize to sequences that are complementary to nucleic acids encoding polymerase polypeptides, or fragments thereof (e.g., fragments containing at least 12, 15, 20, or 25 nucleotides); can be used in methods focused on their hybridization properties. For example, as is described in further detail below, such nucleic acid molecules can be used in the following methods: PCR methods for synthesizing polymerase nucleic acids, methods for detecting the presence of an polymerase nucleic acid in a sample, screening methods for identifying nucleic acids encoding new polymerase family members.

The invention also includes methods for identifying nucleic acid molecules that encode members of the polymerase polypeptide family in addition to SEQ ID Nos:1, 3, 5, 7, 9, 11. In these methods, a sample, e.g., a nucleic acid library, such as a cDNA library, that contains a nucleic acid encoding a polymerase polypeptide is screened with a polymerase-specific probe, e.g., a polymerase-specific nucleic acid probe. Polymerase-specific nucleic acid probes are nucleic acid molecules (e.g., molecules containing DNA or RNA nucleotides, or combinations or modifications thereof) that specifically hybridize to nucleic acids encoding polymerase polypeptides, or to complementary sequences thereof. The term "polymerase-specific probe," in the context of this method of invention, refers to probes that bind to nucleic acids encoding polymerase polypeptides, or to complementary sequences thereof, to a detectably greater extent than to nucleic acids encoding other enzymes, or to complementary sequences thereof.

The invention facilitates production of polymerase-specific nucleic acid probes. Methods for obtaining such probes can be designed based on the amino acid sequences shown in FIG. 1. The probes, which can contain at least 12, e.g., at least 15, 25, 35, 50, 100, or 150 nucleotides, can be produced using any of several standard methods (see, e.g., Ausubel, et al., supra). For example, preferably, the probes are generated using PCR amplification methods. In these methods, primers are designed that correspond to polymerase-conserved sequences (see FIG. 1), which can include polymerase-specific amino acids, and the resulting PCR product is used as a probe to screen a nucleic acid library, such as a cDNA library.

The coding sequences for the polymerase enzymes of the present invention were identified by preparing an *Ammonifex degensii* KC4 genomic DNA library, for example, and screening the library for the clones having polymerase activity. Such methods for constructing a genomic gene library are well-known in the art. One means, for example, comprises shearing DNA isolated from *Ammonifex degensii* KC4 by physical disruption. A small amount of the sheared DNA is checked on an agarose gel to verify that the majority of the DNA is in the desired size range (approximately 3–6 kb). The DNA is then blunt ended using Mung Bean Nuclease, incubated at 37° C. and phenol/chloroform extracted. The DNA is then methylated using Eco RI Methylase. Eco RI linkers are then ligated to the blunt ends through the use of T4 DNA ligase and incubation at 4° C. The ligation reaction is then terminated and the DNA is cut-back with Eco RI restriction enzyme. The DNA is then size fractionated on a sucrose gradient following procedures known in the art, for example, Maniatis, T., et al., *Molecular Cloning*, Cold Spring Harbor Press, New York, 1982, which is hereby incorporated by reference in its entirety.

A plate assay is then performed to get an approximate concentration of the DNA. Ligation reactions are then performed and 1 (1 of the ligation reaction is packaged to construct a library. Packaging, for example, may occur through the use of purified (λgt11 phage arms cut with EcoRI and DNA cut with EcoRI after attaching EcoRI linkers. The DNA and (λgt11 arms are ligated with DNA ligase. The ligated DNA is then packaged into infectious phage particles. The packaged phages are used to infect *E. coli* cultures and the infected cells are spread on agar plates to yield plates carrying thousands of individual phage plaques. The library is then amplified.

Fragments of the full length gene of the present invention may be used as a hybridization probe for a cDNA or a genomic library to isolate the full length DNA and to isolate other DNAs which have a high sequence similarity to the gene or similar biological activity. Probes of this type have at least 10, preferably at least 15, and even more preferably at least 30 bases and may contain, for example, at least 50 or more bases. The probe may also be used to identify a DNA clone corresponding to a full length transcript and a genomic clone or clones that contain the complete gene including regulatory and promotor regions, exons, and introns.

The isolated nucleic acid sequences and other enzymes may then be measured for retention of biological activity characteristic to the enzyme of the present invention, for example, in an assay for detecting enzymatic polymerase activity. Such enzymes include truncated forms of polymerase, and variants such as deletion and insertion variants.

The polynucleotide of the present invention may be in the form of DNA which DNA includes cDNA, genomic DNA, and synthetic DNA. The DNA may be double-stranded or single-stranded, and if single stranded may be the coding strand or non-coding (anti-sense) strand. The coding sequence which encodes the mature enzyme may be identical to the coding sequences shown in FIGS. 1–6, or may be a different coding sequence which coding sequence, as a result of the redundancy or degeneracy of the genetic code, encodes the same mature enzyme as the DNA of FIGS. 1–6 (e.g., SEQ ID NO:1).

The polynucleotide which encodes the mature enzyme of FIG. 1 (e.g., SEQ ID NO:1) may include, but is not limited to: only the coding sequence for the mature enzyme; the coding sequence for the mature enzyme and additional coding sequence such as a leader sequence or a proprotein sequence; the coding sequence for the mature enzyme (and optionally additional coding sequence) and non-coding sequence, such as introns or non-coding sequence 5' and/or 3' of the coding sequence for the mature enzyme.

Thus, the term "polynucleotide encoding an enzyme (protein)" encompasses a polynucleotide which includes only coding sequence for the enzyme as well as a polynucleotide which includes additional coding and/or non-coding sequence.

The present invention further relates to variants of the hereinabove described polynucleotides which encode for fragments, analogs and derivatives of the enzyme having the deduced amino acid sequence of FIG. 1 (e.g., SEQ ID NO:2). The variant of the polynucleotide may be a naturally occurring allelic variant of the polynucleotide or a non-naturally occurring variant of the polynucleotide.

Thus, the present invention includes polynucleotides encoding the same mature enzyme as shown in FIG. 1 as well as variants of such polynucleotides which variants encode for a fragment, derivative or analog of the enzyme of FIG. 1. Such nucleotide variants include deletion variants, substitution variants and addition or insertion variants.

As hereinabove indicated, the polynucleotide may have a coding sequence which is a naturally occurring allelic variant of the coding sequence shown in FIG. 1. As known in the art, an allelic variant is an alternate form of a polynucleotide sequence which may have a substitution, deletion or addition of one or more nucleotides, which does not substantially alter the function of the encoded enzyme.

The present invention also includes polynucleotides, wherein the coding sequence for the mature enzyme may be fused in the same reading frame to a polynucleotide sequence which aids in expression and secretion of an enzyme from a host cell, for example, a leader sequence which functions to control transport of an enzyme from the cell. The enzyme having a leader sequence is a preprotein and may have the leader sequence cleaved by the host cell to form the mature form of the enzyme. The polynucleotides may also encode for a proprotein which is the mature protein plus additional 5' amino acid residues. A mature protein having a prosequence is a proprotein and is an inactive form of the protein. Once the prosequence is cleaved an active mature protein remains.

Thus, for example, the polynucleotide of the present invention may encode for a mature enzyme, or for an enzyme having a prosequence or for an enzyme having both a prosequence and a presequence (leader sequence).

The present invention further relates to polynucleotides which hybridize to the hereinabove-described sequences if there is at least 70%, preferably at least 90%, and more preferably at least 95% identity between the sequences. The present invention particularly relates to polynucleotides which hybridize under stringent conditions to the hereinabove-described polynucleotides. As herein used, the term "stringent conditions" means hybridization will occur only if there is at least 95% and preferably at least 97% identity between the sequences. The polynucleotides which hybridize to the hereinabove described polynucleotides in a preferred embodiment encode enzymes which either retain substantially the same biological function or activity as the mature enzyme encoded by the DNA of FIG. 1.

Alternatively, the polynucleotide may have at least 15 bases, preferably at least 30 bases, and more preferably at least 50 bases which hybridize to a polynucleotide of the present invention and which has an identity thereto, as hereinabove described, and which may or may not retain activity. For example, such polynucleotides may be employed as probes for the polynucleotide of SEQ ID NO:1, for example, for recovery of the polynucleotide or as a PCR primer.

Thus, the present invention is directed to polynucleotides having at least a 70% identity, preferably at least 90% identity and more preferably at least a 95% identity to a polynucleotide which encodes the enzyme of SEQ ID NO:1 as well as fragments thereof, which fragments have at least 30 bases and preferably at least 50 bases to enzymes encoded by such polynucleotides.

The present invention further relates to an enzyme which has the deduced amino acid sequence of FIGS. 1–6, as well as fragments, analogs and derivatives of such enzyme.

The terms "fragment," "derivative" and "analog" when referring to the enzyme of FIG. 1 means a enzyme which retains essentially the same biological function or activity as such enzyme. Thus, an analog includes a proprotein which can be activated by cleavage of the proprotein portion to produce an active mature enzyme.

The enzyme of the present invention may be a recombinant enzyme, a natural enzyme or a synthetic enzyme, preferably a recombinant enzyme.

The fragment, derivative or analog of the enzyme of FIG. 1 may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the mature enzyme is fused with another compound, such as a compound to increase the half-life of the enzyme (for example, polyethylene glycol), or (iv) one in which the additional amino acids are fused to the mature enzyme, such as a leader or secretory sequence or a sequence which is employed for purification of the mature enzyme or a proprotein sequence. Such fragments, derivatives and analogs are deemed to be within the scope of those skilled in the art from the teachings herein.

The enzymes and polynucleotides of the present invention are preferably provided in an isolated form, and preferably are purified to homogeneity.

The term "isolated" means that the material is removed from its original environment (e.g., the natural environment if it is naturally occurring). For example, a naturally-occurring polynucleotide or enzyme present in a living animal is not isolated, but the same polynucleotide or enzyme, separated from some or all of the coexisting materials in the natural system, is isolated. Such polynucleotides could be part of a vector and/or such polynucleotides or enzymes could be part of a composition, and still be isolated in that such vector or composition is not part of its natural environment.

The enzymes of the present invention include an enzyme of FIGS. 1–6 (in particular the mature enzyme) as well as enzymes which have at least 70% similarity (preferably at least 70% identity) to an enzyme of FIGS. 1–6 and more preferably at least 90% similarity (more preferably at least 90% identity) to an enzymes of FIGS. 1–6 and still more preferably at least 95% similarity (still more preferably at least 95% identity) to an enzyme of FIGS. 1–6 and also include portions of such enzymes with such portion of the enzyme generally containing at least 30 amino acids and more preferably at least 50 amino acids.

As known in the art "similarity" between two enzymes is determined by comparing the amino acid sequence and its conserved amino acid substitutes of one enzyme to the sequence of a second enzyme. Similarity may be determined by procedures which are well-known in the art, for example, a BLAST program (Basic Local Alignment Search Tool at the National Center for Biological Information).

A variant, i.e. a "fragment", "analog" or "derivative" enzyme, and reference enzyme may differ in amino acid sequence by one or more substitutions, additions, deletions, fusions and truncations, which may be present in any combination.

Among preferred variants are those that vary from a reference by conservative amino acid substitutions. Such substitutions are those that substitute a given amino acid in a polypeptide by another amino acid of like characteristics. Typically seen as conservative substitutions are the replacements, one for another, among the aliphatic amino acids Ala, Val, Leu and Ile; interchange of the hydroxyl residues Ser and Thr, exchange of the acidic residues Asp and Glu, substitution between the amide residues Asn and Gln, exchange of the basic residues Lys and Arg and replacements among the aromatic residues Phe, Tyr.

Most highly preferred are variants which retain the same biological function and, activity as the reference polypeptide from which it varies.

Fragments or portions of the enzymes of the present invention may be employed for producing the corresponding full-length enzyme by peptide synthesis; therefore, the fragments may be employed as intermediates for producing the full-length enzymes. Fragments or portions of the polynucleotides of the present invention may be used to synthesize full-length polynucleotides of the present invention.

The present invention also relates to vectors which include polynucleotides of the present invention, host cells which are genetically engineered with vectors of the invention and the production of enzymes of the invention by recombinant techniques.

Host cells are genetically engineered (transduced or transformed or transfected) with the vectors containing the polynucleotides of this invention. Such vectors may be, for example, a cloning vector or an expression vector. The vector may be, for example, in the form of a plasmid, a viral particle, a phage, etc. The engineered host cells can be cultured in conventional nutrient media modified as appropriate for activating promoters, selecting transformants or amplifying the genes of the present invention. The culture conditions, such as temperature, pH and the like, are those previously used with the host cell selected for expression, and will be apparent to the ordinarily skilled artisan.

The polynucleotides of the present invention may be employed for producing enzymes by recombinant techniques. Thus, for example, the polynucleotide may be included in any one of a variety of expression vectors for expressing an enzyme. Such vectors include chromosomal, nonchromosomal and synthetic DNA sequences, e.g., derivatives of SV40; bacterial plasmids; phage DNA; baculovirus; yeast plasmids; vectors derived from combinations of plasmids and phage DNA, viral DNA such as vaccinia, adenovirus, fowl pox virus, and pseudorabies. However, any other vector may be used as long as it is replicable and viable in the host.

The appropriate DNA sequence may be inserted into the vector by a variety of procedures. In general, the DNA sequence is inserted into an appropriate restriction endonuclease site(s) by procedures known in the art. Such procedures and others are deemed to be within the scope of those skilled in the art.

The DNA sequence in the expression vector is operatively linked to an appropriate expression control sequence(s) (promoter) to direct mRNA synthesis. As representative examples of such promoters, there may be mentioned: LTR or SV40 promoter, the E. coli. lac or tip, the phage lambda $P_L$ promoter and other promoters known to control expression of genes in prokaryotic or eukaryotic cells or their viruses. The expression vector also contains a ribosome binding site for translation initiation and a transcription terminator. The vector may also include appropriate sequences for amplifying expression.

In addition, the expression vectors preferably contain one or more selectable marker genes to provide a phenotypic trait for selection of transformed host cells such as dihydrofolate reductase or neomycin resistance for eukaryotic cell culture, or such as tetracycline or ampicillin resistance in E. coli.

The vector containing the appropriate DNA sequence as hereinabove described, as well as an appropriate promoter or control sequence, may be employed to transform an appropriate host to permit the host to express the protein.

As representative examples of appropriate hosts, there may be mentioned: bacterial cells, such as E. coli, Streptomyces, Bacillus subtilis; fungal cells, such as yeast; insect cells such as Drosophila S2 and Spodoptera Sf9; animal cells such as CHO, COS or Bowes melanoma; adenoviruses; plant cells, etc. The selection of an appropriate host is deemed to be within the scope of those skilled in the art from the teachings herein.

More particularly, the present invention also includes recombinant constructs comprising one or more of the sequences as broadly described above. The constructs comprise a vector, such as a plasmid or viral vector, into which a sequence of the invention has been inserted, in a forward or reverse orientation. In a preferred aspect of this embodiment, the construct further comprises regulatory sequences, including, for example, a promoter, operably linked to the sequence. Large numbers of suitable vectors and promoters are known to those of skill in the art, and are commercially available. The following vectors are provided by way of example; Bacterial: pQE70, pQE60, pQE-9 (Qiagen), pBluescript II (Stratagene); pTRC99a; pKK223-3, pDR540, pRIT2T (Pharmacia); Eukaryotic: pXT1, pSG5 (Stratagene) pSVK3, pBPV, pMSG, pSVLSV40 (Pharmacia). However, any other plasmid or vector may be used as long as they are replicable and viable in the host.

Promoter regions can be selected from any desired gene using CAT (chloramphenicol transferase) vectors or other vectors with selectable markers. Two appropriate vectors are pKK232-8 and pCM7. Particular named bacterial promoters include lac, lacZ, T3, T7, gpt, lambda $P_R$, $P_L$ and trp. Eukaryotic promoters include CMV immediate early, HSV thymidine kinase, early and late SV40, LTRs from retrovirus, and mouse metallothionein-I. Selection of the appropriate vector and promoter is well within the level of ordinary skill in the art.

In a further embodiment, the present invention relates to host cells containing the above-described constructs. The host cell can be a higher eukaryotic cell, such as a mammalian cell, or a lower eukaryotic cell, such as a yeast cell, or the host cell can be a prokaryotic cell, such as a bacterial cell. Introduction of the construct into the host cell can be effected by calcium phosphate transfection, DEAE-Dextran mediated transfection, or electroporation (Davis, L., Dibner, M., Battey, I., Basic Methods in Molecular Biology, (1986)).

The constructs in host cells can be used in a conventional manner to produce the gene product encoded by the recombinant sequence. Alternatively, the enzymes of the invention can be synthetically produced by conventional peptide synthesizers.

Mature proteins can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook et al., Molecular Cloning: A Laboratory Manual, Second Edition, Cold Spring Harbor, N.Y., (1989), the disclosure of which is hereby incorporated by reference.

Transcription of the DNA encoding the enzymes of the present invention by higher eukaryotes is increased by inserting an enhancer sequence into the vector. Enhancers are cis-acting elements of DNA, usually about from 10 to 300 bp that act on a promoter to increase its transcription. Examples include the SV40 enhancer on the late side of the replication origin bp 100 to 270, a cytomegalovirus early promoter enhancer, the polyoma enhancer on the late side of the replication origin, and adenovirus enhancers.

Generally, recombinant expression vectors will include origins of replication and selectable markers permitting transformation of the host cell, e.g., the ampicillin resistance gene of *E. coli* and *S. cerevisiae* TRP1 gene, and a promoter derived from a highly-expressed gene to direct transcription of a downstream structural sequence. Such promoters can be derived from operons encoding glycolytic enzymes such as 3-phosphoglycerate kinase (PGK), Å-factor, acid phosphatase, or heat shock proteins, among others. The heterologous structural sequence is assembled in appropriate phase with translation initiation and termination sequences, and preferably, a leader sequence capable of directing secretion of translated enzyme. Optionally, the heterologous sequence can encode a fusion enzyme including an N-terminal identification peptide imparting desired characteristics, e.g., stabilization or simplified purification of expressed recombinant product.

Useful expression vectors for bacterial use are constructed by inserting a structural DNA sequence encoding a desired protein together with suitable translation initiation and termination signals in operable reading phase with a functional promoter. The vector will comprise one or more phenotypic selectable markers and an origin of replication to ensure maintenance of the vector and to, if desirable, provide amplification within the host. Suitable prokaryotic hosts for transformation include *E. coli, Bacillus subtilis, Salmonella typhimurium* and various species within the genera Pseudomonas, Streptomyces, and Staphylococcus, although others may also be employed as a matter of choice.

As a representative but nonlimiting example, useful expression vectors for bacterial use can comprise a selectable marker and bacterial origin of replication derived from commercially available plasmids comprising genetic elements of the well known cloning vector pBR322 (ATCC 37017). Such commercial vectors include, for example, pKK223-3 (Pharmacia Fine Chemicals, Uppsala, Sweden) and GEM1 (Promega Biotec, Madison, Wis., USA). These pBR322 "backbone" sections are combined with an appropriate promoter and the structural sequence to be expressed.

Following transformation of a suitable host strain and growth of the host strain to an appropriate cell density, the selected promoter is induced by appropriate means (e.g., temperature shift or chemical induction) and cells are cultured for an additional period.

Cells are typically harvested by centrifugation, disrupted by physical or chemical means, and the resulting crude extract retained for further purification.

Microbial cells employed in expression of proteins can be disrupted by any convenient method, including freeze-thaw cycling, sonication, mechanical disruption, or use of cell lysing agents, such methods are well known to those skilled in the art.

Various mammalian cell culture systems can also be employed to express recombinant protein. Examples of mammalian expression systems include the COS-7 lines of monkey kidney fibroblasts, described by Gluzman, Cell, 23:175 (1981), and other cell lines capable of expressing a compatible vector, for example, the C127, 3T3, CHO, HeLa and BHK cell lines. Mammalian expression vectors will comprise an origin of replication, a suitable promoter and enhancer, and also any necessary ribosome binding sites, polyadenylation site, splice donor and acceptor sites, transcriptional termination sequences, and 5' flanking nontranscribed sequences. DNA sequences derived from the SV40 splice, and polyadenylation sites may be used to provide the required nontranscribed genetic elements.

The enzyme can be recovered and purified from recombinant cell cultures by methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Protein refolding steps can be used, as necessary, in completing configuration of the mature protein. Finally, high performance liquid chromatography (HPLC) can be employed for final purification steps.

The enzymes of the present invention may be a naturally purified product, or a product of chemical synthetic procedures, or produced by recombinant techniques from a prokaryotic or eukaryotic host (for example, by bacterial, yeast, higher plant, insect and mammalian cells in culture). Depending upon the host employed in a recombuiarit production procedure, the enzymes of the present invention may be. glycosylated or may be non-glycosylated. Enzymes of the invention may or may not also include an initial methionine amino acid residue.

The enzyme of this invention may be employed for any purpose in which such enzyme activity is necessary or desired. In a preferred embodiment the enzyme is employed for catalyzing DNA synthesis by addition of deoxynucleotides to the 3' end of a polynucleotide chain, using a complementary polynucleotide strand as a template.

In a preferred embodiment, the enzyme of the present invention is a thermostable enzyme which is stable to heat and is heat resistant and polymerizes DNA, i.e., the enzyme is able to renature and regain activity after a brief (i.e., 5 to 30 seconds), or longer period, for example, minutes or hours, exposure to temperatures of up to 70° C. and has a temperature optimum above 60° C.

The enzymes, their fragments or other derivatives, or analogs thereof, or cells expressing them can be used as an immunogen to produce antibodies thereto. These antibodies can be, for example, polyclonal or monoclonal antibodies. The present invention also includes chimeric, single chain, and humanized antibodies, as well as Fab fragments, or the product of an Fab expression library. Various procedures known in the art may be used for the production of such antibodies and fragments.

Antibodies generated against the enzymes corresponding to a sequence of the present invention can be obtained by direct injection of the enzymes into an animal or by administering the enzymes to an animal, preferably a nonhuman. The antibody so obtained will then bind the enzymes itself. In this manner, even a sequence encoding only a fragment of the enzymes can be used to generate antibodies binding the whole native enzymes. Such antibodies can then be used to isolate the enzyme from cells expressing that enzyme.

For preparation of monoclonal antibodies, any technique which provides antibodies produced by continuous cell line cultures can be used. Examples include the hybridoma technique (Kohler and Milstein, 1975, Nature, 256:495–497), the trioma technique, the human B-cell hybridoma technique (Kozbor et al., 1983, Immunology Today 4:72), and the EBV-hybridoma technique to produce human monoclonal antibodies (Cole, et al., 1985, in Monoclonal Antibodies and Cancer Therapy, Alan R. Liss, Inc., pp. 77–96).

Techniques described for the production of single chain antibodies (U.S. Pat. No. 4,946,778) can be adapted to produce single chain antibodies to immunogenic enzyme products of this invention. Also, transgenic mice may be used to express humanized antibodies to immunogenic enzyme products of this invention.

Antibodies generated against the enzyme of the present invention may be used in screening for similar enzymes from other organisms and samples. Such screening techniques are known in the art, for example, one such screening assay is described in "Methods for Measuring Cellulase Activities", *Methods in Enymology*, Vol 160, pp. 87–116, which is hereby incorporated by reference in its entirety. Antibodies may also be employed as a probe to screen gene libraries generated from this or other organisms to identify this or cross reactive activities.

Isolation and purification of polypeptides produced in the systems described above can be carried out using conventional methods, appropriate for the particular system. For example, preparative chromatography and immunological separations employing antibodies, such as monoclonal or polyclonal antibodies, can be used.

The term "antibody," as used herein, refers to intact immunoglobulin molecules, as well as fragments of immunoglobulin molecules, such as Fab, Fab', (Fab')$_2$, Fv, and SCA fragments, that are capable of binding to an epitope of a polymerase polypeptide. These antibody fragments, which retain some ability to selectively bind to the antigen (e.g., a polymerase antigen) of the antibody from which they are derived, can be made using well known methods in the art (see, e.g., Harlow and Lane, supra), and are described further, as follows.

(1) A Fab fragment consists of a monovalent antigen-binding fragment of an antibody molecule, and can be produced by digestion of a whole antibody molecule with the enzyme papain, to yield a fragment consisting of, an intact light chain and a portion of a heavy chain.

(2) A Fab' fragment of an antibody molecule can be obtained by treating a whole antibody molecule with pepsin, followed by reduction, to yield a molecule consisting of an intact light chain and a portion of a heavy chain. Two Fab' fragments are obtained per antibody molecule treated in this manner.

(3) A (Fab')$_2$ fragment of an antibody can be obtained by treating a whole antibody molecule with the enzyme pepsin, without subsequent reduction. A (Fab')$_2$ fragment is a dimer of two Fab' fragments, held together by two disulfide bonds.

(4) An Fv fragment is defined as a genetically engineered fragment containing the variable region of a light chain and the variable region of a heavy chain expressed as two chains.

(5) A single chain antibody ("SCA") is a genetically engineered single chain molecule containing the variable region of a light chain and the variable region of a heavy chain, linked by a suitable, flexible polypeptide linker.

As used in this invention, the term "epitope" refers to an antigenic determinant on an antigen, such as a polymerase polypeptide, to which the paratope of an antibody, such as a polymerase-specific antibody, binds. Antigenic determinants usually consist of chemically active surface groupings of molecules, such as amino acids or sugar side chains, and can have specific three-dimensional structural characteristics, as well as specific charge characteristics.

As is mentioned above, antigens that can be used in producing polymerase-specific antibodies include polymerase polypeptides, e.g., any of the polymerases shown in FIGS. 1–X polypeptide fragments. The polypeptide or peptide used to immunize an animal can be obtained by standard recombinant, chemical synthetic, or purification methods. As is well known in the art, in order to increase immunogenicity, an antigen can be conjugated to a carrier protein. Commonly used carriers include keyhole limpet hemocyanin (KLH), thyroglobulin, bovine serum albumin (BSA), and tetanus toxoid. The coupled peptide is then used to immunize the animal (e.g., a mouse, a rat, or a rabbit). In addition to such carriers, well known adjuvants can be administered with the antigen to facilitate induction of a strong immune response.

Polymerase-specific polyclonal and monoclonal antibodies can be purified, for example, by binding to, and elution from, a matrix containing a polymerase polypeptide, e.g., the polymerase polypeptide (or fragment thereof) to which the antibodies were raised. Additional methods for antibody purification and concentration are well known in the art and can be practiced with the polymerase-specific antibodies of the invention (see, for example, Coligan, et al., Unit 9, Current Protocols in Immunology, Wiley Interscience, 1994).

Anti-idiotype antibodies corresponding to polymerase-specific antigens are also included in the invention, and can be produced using standard methods. These antibodies are raised to polymerase-specific antibodies, and thus mimic polymerase-specific epitopes.

The members of a pair of molecules (e.g., an antibody-antigen pair or a nucleic acid pair) are said to "specifically bind" to each other if they bind to each other with greater affinity than to other, non-specific molecules. For example, an antibody raised against an antigen to which it binds more efficiently than to a non-specific protein can be described as specifically binding to the antigen. (Similarly, a nucleic acid probe can be described as specifically binding to a nucleic acid target if it forms a specific duplex with the target by base pairing interactions (see above).)

The present invention is further described with reference to the following examples; however, it is to be understood that the present invention is not limited to such examples. All parts or amounts, unless otherwise specified, are by weight.

In one aspect of the invention, a method for producing a polymerase enzyme, such as those shown in FIGS. 1–6, is provided. The method includes growing a host cell which contains a polynucleotide encoding the enzyme (e.g., SEQ ID Nos:2, 4, 6, 8, 10, 12), under conditions which allow the expression of the nucleic acid, and isolating the enzyme encoded by the nucleic acid. Methods of culturing the host cell are described in the Examples and are known by those of skill in the art.

In order to facilitate understanding of the following examples certain frequently occurring methods and/or terms will be described.

"Plasmids" are designated by a lower case p preceded and/or followed by capital letters and/or numbers. The starting plasmids herein are either commercially available, publicly available on an unrestricted basis, or can be constructed from available plasmids in accord with published procedures. In addition, equivalent plasmids to those described are known in the art and will be apparent to the ordinarily skilled artisan.

"Digestion" of DNA refers to catalytic cleavage of the DNA with a restriction enzyme that acts only at certain sequences in the DNA. The various restriction enzymes used herein are commercially available and their reaction conditions, cofactors and other requirements were used as would be known to the ordinarily skilled artisan. For analytical purposes, typically 1 µg of plasmid or DNA fragment is used with about 2 units of enzyme in about 20 µl of buffer solution. For the purpose of isolating DNA fragments for plasmid construction, typically 5 to 50 µg of DNA are digested with 20 to 250 units of enzyme in a larger volume. Appropriate buffers and substrate amounts for particular restriction enzymes are specified by the manufacturer. Incubation times of about 1 hour at 37° C. are ordinarily used, but may vary in accordance with the supplier's instructions. After digestion the reaction is electrophoresed directly on a polyacrylamide gel to isolate the desired fragment.

Size separation of the cleaved fragments is generally performed using 8 percent polyacrylamide gel described by Goeddel, D. et al., Nucleic Acids Res., 8:4057 (1980), for example.

"Oligonucleotides" refers to either a single stranded polydeoxynucleotide or two complementary polydeoxynucleotide strands which may be chemically synthesized. Such synthetic oligonucleotides may or may not have a 5' phosphate. Those that do not will not ligate to another oligonucleotide without adding a phosphate with an ATP in the presence of a kinase. A synthetic oligonucleotide will ligate to a fragment that has not been dephosphorylated.

"Ligation" refers to the process of forming phosphodiester bonds between two double stranded nucleic acid fragments (Maniatis, T., et al., Id., p. 146). Unless otherwise provided, ligation may be accomplished using known buffers and conditions with 10 units of T4 DNA ligase ("ligase") per 0.5 (g of approximately equimolar amounts of the DNA fragments to be ligated.

Unless otherwise stated, transformation was performed as described in the method of Sambrook, Fritsch and Maniatis, 1989. The following examples are intended to illustrate, but not to limit, the invention. While the procedures described in the examples are typical of those that can be used to carry out certain aspects of the invention, other procedures known to those skilled in the art can also be used. The following materials and methods were used in carrying out the experiments described in the examples.

EXAMPLE 1

DNA Isolation and Library Construction

The following outlines the procedures used to generate a gene library from a sample.

Isolate DNA.
    IsoQuick Procedure as per manufacturer's instructions (Orca, Research Inc., Bothell, Wash.).
Shear DNA
    Vigorously push and pull DNA through a 25G double-hub needle and 1-cc syringes about 500 times.
    Check a small amount (0.5 µg) on a 0.8% agarose gel to make sure the majority of the DNA is in the desired size range (about 3–6 kb).
Blunt DNA
    Add:
    $H_2O$ to a final volume of 405 µl
    45 µl 10× Mung Bean Buffer
    2.0 µl Mung Bean Nuclease (150 u/µl)
    Incubate 37° C., 15 minutes.
    Phenol/chloroform extract once.
    Chloroform extract once.
    Add 1 ml ice cold ethanol to precipitate.
    Place on ice for 10 minutes.
    Spin in microfuge, high speed, 30 minutes.
    Wash with 1 ml 70% ethanol.
    Spin in microfuge, high speed, 10 minutes and dry.
Methylate DNA
    Gently resuspend DNA in 26 µl TE.
    Add:
    4.0 µl 10× EcoR I Methylase Buffer
    0.5 µl SAM (32 mM)
    5.0 µl EcoR I Methylase (40 u/µl)
    Incubate 37°, 1 hour.
Insure Blunt Ends
    Add to the methylation reaction:
    5.0 µl 100 mM $MgCl_2$
    8.0 µl dNTP mix (2.5 mM of each dGTP, dATP, dTTP, dCTP)
    4.0 µl Klenow (5 u/µl)
    Incubate 12° C., 30 minutes.
    Add 450 µl 1× STE.
    Phenol/chloroform extract once.
    Chloroform extract once.
    Add 1 ml ice cold ethanol to precipitate and place on ice for 10 minutes.
    Spin in microfuge, high speed, 30 minutes.
    Wash with 1 ml 70% ethanol.
    Spin in microfuge, high speed, 10 minutes and dry.
Adaptor Ligation
    Gently resuspend DNA in 8 µl EcoR I adaptors (from Stratagene's cDNA Synthesis Kit).
    Add:
    1.0 µl 10× Ligation Buffer
    1.0 µl 10 mM rATP
    1.0 µl T4 DNA Ligase (4 u/µl)
    Incubate 4° C., 2 days.
Phosphorylate Adaptors
    Heat kill ligation reaction 70° C., 30 minutes.
    Add:
    1.0 µl 10× Ligation Buffer
    2.0 µl 10 mM rATP
    6.0 µl $H_2O$
    1.0 µl Polynucleotide kinase (PNK)
    Incubate 37° C., 30 minutes.
    Add 31 µl $H_2O$ and 5 µl 10× STE.
    Size fractionate on a Sephacryl S-500 spin column (pool fractions 1–3).
    Phenol/chloroform extract once.
    Chloroform extract once.
    Add ice cold ethanol to precipitate.
    Place on ice, 10 minutes.
    Spin in microfuge, high speed, 30 minutes.
    Wash with 1 ml 70% ethanol.
    Spin in microfuge, high speed, 10 minutes and dry.
    Resuspend in 10.5 µl TE buffer.
    Do not plate assay. Instead, ligate directly to arms as above except use 2.5 µl of
    DNA and no water.
Sucrose Gradient (2.2 ml) Size Fractionation
    Heat sample to 65° C., 10 minutes.
    Gently load on 2.2 ml sucrose gradient.
    Spin in mini-ultracentrifuge, 45K, 20° C., 4 hours (no brake).

Collect fractions by puncturing the bottom of the gradient tube with a 20G needle and allowing the sucrose to flow through the needle. Collect the first 20 drops in a Falcon 2059 tube then collect 10 1-drop fractions (labelled 1–10). Each drop is about 60 $\mu$l in volume.

Run 5 $\mu$l of each fraction on a 0.8% agarose gel to check the size.

Pool fractions 1–4 (about 10–1.5 kb) and, in a separate tube, pool fractions 5–7 (about 5–0.5 kb).

Add 1 ml ice cold ethanol to precipitate and place on ice for 10 minutes.

Spin in microfuge, high speed, 30 minutes.

Wash with 1 ml 70% ethanol.

Spin in microfuge, high speed, 10 minutes and dry.

Resuspend each in 10 $\mu$l TE buffer.

Test Ligation to Lambda Arms

Plate assay to get an approximate concentration. Spot 0.5 $\mu$l of the sample on agarose containing ethidium bromide along with standards (DNA samples of known concentration). View in UV light and estimate concentration compared to the standards. Fraction 1–4=>1.0 $\mu$g/$\mu$l. Fraction 5–7=500 ng/$\mu$l.

Prepare the following ligation reactions (5 $\mu$l reactions) and incubate 4° C., overnight:

| Sample | H$_2$O | 10 X Ligase Buffer | 10 mM rATP | Lambda arms (ZAP) | Insert DNA | T4 DNA Ligase (4 u/$\mu$l) |
|---|---|---|---|---|---|---|
| Fraction 1–4 | 0.5 $\mu$l | 0.5 $\mu$l | 0.5 $\mu$l | 1.0 $\mu$l | 2.0 $\mu$l | 0.5 $\mu$l |
| Fraction 5–7 | 0.5 $\mu$l | 0.5 $\mu$l | 0.5 $\mu$l | 1.0 $\mu$l | 2.0 $\mu$l | 0.5 $\mu$l |

Test Package and Plate

Package the ligation reactions following manufacturer's protocol.

Stop packaging reactions with 500 $\mu$l SM buffer and pool packaging that came from the same ligation.

Titer 1.0 $\mu$l of each on appropriate host (OD$_{600}$=1.0) [XLI-Blue MRF]

Add 200 $\mu$l host (in mM MgSO$_4$) to Falcon 2059 tubes

Inoculate with 1 $\mu$l packaged phage

Incubate 37° C., 15 minutes

Add about 3 ml 48° C. top agar

[50 ml stock containing 150 $\mu$l IPTG (0.5M) and 300 $\mu$l X-GAL (350 mg/ml)]

Plate on 100 mm plates and incubate 37° C., overnight.

Amplification of Libraries (5.0×10$^5$ recombinants from each library)

Add 3.0 ml host cells (OD$_{600}$=1.0) to two 50 ml conical tube.

Inoculate with 2.5×10$^5$ pfu per conical tube.

Incubate 37° C., 20 minutes.

Add top agar to each tube to a final volume of 45 ml.

Plate the tube across five 150 mm plates.

Incubate 37° C., 6–8 hours or until plaques are about pin-head in size.

Overlay with 8–10 ml SM Buffer and place at 4° C. overnight (with gentle rocking if possible).

Harvest Phage

Recover phage suspension by pouring the SM buffer off each plate into a 50 ml conical tube.

Add 3 ml chloroform, shake vigorously and incubate at room temperature, 15 minutes.

Centrifuge at 2K rpm, 10 minutes to remove cell debris.

Pour supernatant into a sterile flask, add 500 $\mu$l chloroform.

Store at 4° C.

Titer Amplified Library

Make Serial Dilutions:

10$^{-5}$=1 $\mu$l amplified phage in 1 ml SM Buffer

10$^{-6}$=1 $\mu$l of the 10$^3$ dilution in 1 ml SM Buffer

Add 200 $\mu$l host (in 10 mM MgSO$_4$) to two tubes.

Inoculate one with 10 $\mu$l 10$^{-6}$ dilution (10$^{-5}$).

Inoculate the other with 1 $\mu$l 10$^{-6}$ dilution (10$^{-6}$).

Incubate 37° C., 15 minutes.

Add about 3 ml 48° C. top agar.

[50 ml stock containing 150 $\mu$l IPTG (0.5M) and 375 $\mu$l X-GAL (350 mg/ml)]

Plate on 100 mm plates and incubate 37° C., overnight.

Excise the ZAP II library to create the pBluescript library according to manufacturers protocols (Stratagene).

EXAMPLE 2

Activated Calf Thymus DNA Polymerase Assay

Streak Out the Clone to Isolation:

1. Inoculate 5 ml LB/Amp/Meth/Kan culture with isolated clone
2. Grow to turbidity
3. Inoculate a 50 ml culture of LB/Amp/Meth/Kan Grow to OD600 of 0.7 to 0.9; induce culture with IPTG at a final concentration of 1 mM for 3 hours Centrifuge at 4500 RPM for 20 minutes and discard supernate Resuspend pellet in 3 mls of 20 mM Tris pH 8.0 and sonicate twice for 1 minute each Microcentrifuge 1 ml of sonicate for 30 minutes at 4° C.

Remove 1 ul of the sonicate supernatent and add to 10 $\mu$l of the following Activated Calf Thymus Reaction Cocktail in a 0.5 ml eppendorf:

5 units/ml activated calf thymus DNA (Pharmacia 27–4575-01)

1 mMDTT 40 mg/ml BSA 50 mM dATP, 50 uM dCTP, 50 uM dGTP, 5 uM dTTP 50 mM Tris pH 7.6

5 mM MgCl2

50 $\mu$Ci/ml H$^3$-dTTP bring to volume with H2O

Incubate at 70° C. for 10–30 minutes

Stop reaction by cooling the tube

Spot sample onto Whatman DE-81 filter paper (catalog#3658-323)

Dry completely

Wash filters in 2× SSC five times for 2 minutes each

Final wash in 100% ethanol to remove most of remaining water

Allow the filters to dry to completion

Count incorporation of H$^3$-dTTP using a scintillation counter

The incorporation of nucleotides by the polymerase is proportional to counts, by at least five fold over background. (Maki,H, et al, J.Biol.Chem. (1988) 263:6570–6578 and Tabor, et al, U.S. Pat. No. 4,795,699).

EXAMPLE 3

PCR Screening

Polymerase sequences from *Thermococcus litoralis*, Pyrococcus GB-D (Deep Vent), and *Pyrococcus furimosus* were scanned to determine conserved regions. The following nucleic acid sequences were identified and corresponding amino acid sequences were utilized to derive degenerate oligonucleotide primers to be used in downstream screening:

*Thermococcus litoralis*: 37–45, 1045–1051

Pyrococcus GB-D (Deep Vent): 37–45, 1042–1049

*Pyrococcus furiosus*: 37–45, 505–512

The following corresponding amino acid sequences were used to produce degenerate oligonucleotide primers:

YIYALL$^K$/RDD

WY$^C$/SKECAE

The primers have been labeled Poldgen1 forward and Poldgen2 reverse:

Poldgen1 forward (26 mer): 5'-TA$^C$/TAT$^A$/TTA$^C$/TGCTCT$^C$/TCTCA$^A$/GAGATGA-3'

Poldgen2 reverse (23 mer): 5'-TC$^A$/TGC$^A$/GCA$^c$/TTC$^C$/TTTACA$^A$/GTACCA-3'

These primers were used to amplify potential polymerase genes directly from genomic DNA (Template DNA).

100 µl PCR conditions:

1 µl Poldgen1 forward (500 ng/µl)

1 µl Poldgen2 reverse (500 ng/µl)

1 µl 25 mM dNTP mix

1 µl Template DNA (100 ng/µl)

1 µl TaqPlus Polymerase (Stratagene)

10 µl 10× low salt reaction buffer (Stratagene)

85 µl H$_2$O

| Number of Cycles | Temperature | Time |
|---|---|---|
| 2 | 95° C. | 30 seconds |
|  | 42° C. | 30 seconds |
|  | 72° C. | 2 minutes, 30 seconds |
| 30 | 95° C. | 30 seconds |
|  | 50° C. | 30 seconds |
|  | 72° C. | 2 minutes, 30 seconds |
| 1 | 72° C. | 10 minutes |

PCR products (1.4 kb bands from both organisms) were phenol chloroform extracted (ref. Maniatis) and cloned using the TA cloning system into the pGemT PCR Cloning Vector (Promega) using the following ligation reaction:

0.5 µl pGemT Cloning Vector (50 ng/µl)

2 µl PCR Product (~1000 ng/µl)

2 µl rATP (10 mM)

2 µl 10× T4 Ligase Buffer

1 µl T4 Ligase 12.5 µl H$_2$O

Incubate 4° C. overnight.

2.5 µl of the above reaction was transformed into XL1-Blue MRF' competent cells (Stratagene)

1.4 kb PCR products were also restriction analyzed using the appropriate restriction enzymes:

Potential clones were verified by restriction analysis and sequenced.

BLASTX and BLASTN database comparisons of the sequences indicated whether the sequences were homologous to the nucleic acid sequence of a known polymerase from another organism. Amplification primers were then generated to both ends of the known polymerase gene, and were used in an amplification reaction on the genomic DNA in an attempt to pull out a full length polymerase gene from this organism. These primers include restriction sites and a new Ribosome Binding Site for downstream processing of the gene:

PCR Conditions:

1 µl forward primer (250 ng/µl)

1 µl reverse primer (250 ng/µl)

1 µl 25 mM dNTP

1 µl template DNA (100 ng/µl)

1 µl Taq polymerase

10 µl 10× Taq Buffer

85 µl H$_2$O

| Number of Cycles | Temperature | Time |
|---|---|---|
| 2 | 95° C. | 30 seconds |
|  | 42° C. | 30 seconds |
|  | 72° C. | 2 minutes, 30 seconds |
| 30 | 95° C. | 30 seconds |
|  | 50° C. | 30 seconds |
|  | 72° C. | 2 minutes, 30 seconds |

GENE LIBRARY SCREENING

PCR products generated in the above reactions (using degenerate primers) were used to make long "run off" single stranded DNA probes using ($P^{32}$ as a label).

The genomic library was screened using the single stranded ($P^{32}$ labeled probe. Hybridization conditions for these screenings were as per Maniatis (maximum stringency for aqueous solutions; 68° C. in rolling hybridization chamber).

All positive clones were then excised into pBluescript SK and sequenced.

EXAMPLE 4

Expression

Positive clones were identified and isolated from the genomic library by the above methods. DNA from the clones were then used as templates in a 100 ul PCR reaction. DNA encoding the enzymes of the present invention were initially amplified from a pBluescript vector containing the DNA by the PCR technique. The amplified sequences were then inserted into a PQE vector and the enzyme was expressed according to the protocols set forth herein.

The pQE vector (Qiagen, Inc. Chatsworth, Calif.) encodes antibiotic resistance (Amp$^r$), a bacterial origin of replication (ori), an IPTG-regulatable promoter operator (P/O), a ribosome binding site (RBS), a 6-His tag and restriction enzyme sites.

The pQE vector was digested with the appropriate restriction enzymes. The amplified sequences were ligated into the respective pQE vector and inserted in frame with the sequence encoding for the RBS. The ligation mixture was then used to transform the *E. coli* strain M15/pREP4 (Qiagen, Inc.) by electroporation. M15/pREP4 contains multiple copies of the plasmid pREP4, which expresses the lacI repressor and also confers kanamycin resistance (Kan$^r$). Transformants were identified by their ability to grow on LB plates and ampicillin/kanamycin resistant colonies were selected. Plasmid DNA was isolated and confirmed by restriction analysis. Clones containing the desired constructs were grown overnight (O/N) in liquid culture in LB media supplemented with both Amp (100 μg/ml) and Kan (25 μg/ml). The O/N culture was used to inoculate a large culture at a ratio of 1:100 to 1:250. The cells were grown to an optical density 600 (O.D.$^{600}$) of between 0.4 and 0.6. IPTG ("Isopropyl-B-D-thiogalacto pyranoside") was then added to a final concentration of 1 mM. IPTG induces by inactivating the lacI repressor, clearing the P/O leading to increased gene expression. Cells were grown an extra 3 to 4 hours. Cells were then harvested by centrifugation.

Numerous modifications and variations of the present invention are possible in light of the above teachings and, therefore, within the scope of the appended claims, the invention may be practiced otherwise than as particularly described. It is to be understood that, while the invention has been described with reference to the above detailed description, the foregoing description is intended to illustrate, but not to limit, the scope of the invention. Other aspects, advantages, and modifications of the invention are within the scope of the following claims. All publications, patent applications, patents, and other referenced mentioned herein are incorporated by reference in their entirety.

What is claimed is:

1. An oligonucleotide probe that hybridizes to a nucleic acid target region contained in a polynucleotide selected from the group consisting of SEQ ID NOs: 1, 3, 5, 7, 9 and 11, wherein the polynucleotide that contains the nucleic acid target region, encodes a protein having polymerase activity, and wherein said oligonucleotide probe specifically hybridizes to the nucleic acid target region.

2. The probe of claim 1, wherein the probe is from 10 to about 150 nucleotides in length.

3. The probe of claim 1, wherein the probe is from 10 to about 100 nucleotides in length.

4. The probe of claim 1, wherein the probe is from 10 to about 50 nucleotides in length.

5. The probe of claim 1, wherein the probe is from 10 to about 30 nucleotides in length.

6. The probe of claim 1, wherein the probe is from 10 to about 15 nucleotides in length.

7. The oligonucleotide of claim 1, wherein the probe comprises a segment of contiguous bases and is at least 70% complementary to a target sequence of 10 contiguous nucleotides present in the target region.

8. The probe of claim 1, wherein the probe is detectably labeled.

9. The probe of claim 8, wherein the detectable label is selected from the group consisting of a radioisotope, a fluorescent compound, a bioluminescent compound, a chemiluminescent compound, a metal chelator or an enzyme.

* * * * *